United States Patent
Krall et al.

(10) Patent No.: US 12,114,930 B2
(45) Date of Patent: Oct. 15, 2024

(54) SYSTEM FOR MEASURING BINOCULAR ALIGNMENT WITH ADJUSTABLE DISPLAYS AND EYE TRACKERS

(71) Applicant: Neurolens, Inc., Costa Mesa, CA (US)

(72) Inventors: Jeffrey P. Krall, Mitchell, SD (US); Aric Plumley, Huntington Beach, CA (US); Ronnie Barnard, Hickory Creek, TX (US); Zachary Dios, Laguna Beach, CA (US); Thomas Henry Holt, Costa Mesa, CA (US); Vivek Labhishetty, Irvine, CA (US); Ali Jiong-Fung Lee, Tustin, CA (US); Ferenc Raksi, Laguna Hills, CA (US); Jason Robert Ryan, Mission Viejo, CA (US)

(73) Assignee: Neurolens, Inc., Coppell, TX (US)

( * ) Notice: Subject to any disclaimer, the term of this patent is extended or adjusted under 35 U.S.C. 154(b) by 764 days.

(21) Appl. No.: 17/179,402

(22) Filed: Feb. 19, 2021

(65) Prior Publication Data
US 2021/0169322 A1    Jun. 10, 2021

Related U.S. Application Data

(63) Continuation-in-part of application No. 16/579,826, filed on Sep. 23, 2019, now Pat. No. 11,589,745,
(Continued)

(51) Int. Cl.
*A61B 3/14*    (2006.01)
*A61B 3/00*    (2006.01)
(Continued)

(52) U.S. Cl.
CPC .............. *A61B 3/14* (2013.01); *A61B 3/0041* (2013.01); *A61B 3/0091* (2013.01); *A61B 3/08* (2013.01);
(Continued)

(58) Field of Classification Search
CPC ....... A61B 3/14; A61B 3/0041; A61B 3/0091; A61B 3/08; A61B 3/113; H04N 5/33;
(Continued)

(56) References Cited

U.S. PATENT DOCUMENTS 3,245,745 A    4/1966    Hancock
4,056,311 A    11/1977   Winthrop
(Continued)

FOREIGN PATENT DOCUMENTS

CN    1438852 A      8/2003
CN    103815866 A    5/2014
(Continued)

OTHER PUBLICATIONS

Wisnicki M.D., "Bifocals, Trifocals, and Progressive-Addition Lenses," American Academy of Ophthalmology, vol. XVII, No. 6, Jun. 1999.
(Continued)

*Primary Examiner* — Mohammed A Hasan

(57) ABSTRACT

A system to determine a binocular alignment, comprises a first optical unit, including a first display, to display images for a first eye, actuatable along a longitudinal direction according to a simulated distance and an optical power of the first eye, and a first eye tracker assembly, to track a gaze direction of the first eye, adjustable in a horizontal lateral direction to accommodate a pupillary distance of the first eye; and a second optical unit, including a second display, to display images for a second eye, actuatable along the longitudinal direction according to a simulated distance and an optical power of the second eye, and a second eye tracker assembly, to track a gaze direction of the second eye, adjustable in the horizontal lateral direction to accommodate a pupillary distance of the second eye; and a computer, to determine the binocular alignment based on the gaze directions.

26 Claims, 39 Drawing Sheets

Related U.S. Application Data which is a continuation of application No. 15/696,161, filed on Sep. 5, 2017, now Pat. No. 10,420,467.

(51) Int. Cl.
| | | |
|---|---|---|
| *A61B 3/08* | (2006.01) | |
| *A61B 3/113* | (2006.01) | |
| *H04N 5/33* | (2023.01) | |
| *H04N 13/327* | (2018.01) | |
| *H04N 13/344* | (2018.01) | |
| *H04N 13/383* | (2018.01) | |

(52) U.S. Cl.
CPC .............. *A61B 3/113* (2013.01); *H04N 5/33* (2013.01); *H04N 13/327* (2018.05); *H04N 13/344* (2018.05); *H04N 13/383* (2018.05); *H04N 2213/008* (2013.01)

(58) Field of Classification Search
CPC .. H04N 13/327; H04N 13/344; H04N 13/383; H04N 2213/008
USPC .......................................................... 351/201
See application file for complete search history.

(56) References Cited

U.S. PATENT DOCUMENTS

| | | | |
|---|---|---|---|
| 4,222,639 | A | 9/1980 | Sheedy |
| 4,240,719 | A | 12/1980 | Gunter et al. |
| 4,253,747 | A | 3/1981 | Maitenaz |
| 4,580,882 | A | 4/1986 | Nuchman et al. |
| 4,580,883 | A | 4/1986 | Shinohara |
| 4,606,626 | A | 8/1986 | Shinohara |
| 4,756,305 | A | 7/1988 | Mateik et al. |
| 4,906,090 | A | 3/1990 | Barth |
| 4,961,639 | A | 10/1990 | Lazarus |
| 5,026,151 | A | 6/1991 | Waltuck et al. |
| 5,200,859 | A | 4/1993 | Payner et al. |
| 5,305,028 | A | 4/1994 | Okano |
| 5,381,191 | A | 1/1995 | Levy |
| 5,557,348 | A | 9/1996 | Umeda et al. |
| 5,724,120 | A | 3/1998 | Svochak et al. |
| 5,728,156 | A | 3/1998 | Gupta et al. |
| 5,782,894 | A | 7/1998 | Israel |
| 5,946,075 | A | 8/1999 | Horn |
| 5,969,790 | A | 10/1999 | Onufryk |
| 6,019,470 | A | 2/2000 | Mukaiyama et al. |
| 6,062,691 | A | 5/2000 | Markson |
| 6,106,819 | A | 8/2000 | Sucher |
| 6,142,624 | A | 11/2000 | Morris et al. |
| 6,318,857 | B1 | 11/2001 | Shirayanagi |
| 6,347,869 | B1 | 2/2002 | Xu et al. |
| 6,364,481 | B1 | 4/2002 | O'Connor et al. |
| 6,505,934 | B1 | 1/2003 | Menezes |
| 6,547,387 | B1 | 4/2003 | Katsantones |
| 6,579,478 | B2 | 6/2003 | Lossman et al. |
| 6,652,097 | B2 | 11/2003 | Shirayanagi |
| 6,776,486 | B2 | 8/2004 | Steele et al. |
| 6,789,898 | B2 | 9/2004 | Le Saux et al. |
| 6,871,954 | B2 | 3/2005 | Copeland |
| 6,956,682 | B2 | 10/2005 | Wooley |
| 7,104,647 | B2 | 9/2006 | Krall |
| 7,216,977 | B2 | 5/2007 | Poulain et al. |
| 7,290,878 | B1 | 11/2007 | Hofeldt |
| 7,703,921 | B2 | 4/2010 | Dick et al. |
| 7,828,439 | B2 | 11/2010 | Krall |
| 7,976,157 | B2 | 7/2011 | Croft et al. |
| 8,042,940 | B2 | 10/2011 | Krall et al. |
| 8,100,529 | B2 | 1/2012 | Kozu |
| 8,248,458 | B2 | 8/2012 | Schowengerdt |
| 8,287,124 | B2 | 10/2012 | Krall et al. |
| 8,376,546 | B2 | 2/2013 | Kozu |
| 8,425,034 | B2 | 4/2013 | Wietschorke |
| 9,237,843 | B1 | 1/2016 | Krall et al. |
| 9,274,351 | B2 | 3/2016 | Drobe |
| 9,298,021 | B2 | 3/2016 | Krall et al. |
| 10,048,511 | B2 | 8/2018 | Krall et al. |
| 10,048,512 | B2 | 8/2018 | Krall et al. |
| 11,589,745 | B2 | 2/2023 | Krall |
| 2002/0036750 | A1 | 3/2002 | Eberl |
| 2002/0051116 | A1 | 5/2002 | Van Saarloos et al. |
| 2002/0099305 | A1 | 7/2002 | Fukushima et al. |
| 2006/0092375 | A1 | 5/2006 | Menezes et al. |
| 2006/0139571 | A1 | 6/2006 | Poulain et al. |
| 2006/0170863 | A1 | 8/2006 | Krall |
| 2006/0244915 | A1 | 11/2006 | Clemons et al. |
| 2007/0182923 | A1 | 8/2007 | Kitani et al. |
| 2008/0049152 | A1 | 2/2008 | Hong et al. |
| 2008/0117289 | A1 | 5/2008 | Schowengerdt et al. |
| 2008/0278676 | A1 | 11/2008 | Croft et al. |
| 2009/0153796 | A1* | 6/2009 | Rabner .................. A61B 3/024 351/203 |
| 2009/0153798 | A1 | 6/2009 | Dick |
| 2009/0185137 | A1 | 7/2009 | Krall |
| 2009/0290121 | A1 | 11/2009 | Drobe et al. |
| 2010/0066974 | A1 | 3/2010 | Croft et al. |
| 2010/0109176 | A1 | 5/2010 | Davison |
| 2010/0271590 | A1 | 10/2010 | Kitani et al. |
| 2011/0090455 | A1 | 4/2011 | Gupta et al. |
| 2011/0109822 | A1 | 5/2011 | Kato |
| 2011/0317127 | A1 | 12/2011 | Suzuki et al. |
| 2012/0002163 | A1 | 1/2012 | Neal |
| 2012/0019774 | A1 | 1/2012 | Krall et al. |
| 2012/0019775 | A1 | 1/2012 | Tyrin et al. |
| 2012/0019776 | A1 | 1/2012 | Giraudet |
| 2012/0081661 | A1 | 4/2012 | Yamakaji |
| 2012/0200822 | A1 | 8/2012 | Kaga et al. |
| 2012/0250152 | A1 | 10/2012 | Larson et al. |
| 2012/0307203 | A1 | 12/2012 | Vendel et al. |
| 2012/0317825 | A1 | 12/2012 | Ohta |
| 2013/0010097 | A1 | 1/2013 | Durnell et al. |
| 2013/0265540 | A1 | 10/2013 | Esser et al. |
| 2013/0293531 | A1 | 11/2013 | Cao et al. |
| 2013/0308099 | A1 | 11/2013 | Stack |
| 2014/0028972 | A1 | 1/2014 | Granger et al. |
| 2014/0240675 | A1* | 8/2014 | Narasimha-Iyer ..... A61B 3/032 351/210 |
| 2014/0327875 | A1 | 11/2014 | Blum et al. |
| 2015/0049301 | A1 | 2/2015 | Krall et al. |
| 2015/0212338 | A1 | 7/2015 | Qi |
| 2015/0226983 | A1 | 8/2015 | Carmon et al. |
| 2015/0346515 | A1 | 12/2015 | Kozu |
| 2016/0073870 | A1 | 3/2016 | Bailey |
| 2016/0261608 | A1 | 9/2016 | Hu et al. |
| 2016/0270656 | A1* | 9/2016 | Samec .................. G06T 19/006 |
| 2017/0148215 | A1 | 5/2017 | Aksoy et al. |
| 2017/0293356 | A1 | 10/2017 | Khaderi |
| 2017/0311793 | A1 | 11/2017 | Green |
| 2017/0343835 | A1 | 11/2017 | Carmon et al. |
| 2018/0008141 | A1* | 1/2018 | Krueger ................ A61B 5/7257 |
| 2018/0136486 | A1 | 5/2018 | Macnamara et al. |
| 2019/0069777 | A1 | 3/2019 | Krall et al. |
| 2019/0239790 | A1 | 8/2019 | Gross |

FOREIGN PATENT DOCUMENTS

| | | |
|---|---|---|
| CN | 104204904 A | 12/2014 |
| EP | 02301422 A1 | 3/2011 |
| FR | 2 814 819 | 4/2002 |
| FR | 2 850 763 | 8/2004 |
| JP | 60-92730 | 5/1985 |
| JP | H10-322724 | 4/1998 |
| JP | 11-197108 A | 7/1999 |
| JP | 2002-253509 | 9/2002 |
| JP | 2011-072431 | 4/2011 |
| JP | 2012-100759 | 5/2012 |
| JP | 2016-536105 A | 11/2016 |
| WO | 2007/026368 A2 | 3/2007 |
| WO | WO 2007/068819 | 6/2007 |
| WO | WO 2008/012649 | 1/2008 |
| WO | WO 2011/067361 | 6/2011 |
| WO | WO 2012/160741 | 11/2012 |
| WO | 2013/112705 A1 | 5/2015 |
| WO | 2015/070023 A2 | 5/2015 |

(56) References Cited

FOREIGN PATENT DOCUMENTS

| WO | WO 2015/131399 A1 | 9/2015 |
| --- | --- | --- |
| WO | WO 2016/007124 | 1/2016 |
| WO | WO 2016/020229 | 2/2016 |
| WO | WO 2016/101204 | 6/2016 |
| WO | WO 2016/139662 A1 | 9/2016 |
| WO | WO 2016/149416 A1 | 9/2016 |
| WO | WO 2016/191709 A1 | 12/2016 |
| WO | WO 2017/131770 | 8/2017 |

OTHER PUBLICATIONS

Fogt et al., "Comparison of Fixation Disparities Obtained by Objective and Subjective Methods," Vision Res., vol. 38, No. 3, pp. 411-421.

Shapiro, "Parallel-Testing Infinity Balance. Instrument and Technique for the Parallel Testing of Binocular Vision," Optom Vision Science , vol. 72, No. 12, 1995 pp. 916-923.

Remole et al., "Objective Measurement of Binocular Fixation Misalignment," America! Journal of Optometry and Physiological Optics, vol. 63, No. 8, 1986, pp. 631-638.

Bruce J.W. Evans, "Optometric prescribing for decompensated heterophoria," Optometry in Practice, vol. 9.2, 2008, pp. 63-78.

Teitelbaum et al., "Effectiveness of Base in Prism for Presbyopes with Convergence Insufficiency", Optometry and Vision Science, vol. 86, No. 2, Feb. 2009, pp. 153-156.

Kim, et al., "The Analysis of AC/A Ratio in Nomefractive Accommodative Esotropia Treated with Bifocal Glasses", Korean Journal Ophthalmology, vol. 26, No. 1, Published: 2012, pp. 39-44, col. 2, paragraph 2; ISSN: 1011-8942.

E. H. Kim, et al., "The Relationship between Phoria and the Ratio of Convergence Peak Velocity to Divergence Peak Velocity," Invest. Ophthalmol. Vis. Sci., vol. 51, No. 8, Mar. 24, 2010, pp. 4017-4027.

\* cited by examiner

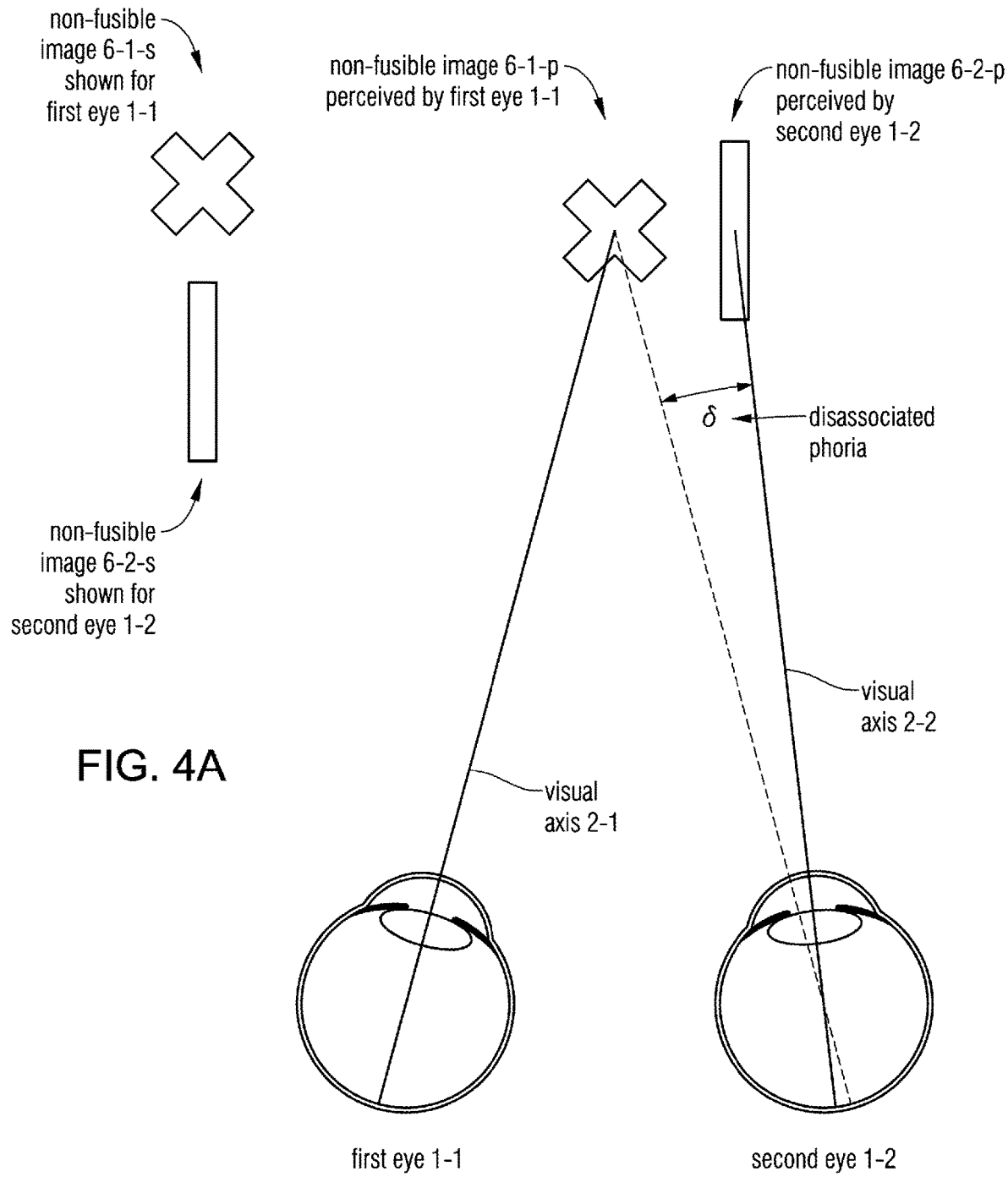

SYSTEM FOR MEASURING BINOCULAR ALIGNMENT WITH ADJUSTABLE DISPLAYS AND EYE TRACKERS

CROSS-REFERENCE TO RELATED APPLICATIONS

The present Application is a continuation-in-part of, and therefore claims benefit from U.S. patent application Ser. No. 16/579,826, entitled: "Method and System for Measuring Binocular Alignment", by Jeffrey P. Krall, and Aric Plumley, filed on Sep. 23, 2019; which is a continuation of U.S. patent application Ser. No. 15/696,161, entitled: "Method and System for Measuring Binocular Alignment", by Jeffrey P. Krall, and Aric Plumley, filed on Sep. 5, 2017, both Applications are hereby incorporated in their entirety by reference.

FIELD OF INVENTION

This invention relates generally to methods and systems for measuring vision acuity, and more particularly, to measuring binocular alignment.

BACKGROUND

With normal vision, an individual is able to focus at objects located at different distances. Ideally, an individual is able to focus on distant objects, referred to as distance-vision, and on near objects, referred to as near-vision. The optical system of the eye uses numerous muscles to change the focus between these distances. These muscles adjust various aspects of the eye when transitioning between distance-vision and near-vision. The muscle adjustments include making subtle changes to the shape of the crystalline lens to adjust the focus of the lens, rotating the eyeballs to rotate their optical axes, and changing the size of the pupils.

Presbyopia is a natural deterioration of near vision, caused by loss of flexibility in the eye's crystalline lenses as one ages. Presbyopia can be partially compensated by wearing "reading" glasses that correct near-vision refraction errors, so that the eye does not have to focus as strongly when gazing at near objects. Presbyopic persons need different optical corrections for near-vision and for distance-vision. However, using two eyeglasses and changing them frequently is distracting. To avoid continually exchanging eyeglasses, bifocals may be used that offer different optical corrections for near-vision and for distance-vision. The transition between these two vision regions can be abrupt or gradual. The latter eyeglasses are called Progressive Addition Lenses (PALs). Abrupt change bifocals have a visible line separating the two vision regions, while PALs have no lines or edges visible between the regions with different dioptric powers.

In spite of all this progress, some types of vision-related discomforts still persist. One of these discomforts is related to a shift of habits in the modern, digital lifestyle. A large and increasing fraction of professions require workers to spend a large and increasing fraction of their working time focusing at close-distance digital interfaces, including computer screens and mobile devices. The same is true for the private lives of many, spending hours playing video games, texting and checking updates on cell phones, among others. All these professional and behavioral shifts rapidly increased the time people spend looking at digital screens, devices, displays, and monitors at a much closer distance than before. The increased time of the eye being trained at near-vision images places excessive demands on the muscles involved in near-vision, often straining them beyond the comfort zone. This can lead to fatigue, discomfort, pain, or even digitally induced migraines. Up to now, there is no widely accepted consensus on the precise causation mechanism of these digital-device related visual discomforts, pains and migraines, even though millions of patients experience these pains every day. Therefore, there is a need for glasses, or other optometric solutions that can provide relief for digital eye discomforts.

FIGS. 1-4 illustrate the basic problem of binocular misalignment. FIG. 1A illustrates that when we look at a near object, like the shown cross, our vision accommodates in two ways. First, we accommodate the optical power of our eyes 1-1 and 1-2 to image the near object at a distance L onto the retina of each eye. This is often called the accommodative response A. Second, we rotate our eyes 1-1 and 1-2 inward by an angle $\alpha$, so that the visual axes 2-1 and 2-2 of the eyes are pointing at the same near object. This response is often called the accommodative convergence AC. For obvious geometric reasons, the angle $\alpha$ of the accommodative convergence AC, relative to the straightforward reference axis, is directly related to the distance L of the accommodative response A: $\alpha=\alpha(L)$. For healthy, well-aligned eyes the ratio of the accommodative convergence AC to the accommodative response A, AC/A, is a geometrically well-defined function, depending on the object distance L and the pupil distance PD of the two eyes.

FIGS. 1B-C illustrate that eyes often display various forms of accommodative misalignments. In FIG. 1B, the two eyes each turn inward, but to a lesser degree than geometry would require. This leads to the accommodative convergence angle $\alpha$ being less than geometrically necessary by a misalignment angle $\beta$. In some detail, the visual axes of the eyes 2-1 and 2-2 should point into the direction denoted as the necessary accommodative alignment to properly see the near object, but, instead, they turn inward to a lesser degree and instead point to the direction denoted as relaxed or natural accommodative alignment.

FIG. 1C illustrates a case, when this lesser turn is asymmetrical. In the shown case, the visual axis 2-1 of the first eye 1-1 properly points to the direction of the necessary accommodative alignment, while the visual axis 2-2 of the second eye 1-2 is turned inward only to the direction of the relaxed or natural accommodative alignment, that is misaligned by the accommodative misalignment angle $\beta$.

FIGS. 2A-D illustrate some types of accommodative misalignments. The definitions of misalignments used by different schools of optometry and by monographies show some discrepancies, and the techniques to characterize these misalignments are also varied. Therefore, the here-shown definitions are meant to be illustrative only, and analogues and equivalents are also within the scope of the illustrated terms.

To place the discussed misalignments into proper context, first the concept of fusing images is introduced. When our two eyes look at the same object, each eye creates its own visual perception. These perceptions are relayed from the eyes to the visual cortex, where the brain fuses the two images and creates a three dimensional (3D) perception of the viewed object. With optometric diagnostic systems, it is possible to test this image fusing. For example, two separate objects of the same shape can be separately projected into the two eyes with deflections, prisms, and mirrors that make the two projections appear to come from a single object. These visual perceptions will be fused by the brain into a perceived single image. Objects projected in this manner are called fusible objects, presenting fusible images.

If in an experiment the distance between the two objects is increased, or the deflection angles are increased, or the shapes of the objects are modified, then the projections into the two eyes start to differ. At some distance, or difference, between the objects, the discrepancy between the visual perceptions of the two eyes exceeds a threshold, and the brain stops fusing the two images into a single perception. Objects with such difference in distance, angle, or shape are called non-fusible objects, presenting non-fusible images.

With this preparation, FIGS. 2A-D illustrate the concept of fixation disparity, as measured by a test device, often called the Mallet box. The Mallet box displays two vertically aligned bars, and an "X O X" horizontal "anchor". In some implementations, the two bars can be shifted sideways. In others, adjustable mirrors or prisms are placed in front of the patient's eye to achieve the same horizontal shift. With appropriate selective optics, the anchor and only one of the bars is shown for the first eye 1-1 as a centered bar 5-1-c, and the same anchor plus only the other bar is shown for the second eye 1-2 as a centered bar 5-2-c. The anchor and the centered bars 5-1-c and 5-2-c are clearly fusible. Accordingly, the brains of patients without accommodative misalignment problems will properly fuse these images.

FIG. 28 illustrates that patients with accommodative misalignments will not fuse the images properly. What is typically observed is that, while the images of the anchor, seen by both eyes, are properly fused into a single image, the bars are perceived as shifted. The first eye 1-1 perceives a shifted bar 5-1-s, while the second eye 1-2 perceives a shifted bar 5-2-s. The angle γ between the line to the image center and one of the visual axes 2-1 and 2-2 is called fixation disparity.

FIGS. 2C-D illustrate ways to measure the angle needed to counteract, or compensate the fixation disparity. In the system of FIG. 2C, the two bars are counter-shifted. A counter-shifted bar 5-1-x is shown for the first eye 1-1, and a counter-shifted bar 5-2-x is shown for the second eye 1-2. The bars are counter-shifted until the patient perceives the two bars as aligned. The angle corresponding to these counter-shifts, γ*, between the visual axes and line to the counter-shifted bars is measured and is typically referred to as an associated phoria. In the system of FIG. 2D, the bars are not counter-shifted. Instead, adjustable, or exchangeable prisms 7 are inserted in front of the patient's eyes. These prisms are adjusted or exchanged until the two bars are perceived as aligned by the patient. Then the prism angles, or the refraction angles of the refracted visual axes, are reported as the associated phoria γ*.

FIG. 3 illustrates how increasing a partial associated phoria partially compensates fixation disparity. Strictly speaking, the (full) associated phoria, that fully compensates fixation disparity, is given by the intersect of this curve with the partial associated phoria axis. If human vision were a purely optical process, the partial associated phoria would be simply equal to the negative of the partially compensated fixation disparity. Accordingly, the curve would be a straight line through the origin, tilted by −45 degrees, pointing from the upper left corner to the lower right corner. However, FIG. 3 illustrates that human vision is much more complex, and perception and image processing play crucial roles in it. FIG. 3 shows four types of relations between the partially compensated fixation disparity and the partial associated phoria. Visibly, none of these lines are straight, none of them go through the origin, and two of them don't even intercept the horizontal axis. These type 11 and II relations mean that no amount of partial associated phoria can compensate the fixation disparity in full. Therefore, it remains a substantial challenge to determine the associated phoria that fully compensates a patient's fixation disparity. A convention is mentioned in closing: the fixation disparity is referred to as "exo", if the eyes do not turn inward to the necessary degree, while it is referred to as "eso" in those rare cases, when the eyes turn inward too much.

FIGS. 4A-C illustrate a related visual misalignment called disassociated phoria. To characterize disassociated phoria, an experiment similar to that in FIGS. 2A-D can be carried out, with the difference that instead of showing fusible images 5-1 and 5-2, the optometrists show non-fusible images 6-1-s and 6-2-s for the first eye 1-1 and the second eye 1-2. In FIG. 4A, these non-fusible images are the cross and the bar. As FIG. 41 illustrates, once the eyes are unable to fuse the images, often one or both of the visual axes rotate outward. In the shown asymmetric case, the visual axis 2-2 of the second eye 1-2 rotates outward by an accommodative misalignment angle δ. This angle δ of the outward rotation is measured and called disassociated phoria. In various applications, as below, the disassociated phoria is distributed over the two eyes evenly, thus the disassociated phoria per eye equaling δ/2. In some cases, e.g. as illustrated in FIG. 1C, the disassociated phoria δ may manifest itself unevenly and has to be distributed between the eyes accordingly.

FIG. 4C shows a particularly clear case, when simply no image is shown for the second eye 1-2, the view of the second eye 1-2 is blocked. This is an extreme case of non-fusible images. As for FIG. 4B, in response to the block, the visual axis 2-2 of the second eye 1-2 rotates outward by a measurable disassociated phoria angle δ.

As a quantitative characterization of accommodation misalignments, including fixation disparity and disassociated phoria, several practitioners use the misalignment-impacted AC/A ratio. The AC/A is a ratio of the accommodative convergence angle reduced by the fixation disparity, α-δ/2, (expressed with its tangent, in terms of "prism diopters" Δ), divided by the accommodative distance L, expressed in diopters D. A typical definition of AC is AC=100 tan(α−δ/2), in terms of prism diopters. For an average visual performance, an AC/A ratio of 6-6.5 Δ/D is necessary, while, remarkably, in large population segments the average of the misalignment-impacted AC/A ratio was measured to be about 3.5 Δ/D. Clearly, various forms of accommodative misalignment affect a large percentage of the population, and any progress towards relief from this is highly valuable.

A startling fact of the corresponding field of optometry is that the associated phoria angles and the disassociated phoria angles, determined by experienced practitioners, show remarkably wide variations. Experiments carried out on the same patient by different optometrists, and sometimes even by the same optometrist at different times, report phoria angles, expressed in prism diopters Δ, with a distribution having a standard deviation as much as 3Δ. (A prism diopter of 1Δ corresponds to a 1 cm prism refraction at 1 meter distance). The large variability of these methods precludes the effective determination and compensation of accommodative misalignments.

This exceptionally large standard deviation is probably due to several factors. These include the followings. (1) The methods of determination use the patient's subjective responses as key inputs. (2) Some methods use central images, while others use peripheral images for determining the associated phoria. The relative accuracy and relevance of these methods was not yet critically evaluated. (3) Most practitioners use a single measurement, or a single method, thus not benefiting from possibly important medical information that can be gleaned from carrying out multiple tests. (4) In a previous exploratory project, Applicants also discovered that the prismatic reaction of the eyes is quite different for moving test images. However, understanding the relation of optimal prismatic corrections based on static and moving test images is in its early stages. (5) While there are several ways to define prismatic misalignments, and they produce different prismatic predictions and diagnoses, eventually a single prism needs to be formed in the spectacles. It is far from obvious how to convert and combine the various diagnostically determined prismatic corrections into a single prism prescription. Applicants are not aware of a critical study that would have evaluated how the efficacy and variability of prism prescriptions depended on the possible combinations of the determined prismatic corrections.

For all of the above reasons, determining the prismatic power that optimally compensates accommodative misalignments remains a pressing medical need.

SUMMARY

To address the above described medical needs, some embodiments include a system to determine a binocular alignment, comprising a first optical unit, including a first display, to display images for a first eye, actuatable along a longitudinal direction according to a simulated distance and an optical power of the first eye, and a first eye tracker assembly, to track a gaze direction of the first eye, adjustable in a horizontal lateral direction to accommodate a pupillary distance of the first eye; and a second optical unit, including a second display, to display images for a second eye, actuatable along the longitudinal direction according to a simulated distance and an optical power of the second eye, and a second eye tracker assembly, to track a gaze direction of the second eye, adjustable in the horizontal lateral direction to accommodate a pupillary distance of the second eye; and a computer, coupled to the first optical unit and the second optical unit, to determine the binocular alignment based on the gaze directions of the first eye and the second eye.

BRIEF DESCRIPTION OF THE DRAWINGS

FIGS. 4A-C illustrate methods to determine disassociated phoria.

DETAILED DESCRIPTION

The systems described in the present patent document address the above articulated medical needs at least in the following aspects. (1) The described system and method determine the prismatic corrections only by objective measurements, without subjective input from the patient. This aspect alone greatly reduces the patient-to-patient and practitioner-to-practitioner variations of the results. In fact, studies on large samples of patients using Applicant's system and method determined prismatic corrections with a standard deviation reduced from the above mentioned 3Δ to well below 1Δ. This significant reduction of the results' standard deviation alone established the here-described method to the status of quantitatively predictive diagnostic methods. (2) The system and method use both central and peripheral test images, because of a newly developed understanding of how the peripheral and the central prismatic corrections are connected. Therefore, the described system and method is a promising platform to determine an optimal compromise prismatic prescription that strikes the best compromise for compensating both central and peripheral accommodative misalignments. (3) The described method has two stages, thus it determines the eventual prismatic correction in a second stage by building on the important misalignment information acquired in the first stage. As such, the method integrates knowledge determined by different methods and benefits from the information determined by all of them. (4) One of the stages of the method involves moving test images. Therefore, the eventually determined prismatic corrections capture and integrate the dynamic prismatic response of the eye as well. (5) The reliable repeatability and small variability of the above mentioned large scale study provided a compelling argument that Applicants' method combined the outputs of different methods in an objective and effective manner to produce a single optimized and objective prismatic correction. The here-described five aspects provide advantages individually and in combinations.

FIGS. 5-10 illustrate a system 10 for determining a binocular alignment, and FIGS. 11-16 illustrate a corresponding method 100 for determining the binocular alignment.

Figure 5:
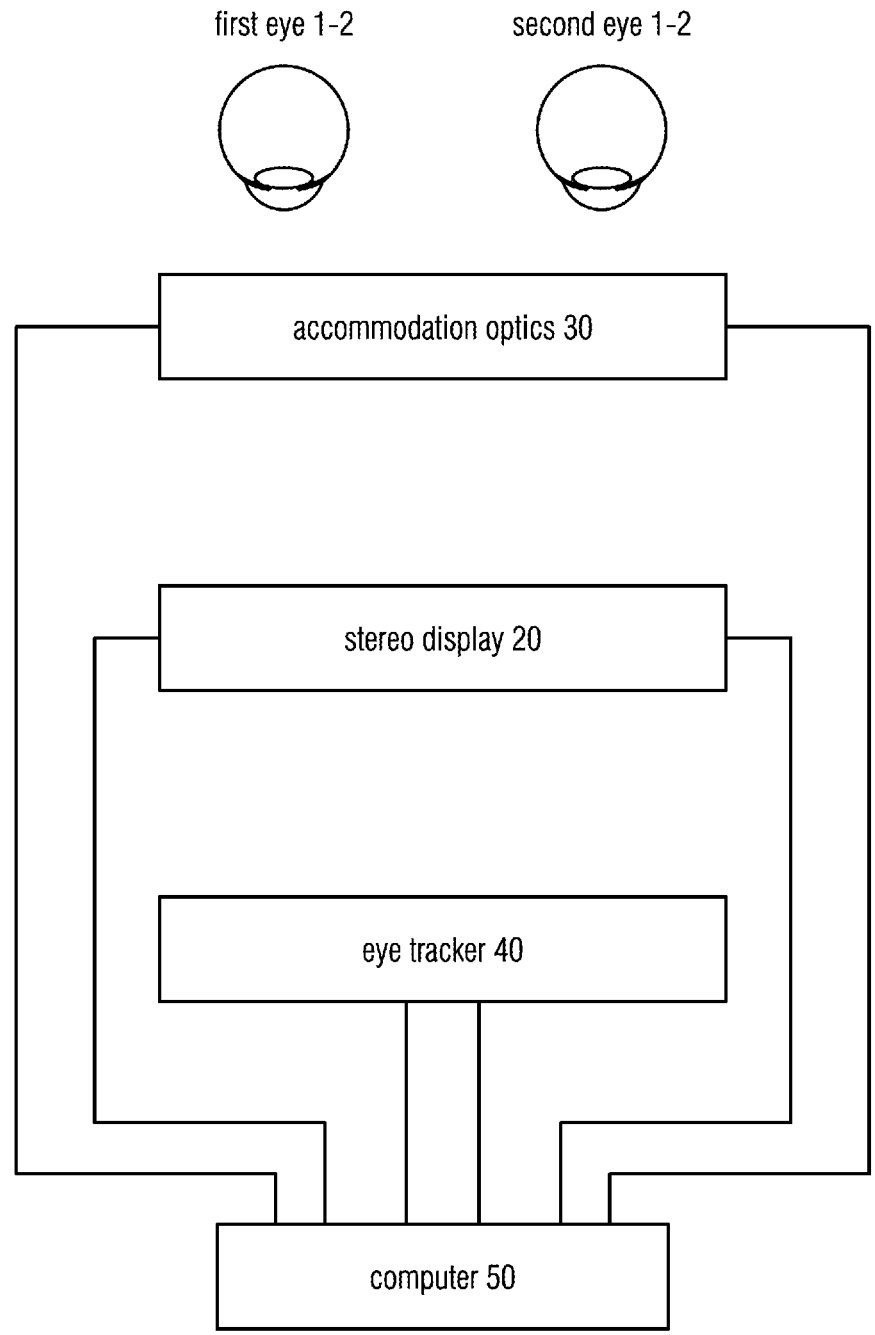
FIG. 5 illustrates a system for determining a binocular misalignment.

FIG. 5 illustrates that in some embodiments, the system 10 for determining a binocular alignment can comprise a stereo display 20, to project visible images for a first eye 1-1 and a second eye 1-2; an accommodation optics 30, to modify the projected visible images according to an apparent distance; an eye tracker 40, to track an orientation of the first eye 1-1 and the second eye 1-2; and a computer 50, coupled to the stereo display 20, the accommodation optics 30 and the eye tracker 40, to manage a determination of the binocular alignment. In what follows, the eyes will be labeled as first eye 1-1 and second eye 1-2. This labeling can correspond to a left eye and a right eye, or vice versa.

Figure 6A:
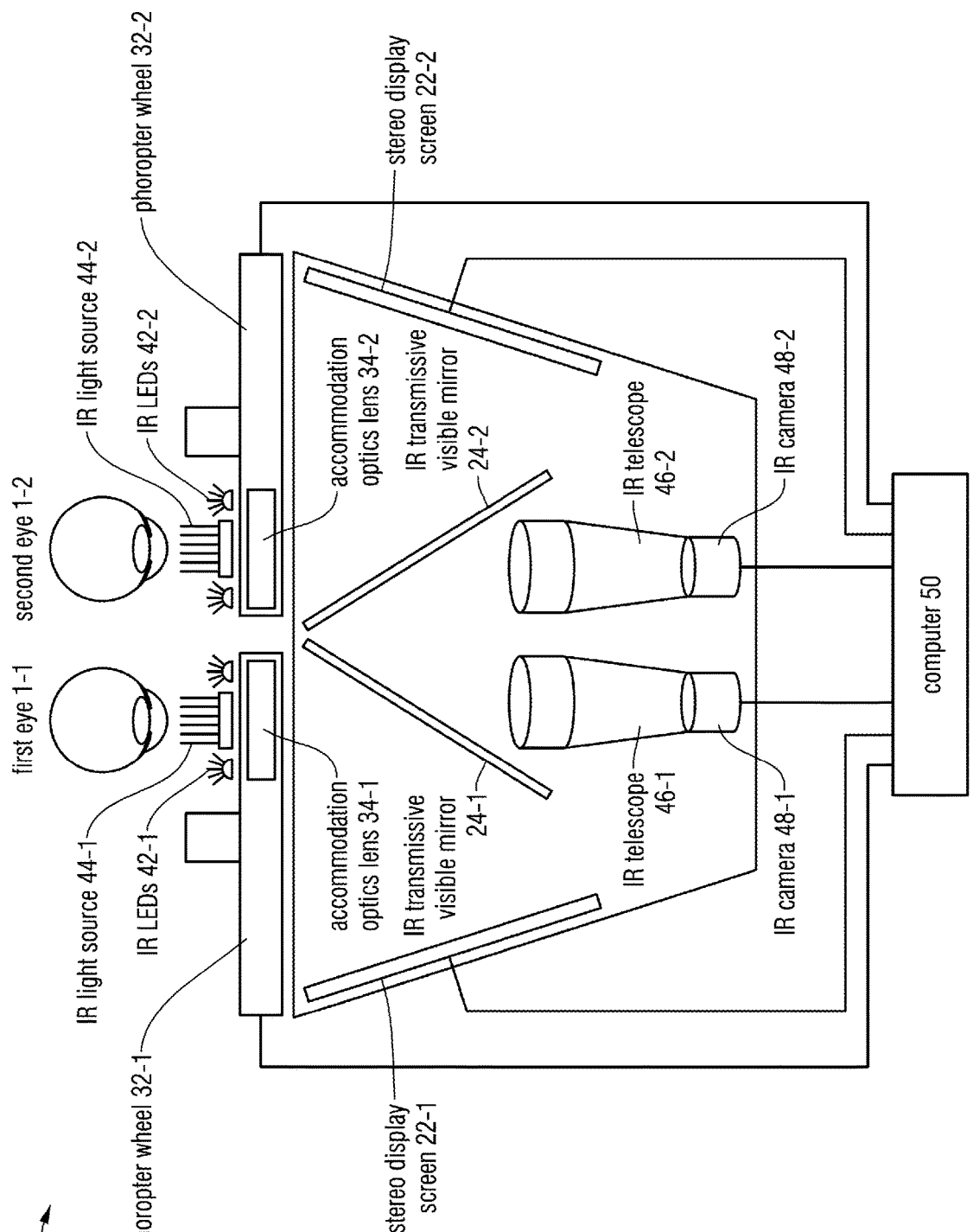
FIGS. 6A-B illustrate an embodiment of the system for determining a binocular misalignment.

FIG. 6A shows a detailed illustration of some embodiments of the system 10. In some embodiments, the eye tracker 40 can include infrared light emitting diodes, or IR LEDs, 42-1 and 42-2, positioned close to a front of the system 10, to project infrared eye-tracking beams on the first eye 1-1 and the second eye 1-2, as well as infrared light sources 44-1 and 44-2, to illuminate the first eye 1-1 and the second eye 1-2 with an infrared imaging light. The infrared eye-tracking beams and the infrared imaging light get both reflected from the eyes 1- and 1-2. The eye tracker 40 can further include infrared (IR) telescopes 46-1 and 46-2, with infrared (IR) cameras 48-1 and 48-2, to detect the infrared eye-tracking beams and the infrared imaging light, reflected from the first eye 1-1 and the second eye 1-2.

Many of the elements of the system 10 are included in pairs, e.g., the infrared telescopes 46-1 and 46-2. For simplicity of presentation, such pair of elements will be referred to only by their lead identifiers where doing so does not lead to misunderstanding, such as "the infrared telescope 46", abbreviating "the infrared telescopes 46-1 and 46-2."

Figure 7:
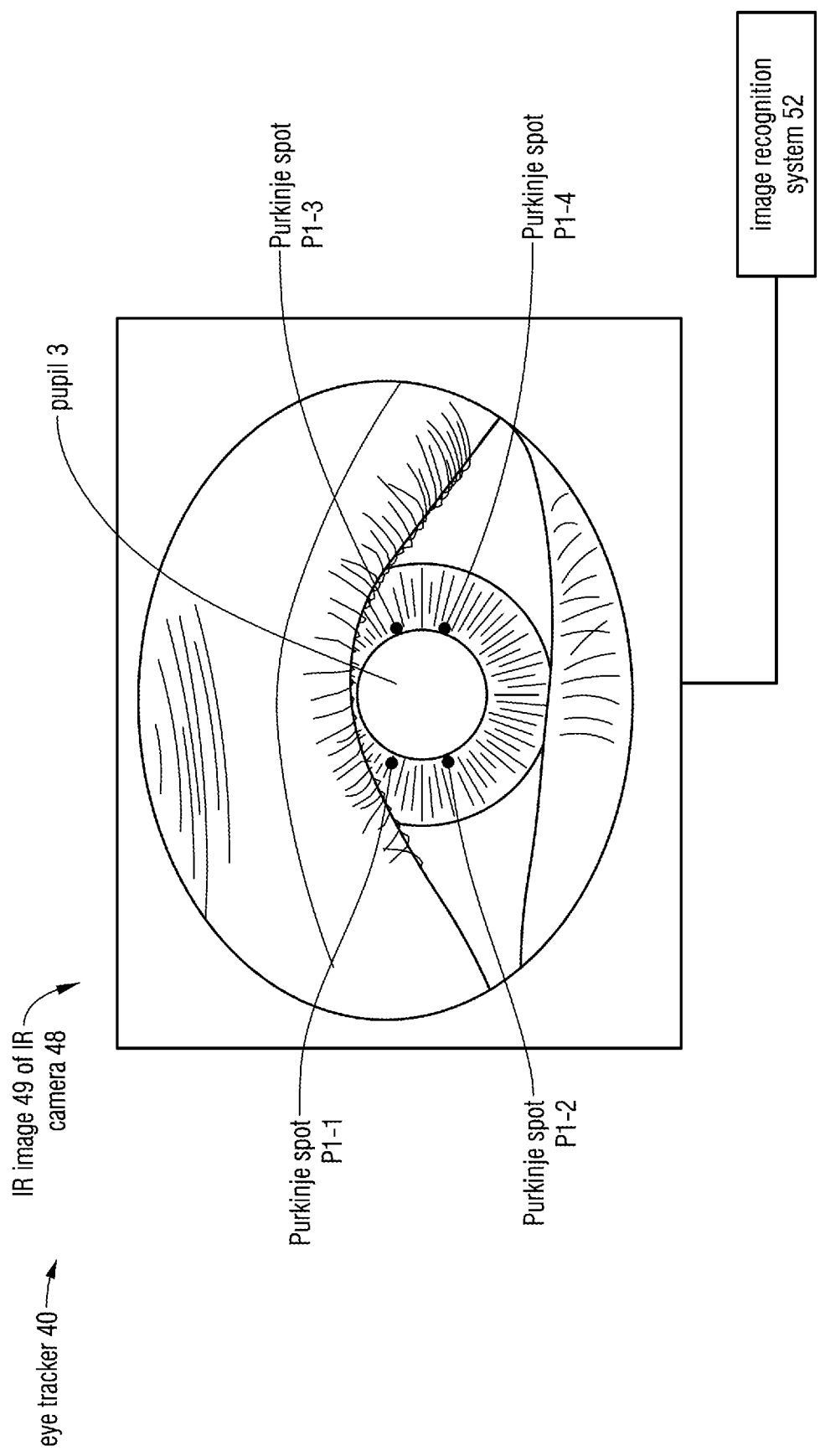
FIG. 7 illustrates an JR image by the eye tracker.

FIG. 7 illustrates a resulting IR image 49, as detected, or sensed, by the IR camera 48. In this embodiment, there are four IR LEDs 42-1, . . . 42-4 for each eye separately. To avoid clutter, the "-1" or "-2" indicating a particular eye, is omitted in the description of FIG. 7. The "-1" . . . "-4" notation here refers to the four IR LEDs, all projecting IR eye tracking beams onto the same eye. The four IR LEDs 42-1, . . . 42-4 project four IR eye-tracking beams onto the eye, which reflect from the cornea, creating four so called Purkinje spots P1-1, . . . P1-4 in the IR image 49. The "P1" notation refers to the reflection from the proximal surface of the cornea. The higher indexed Purkinje spots P2, . . . refer to reflections from deeper lying surfaces inside the eye, such as reflections from the proximal and distal surfaces of the capsule. The here-described embodiments utilize the P1 Purkinje spots, while other embodiments may employ higher indexed Purkinje spots.

The reflected IR imaging light of the IR light source 44 is detected by the IR camera 48 as well. The four Purkinje spots P1-1, . . . P1-4 overlaid on the detected reflected IR imaging light together form the IR image 49, as shown.

In some embodiments, the eye tracker 40 can include an image recognition system 52, to determine an orientation of the first eye 1-1 and the second eye 1-2, using the detected infrared eye tracking beams, forming the Purkinje spots P1-1, . . . P1-4, and the detected infrared imaging light, together forming the IR image 49. The image recognition system 52 can extract, for example, an image of the contour of a pupil 3, using edge-recognition methods. Then it can determine an orientation of the eye 1 from the center of the pupil 3. Separately, it can determine the orientation of the eye from the Purkinje spots P1-1, . . . P1-4. Finally, it can employ a weighing algorithm to determine a "best result" orientation by combining the two determined orientations, using various well known image recognition and analysis techniques. The image recognition system 52 can be a separate processor, a separate application specific integrated circuit, or it can be implemented as a software deployed in the system-managing computer 50.

Figure 6B:
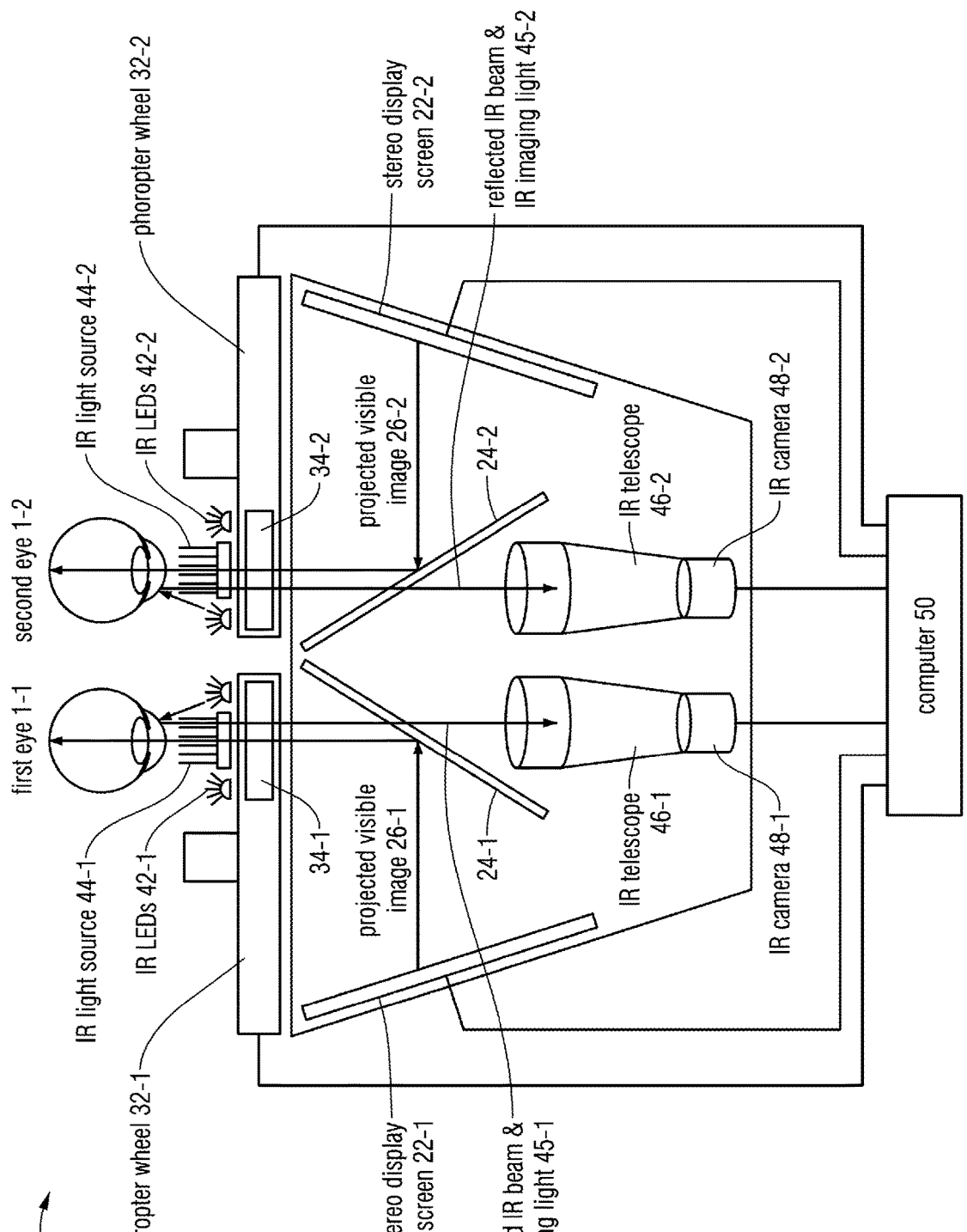

FIGS. 6A-B illustrate that the system 10 can further include infrared-transmissive visible mirrors 24-1 and 24-2, one for each eye, to redirect the projected visible images 26-1 and 26-2, from the stereo display 20 to the first eye 1-1 and the second eye 1-2; and to transmit the reflected infrared eye tracking beam and the infrared imaging light, together 45-1 and 45-2, from the first eye 1-1 and the second eye 1-2. In these embodiments, stereo display screens 22-1 and 22-2 of the stereo display 20 can be positioned peripheral to a main optical pathway of the system 10, and the infrared telescopes 46-1 and 46-2 of the eye tracker 40 can be positioned in the main optical pathway of the system 10. For reference, the accommodation optics lenses 34—mirror 24—IUR telescope 46 axis for each eye is typically referred to as the main optical pathway in this embodiment. Also, for clarity's sake, in figures where the optical paths and beam are shown, some labels have been simplified.

FIG. 6B shows that in this embodiment, the peripheral stereo display screens 22-1 and 22-2 can project visible images 26-1 and 26-2 towards the main optical pathway of the system 10, that are redirected by the infrared-transmissive visible mirrors 24-1 and 24-2 toward the eyes 1- and 1-2. At the same time, the reflected IR eye tracking beams and the reflected IR imaging lights, together 45-1 and 45-2, reflected from the eyes 1-1 and 1-2, are transmitted by the same infrared-transmissive visible mirrors 24-1 and 24-2 toward the IR telescopes 46-1 and 46-2 along the main optical pathway of the system 10.

Figure 8A:
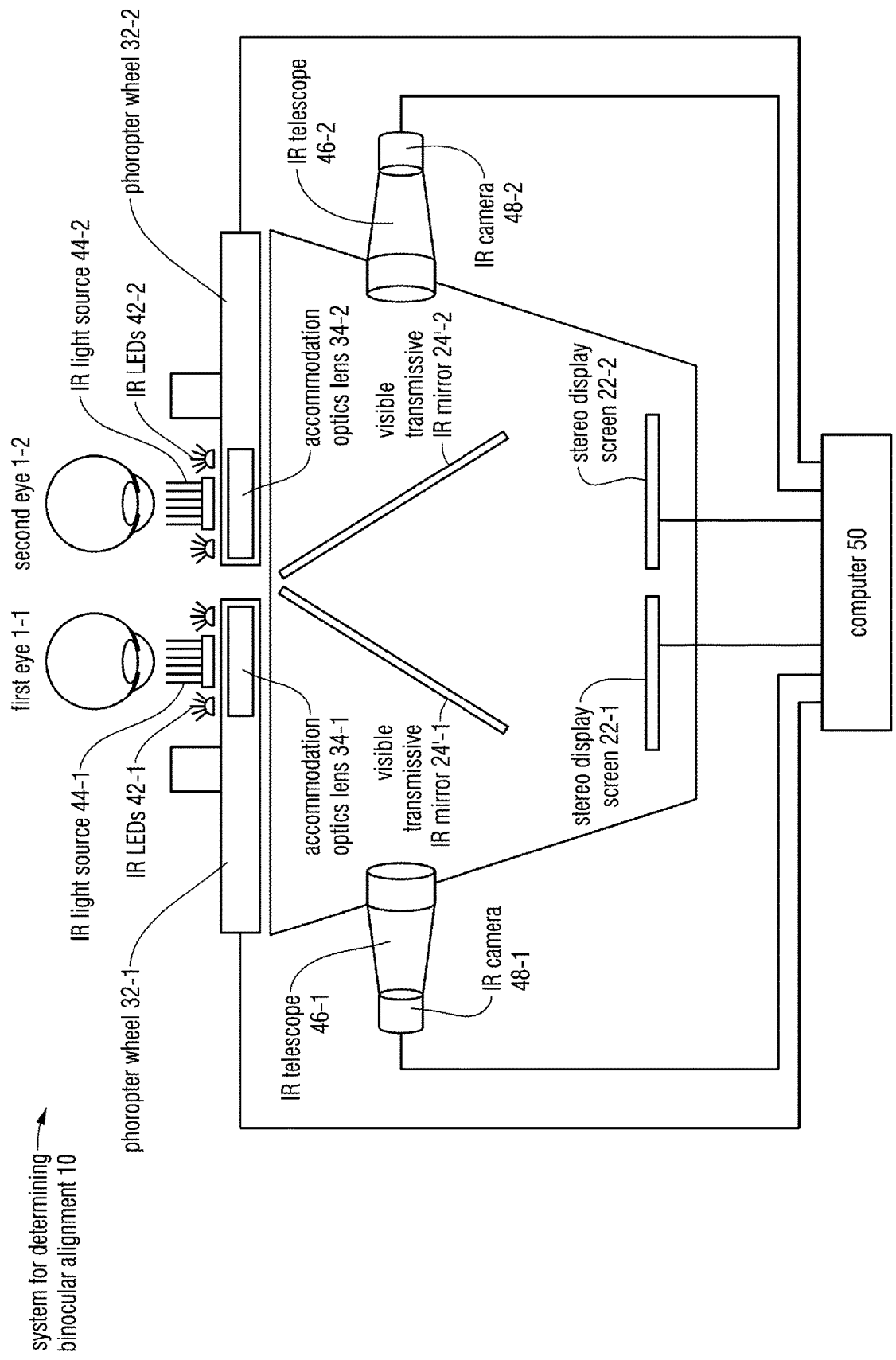
FIGS. 8A-B illustrate an embodiment of the system for determining a binocular misalignment.

FIG. 8A illustrates another embodiment, where the location of the stereo display screens 22 and the IR telescopes 46 is exchanged. FIG. 88 illustrates that this embodiment can include visible-transmissive infrared (1R) mirrors 24'-1 and 24'-2, to redirect the reflected infrared eye tracking beam and the reflected infrared imaging light, together 45-1 and 45-2, reflected from the first eye 1-1 and the second eye 1-2, toward the IR telescopes 46-1 and 46-2. At the same time, the visible-transmissive infrared mirrors 24'-1 and 24'-2 can transmit the projected visible images 26-1 and 26-2, from the stereo display screens 22-1 and 22-2 of the stereo display 20 to the first eye 1-1 and the second eye 1-2. In these embodiments of the system 10, the stereo display 20 can be positioned in the main optical pathway of the system 10, and the infrared telescopes 46 of the eye tracker 40 can be positioned peripheral to the main optical pathway of the system 10. For reference, in this embodiment, the accommodation optics lenses 34—mirror 24—stereo display screen 22 axis for each eye is typically referred to as the main optical pathway in this embodiment.

Figure 8B:
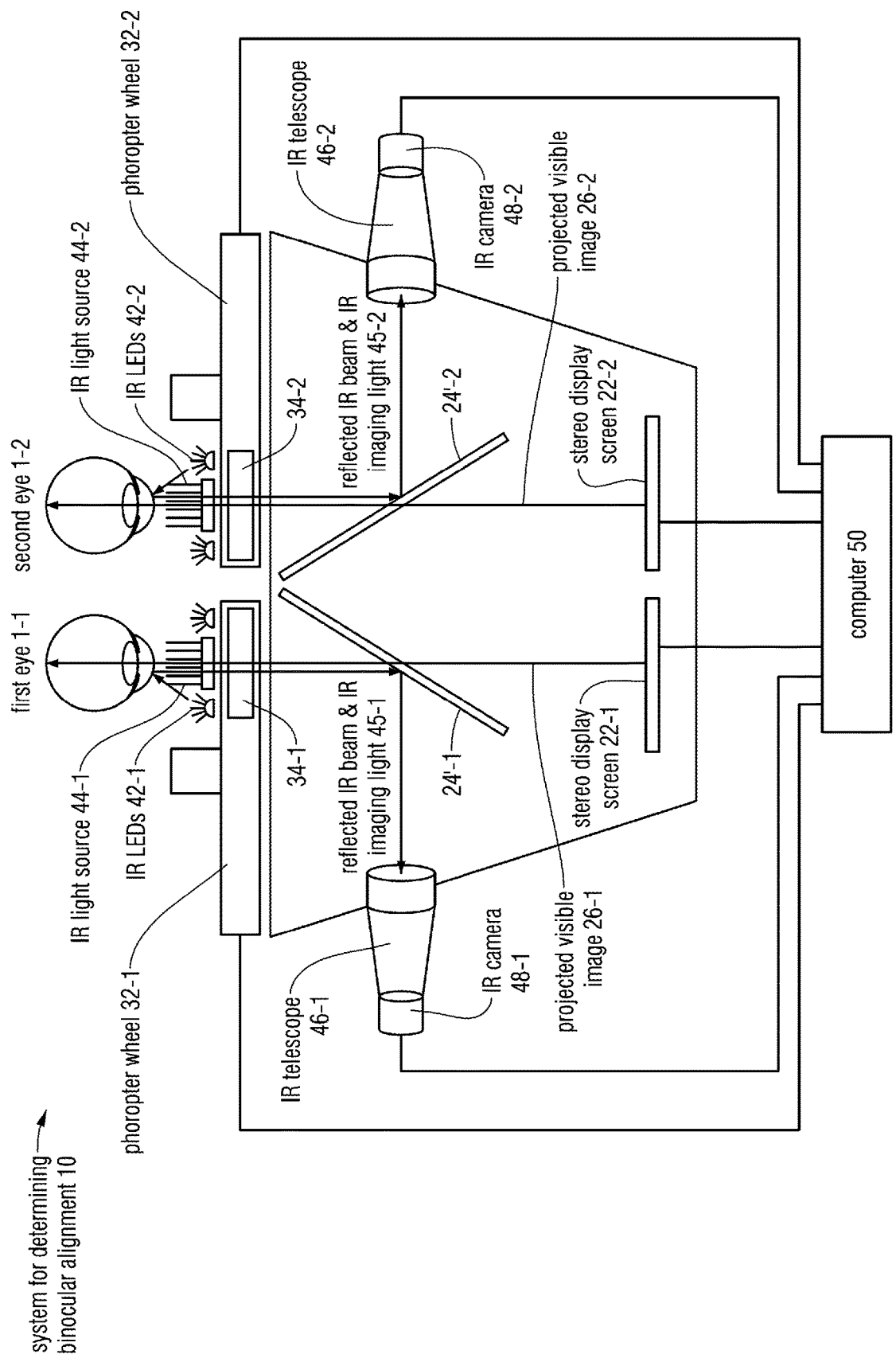
Figure 9:
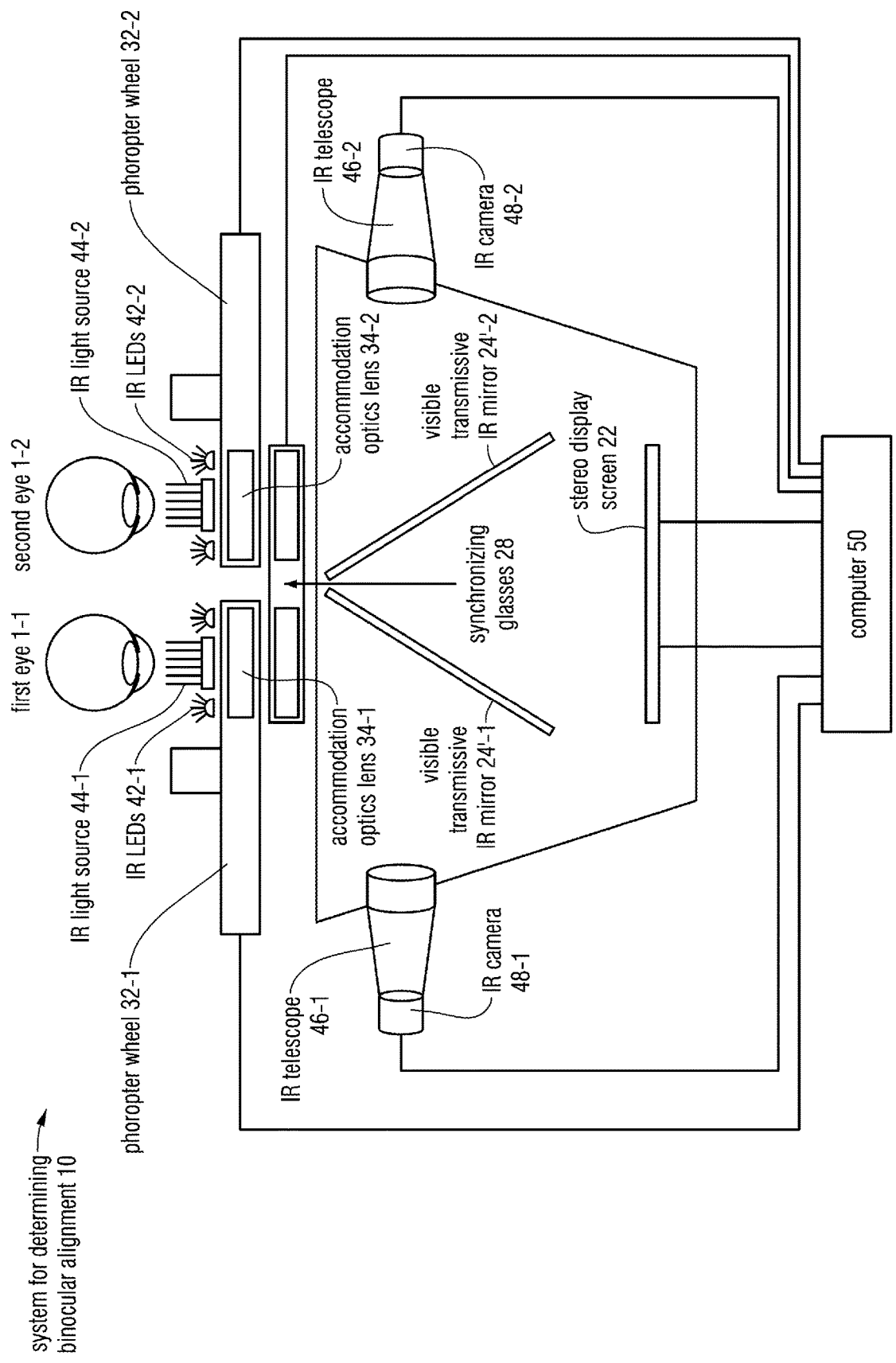
FIG. 9 illustrates an embodiment of the system for determining a binocular misalignment.

FIG. 9 illustrates a variant of the system 10 of FIGS. 8A-B, in which the stereo display 20 can include a single stereo display screen 22, and synchronizing glasses 28. The synchronizing glasses 28 can be shutter glasses or polarized glasses. In this embodiment, the projected visible images 26-1 and 26-2 of the left and right stereo display screen 22-1 and 22-2 of FIGS. 8A-B are both displayed by the single stereo display screen 22 in a rapidly alternating sequence. The synchronizing glasses 28 can be precisely coordinated with this alternating sequence, allowing the projection of the visible images 26-1 and 26-2 to the first eye 1-1 and the second eye 1-2 in a rapidly alternating manner, creating the impression of separate images being projected into these eyes. The synchronizing glasses 28 can be analogous to the 3D glasses used in the projection of 3D movies, and can rely on liquid crystal LCD layers that can rapidly change the circular polarization of the two lenses of the synchronizing glasses 28. Such systems 10 can achieve smaller footprints for the system 10 that can be advantageous. For optimal operations, a sufficiently wide field of view for the stereo display screen 22 can be helpful.

Some embodiments of the system 10 do not need to include the mirrors 24 or 24'. In these systems, the eye tracker 40 may include small implementations of the IR cameras 48, positioned close to the front of the system 10, slanted at a sufficiently large angle so that the IR cameras 48 do not block the projections by the stereo display screens 22. The image recognition system 52 of such implementations of the eye tracker 40 can include a geometric transformation unit to determine the direction of the eye visual axes from a substantially slanted IR image 49 and Purkinje spots P1, . . . P4, possibly some spots even being obscured by the slant.

In embodiments of the system 10, the accommodation optics 30 can include phoropter wheels 32-1 and 32-2 with a series of accommodation optics lenses 34-1 and 34-2 of varying optical power. These accommodation optics lenses 34 are useful to simulate the apparent distance for the first eye 1-1 and the second eye 1-2.

As described below in relation to the method 100, the system 10 can be employed to project visible images 26 at different apparent distances for a patient. Doing so can involve at least two technical solutions. First, inserting the accommodation optics lenses 34 with their variable optical power into the main optical pathway can create the impression of the projected visible images 26 being farther or closer. Second, projecting the visible images 26-1 and 26-2 closer or farther from each other can simulate an appropriate vergence of these images, another important factor in making these images appear as being at the apparent distance for the patient.

In some embodiments, for the first technical solution, the accommodation optics 30 can include, in place of the phoropter wheel 32, or in combination with the phoropter wheel 32, curved mirrors, trial lenses, flip in/flip out lenses, adjustable liquid lenses, deformable mirrors, z-directionally movable mirrors, rotating diffractive optical elements, translating diffractive optical elements, variable focus moire lenses, or focusing lens groups.

Figure 10B:
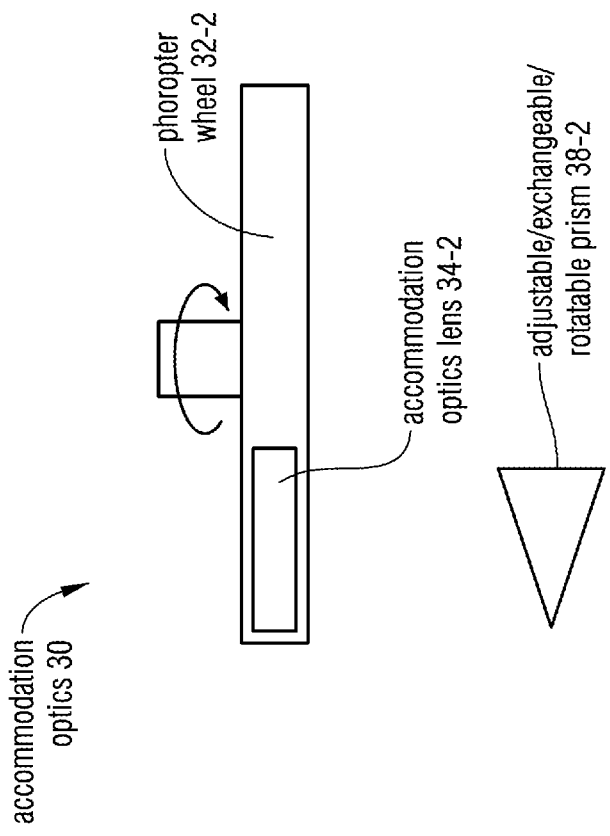
FIGS. 10A-B illustrate embodiments of the accommodation optics.
Figure 10A:
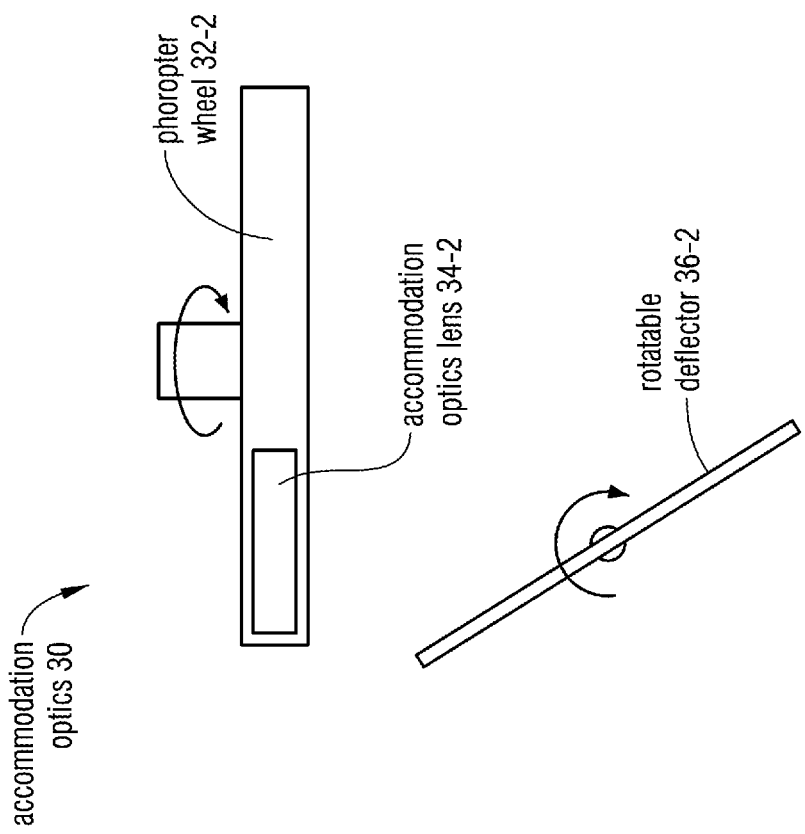

FIGS. 10A-B illustrate that for the second technical solution, the accommodation optics 30 can include a pair of rotatable deflectors 36, rotatable prisms 38, or adjustable prisms 38 (only one shown), to deflect the projection of the images 26-1 and 26-2 to the first eye 1-1 and the second eye 1-2, to simulate a vergence of the apparent distance for the first eye and the second eye.

In some embodiments, the vergence can be simulated not by the above optical elements, but by shifting the projecting of the projected visible images 26-1 and 26-2 with the stereo display screens 22-1 and 22-2 towards each other, in other words, projecting them closer to each other.

In some systems 10 the accommodation optics 30 and the stereo display 20 can be combined into a single light field display that includes a microlens array, where the projected visible images 26-1 and 26-2 shown on the stereo display screens 22-1 and 22-2, combined with the optical characteristics of the microlens array can be used to vary the apparent distance of the projected visible images 26-1 and 26-2 as seen by a patient.

In some systems 10, the accommodation optics 30 and the stereo display 20 can be combined into a single light field display that includes a mems scanner, a focus modulator, or a light source.

Having described the problem of prismatic or accommodative misalignments and embodiments of the system 10 that were developed to provide progress in the context of the misalignment problems, next, various methods 100 will be described for determining binocular misalignments using embodiments of the system 10.

FIGS. 11-16 illustrate a method 100 of how to use the above described embodiments of the system 10 to determine a binocular alignment of the eyes 1-1 and 1-2.

Figure 11:
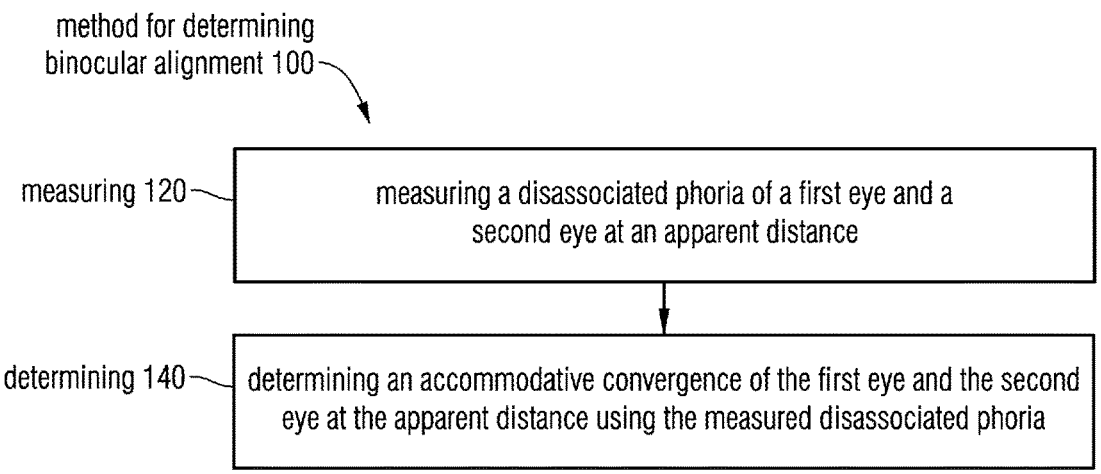
FIG. 11 illustrates a method for determining a binocular misalignment.

FIG. 11 illustrates that some embodiments of the method 100 can include a measuring 120 of a disassociated phoria of the first eye 1-1 and the second eye 1-2 of a patient at an apparent distance, and a determining 140 of an accommodative convergence of the first eye 1-1 and the second eye 1-2 at the apparent distance using the measured disassociated phoria. As mentioned earlier, the method 100 is a two-stage method, and thus its results integrate the information and knowledge revealed by the two different stages.

As described below in detail, in some embodiments, the measuring 120 can include projecting non-fusible visible images 26-1 and 26-2 for the first eye 1-1 and the second eye 1-2 using the stereo display 20 of the system 10. For the purpose of describing the method 100 more concisely, the visible images 26-1 and 26-1 of FIGS. 5-10 will be simply referred to as images 26-1 and 26-2 in what follows.

Figure 1A:
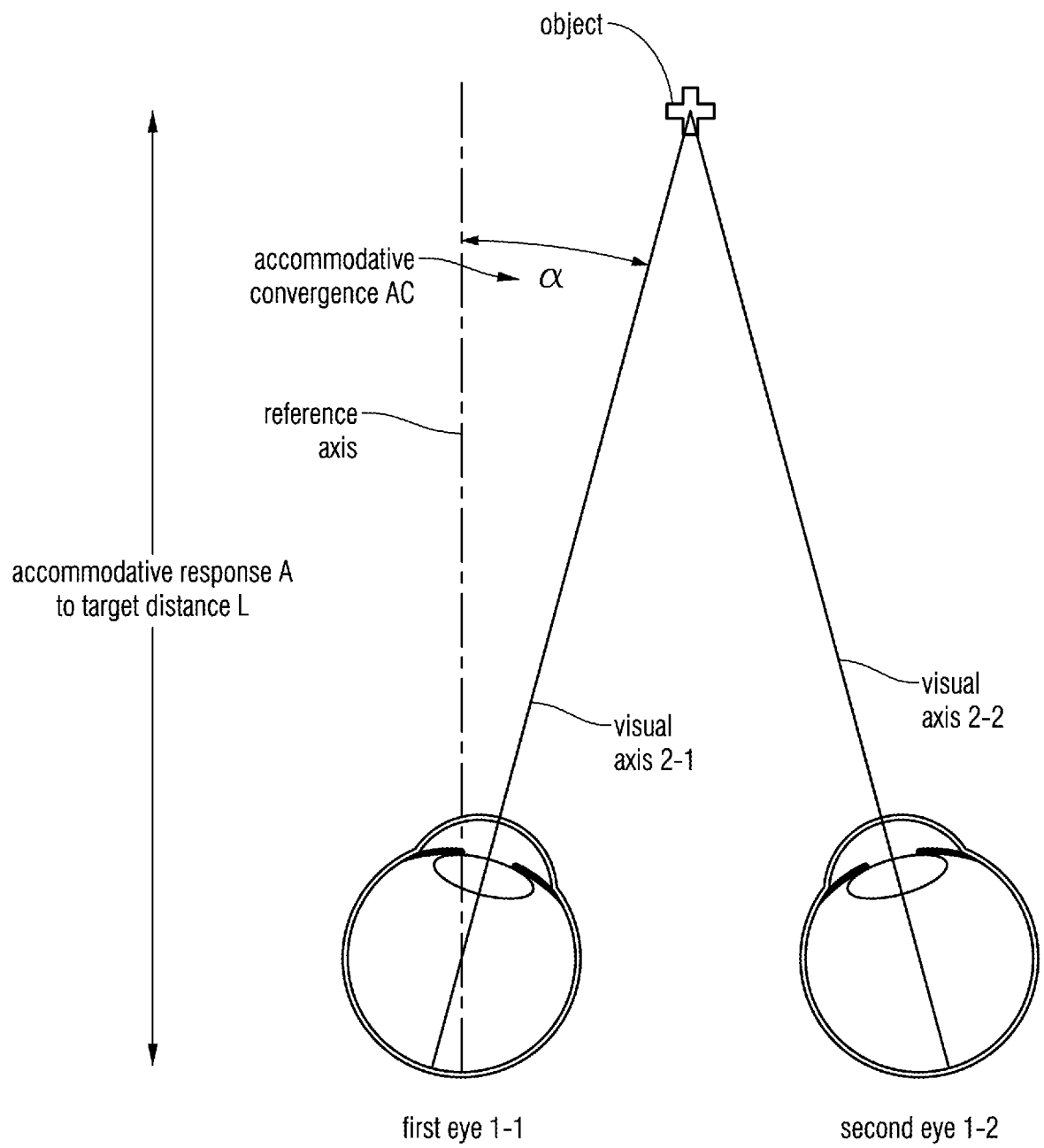
FIGS. 1A-C illustrate various accommodative misalignments.
Figure 1B:
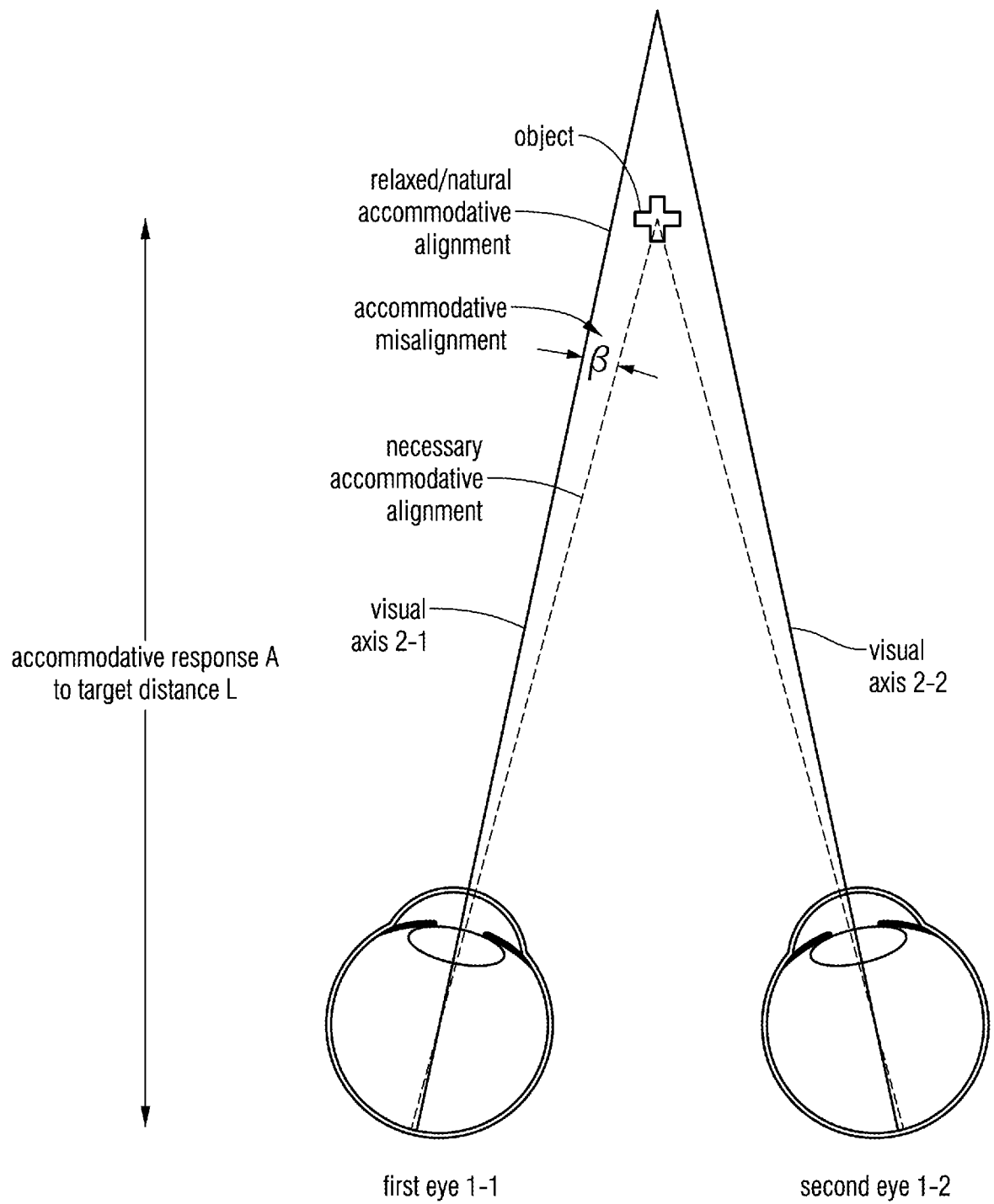
Figure 1C:
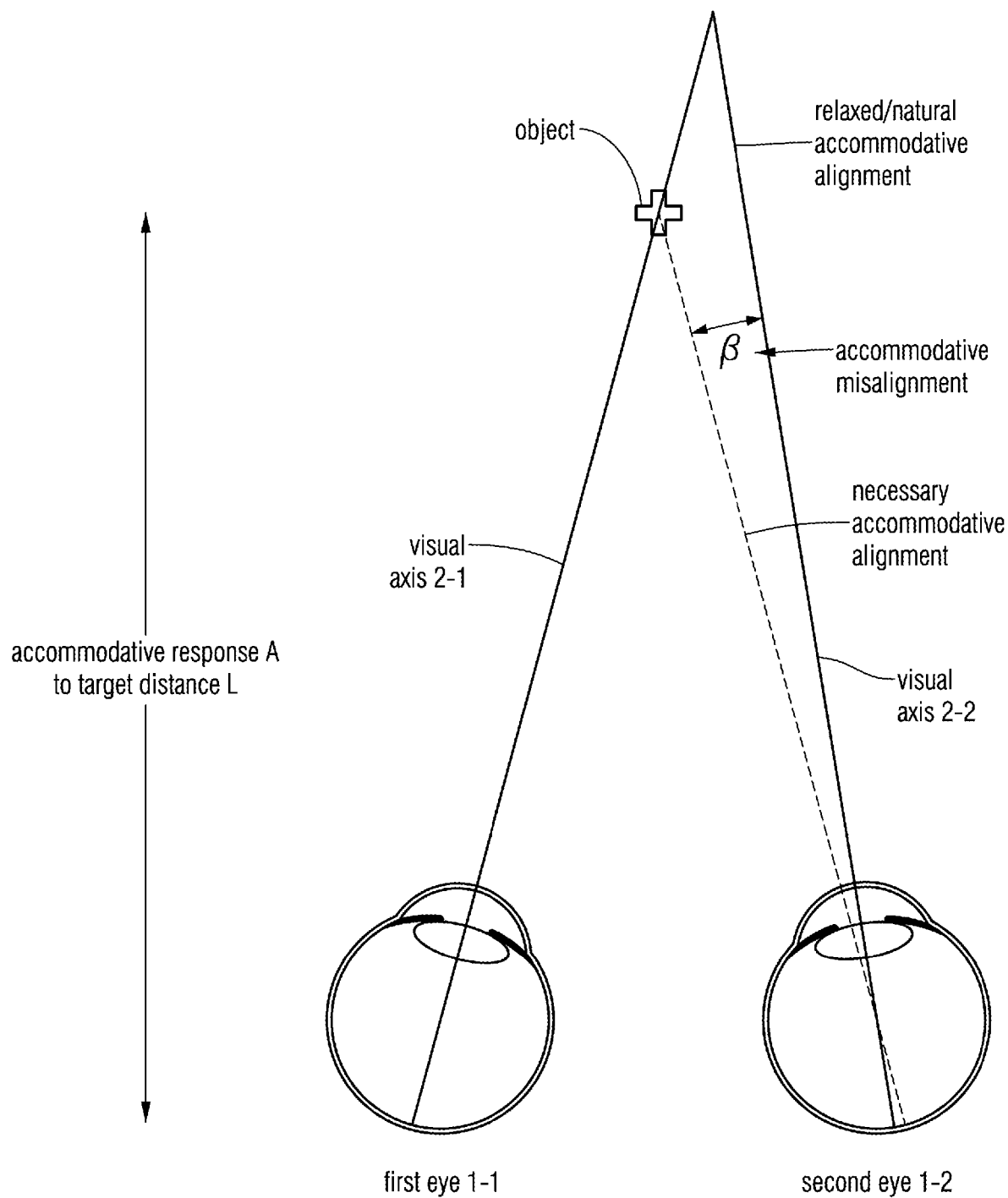
Figure 2A:
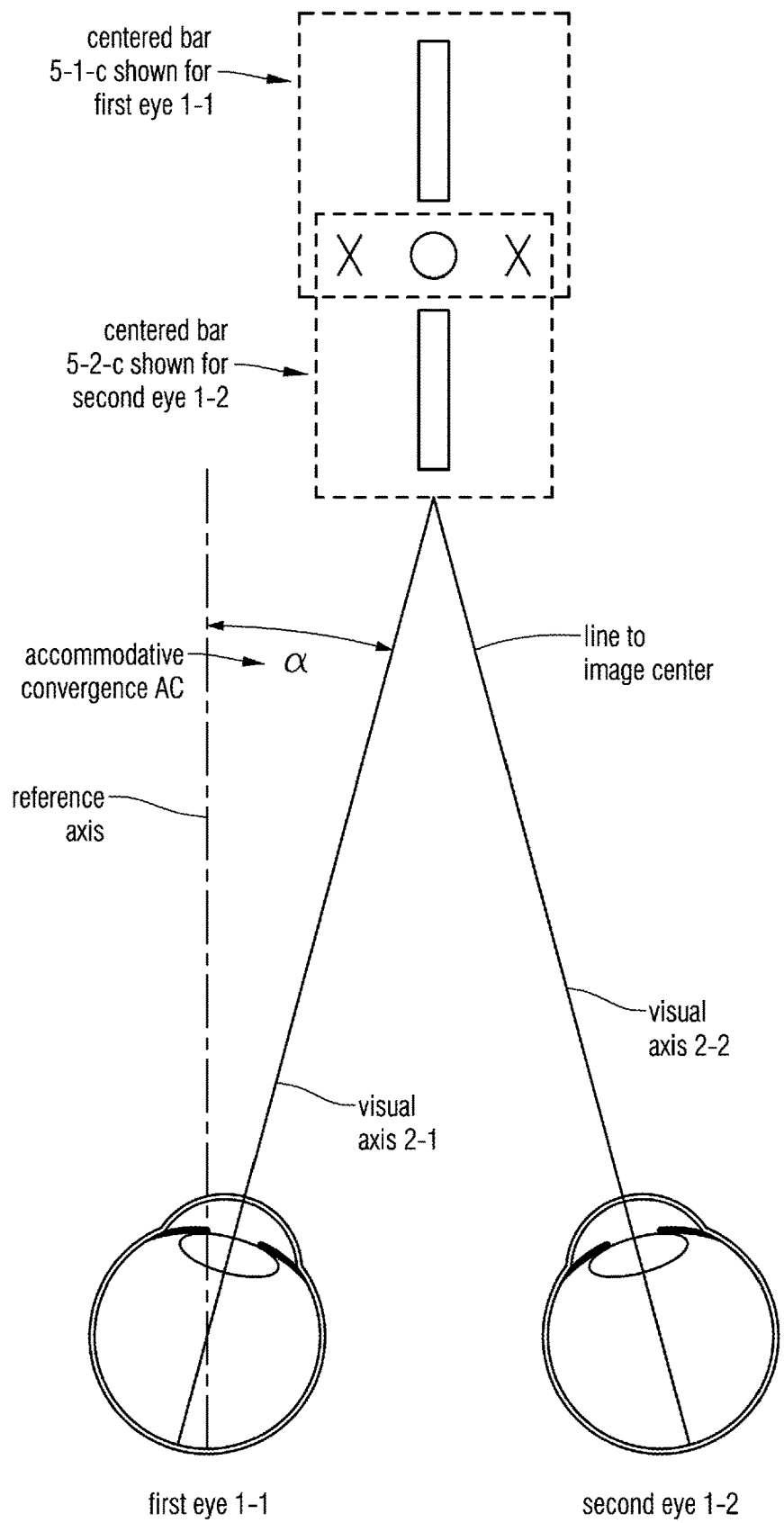
FIGS. 2A-D illustrate a method to determine types of accommodative misalignments.
Figure 2B:
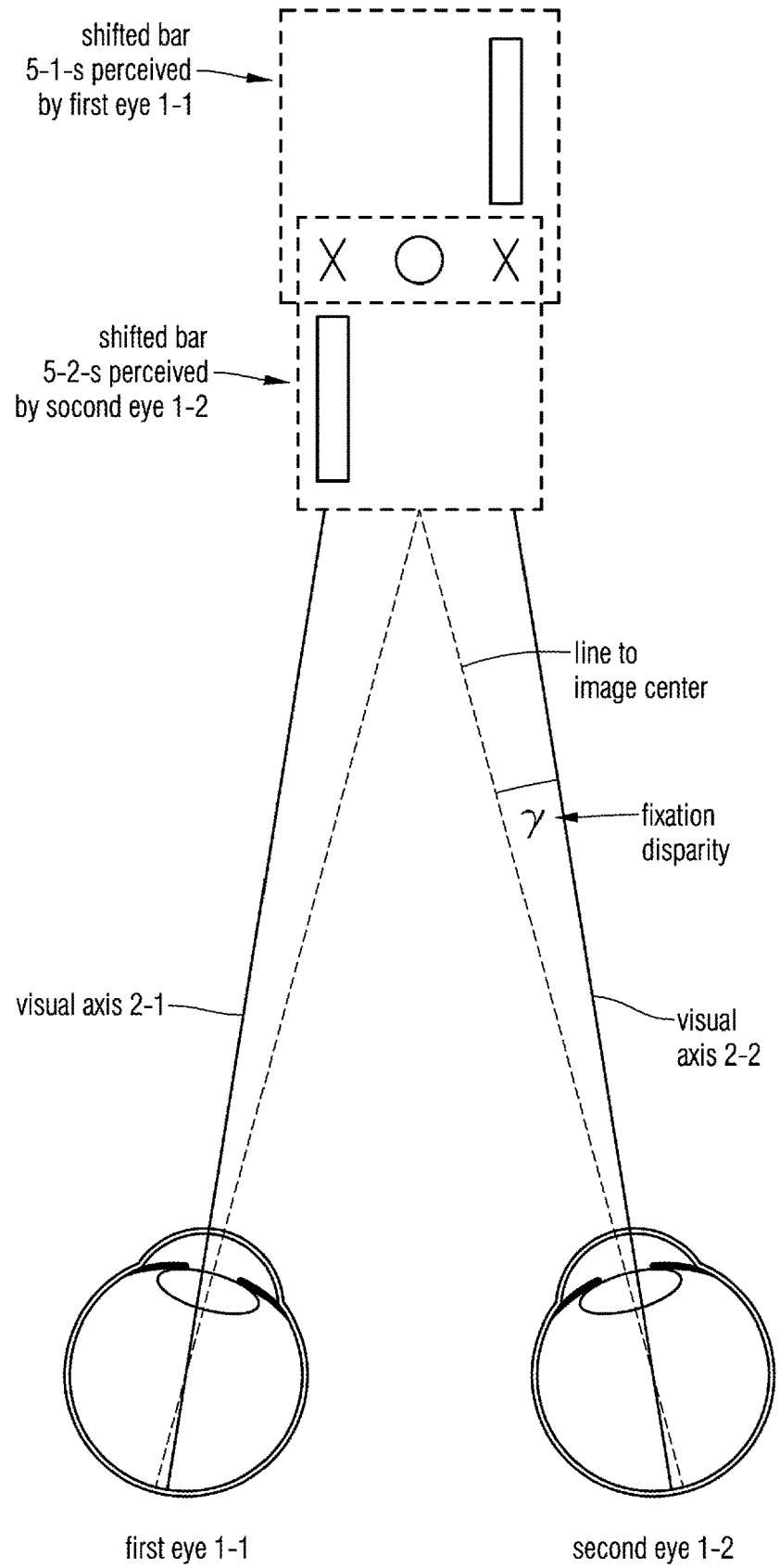
Figure 2C:
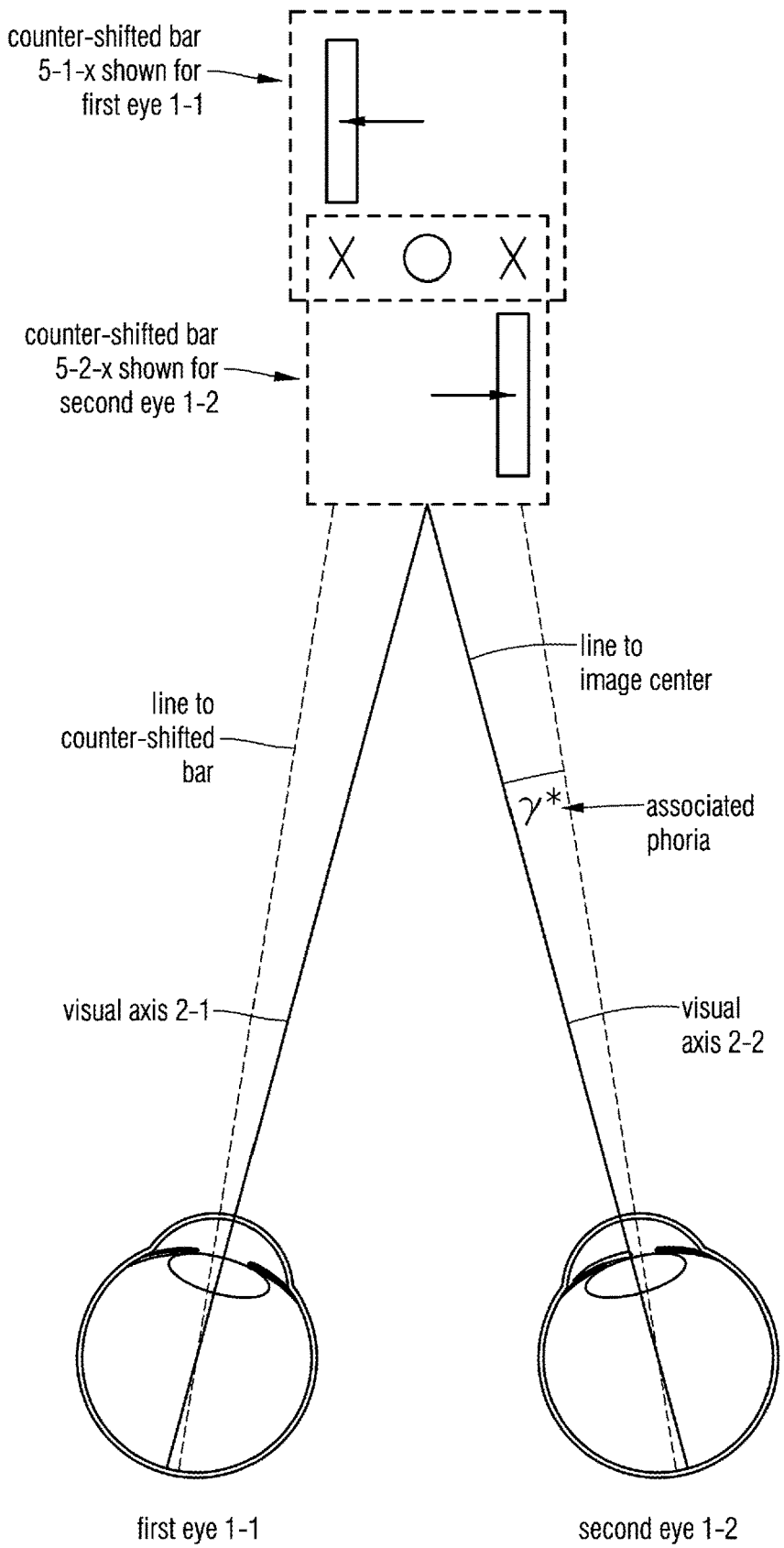
Figure 2D:
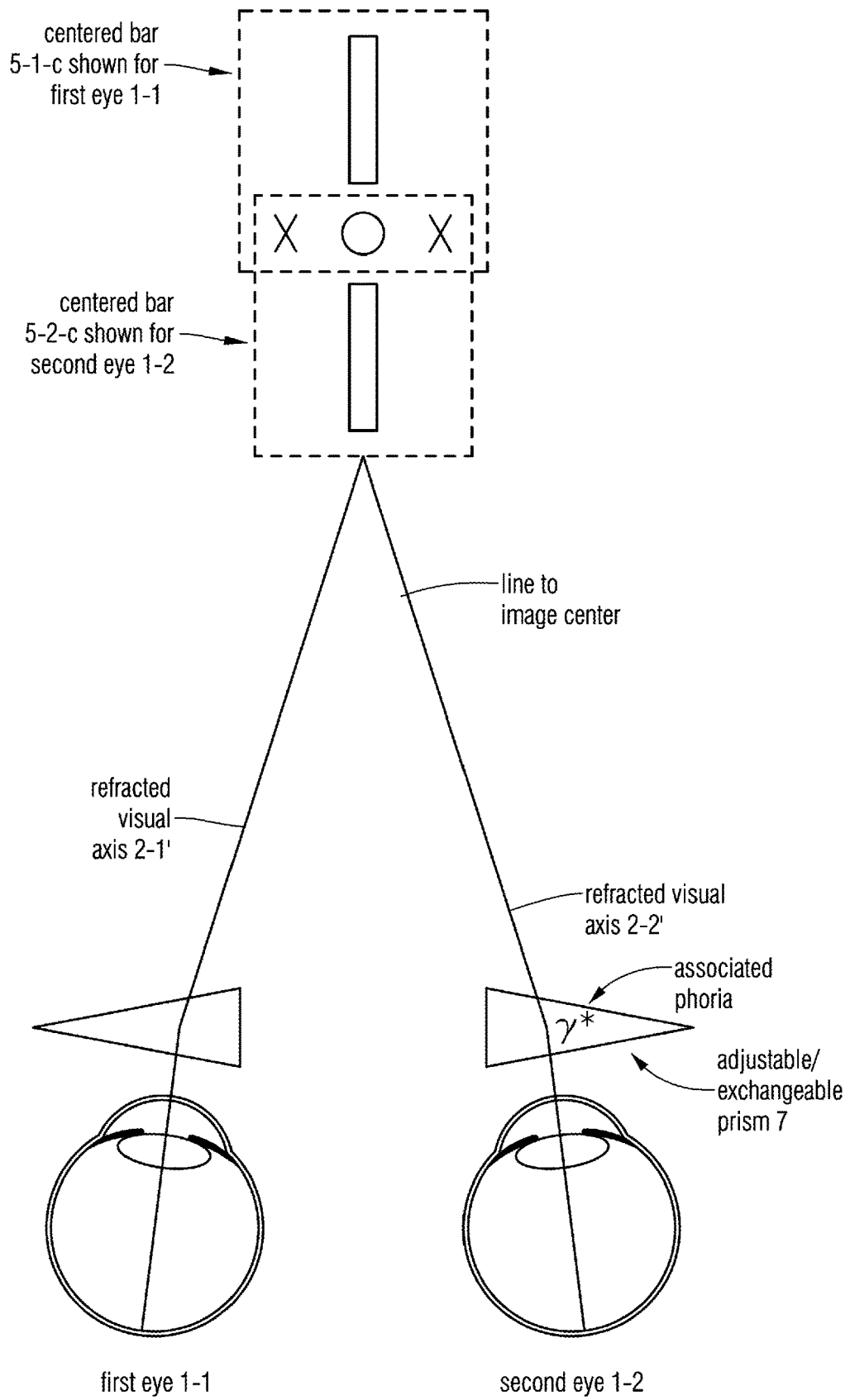

Examples of projecting non-fusible images in order to determine a disassociated phoria have been described, e.g., in relation to FIGS. 2C-D. There, the two non-fusible images 6-1-s and 6-2-s were of comparable appearance, or dominance. Some embodiments of the method M also involve projecting such non-fusible images of comparable dominance.

In other embodiments, the projecting can include projecting a dominant image for the first eye 1-1, and projecting a non-dominant image for the second eye 1-2. As described in relation to FIGS. 2C-D, the eye 1-2 that sees the non-dominant image often starts wandering off after the brain's efforts to fuse the two non-fusible images fail. In these embodiments, the measuring 120 can include tracking the eyes 1-1 and 1-2 with the eye tracker 40, and determining when the wandering eye 1-2 eventually achieves a relaxed orientation. Achieving this relaxed state can be inferred, for example, by the eye tracker 40 determining that the movement of the eye 1-2 slowed below a threshold, or changed from a directional movement to a random jitter, or came to a halt. Once the eye tracker 40 determined that the eye 1-2 reached the relaxed state, the disassociated phoria can be measured by measuring an orientation of at least one of the first eye 1-1 and the second eye 1-2 by the eye tracker 40.

Figure 12:
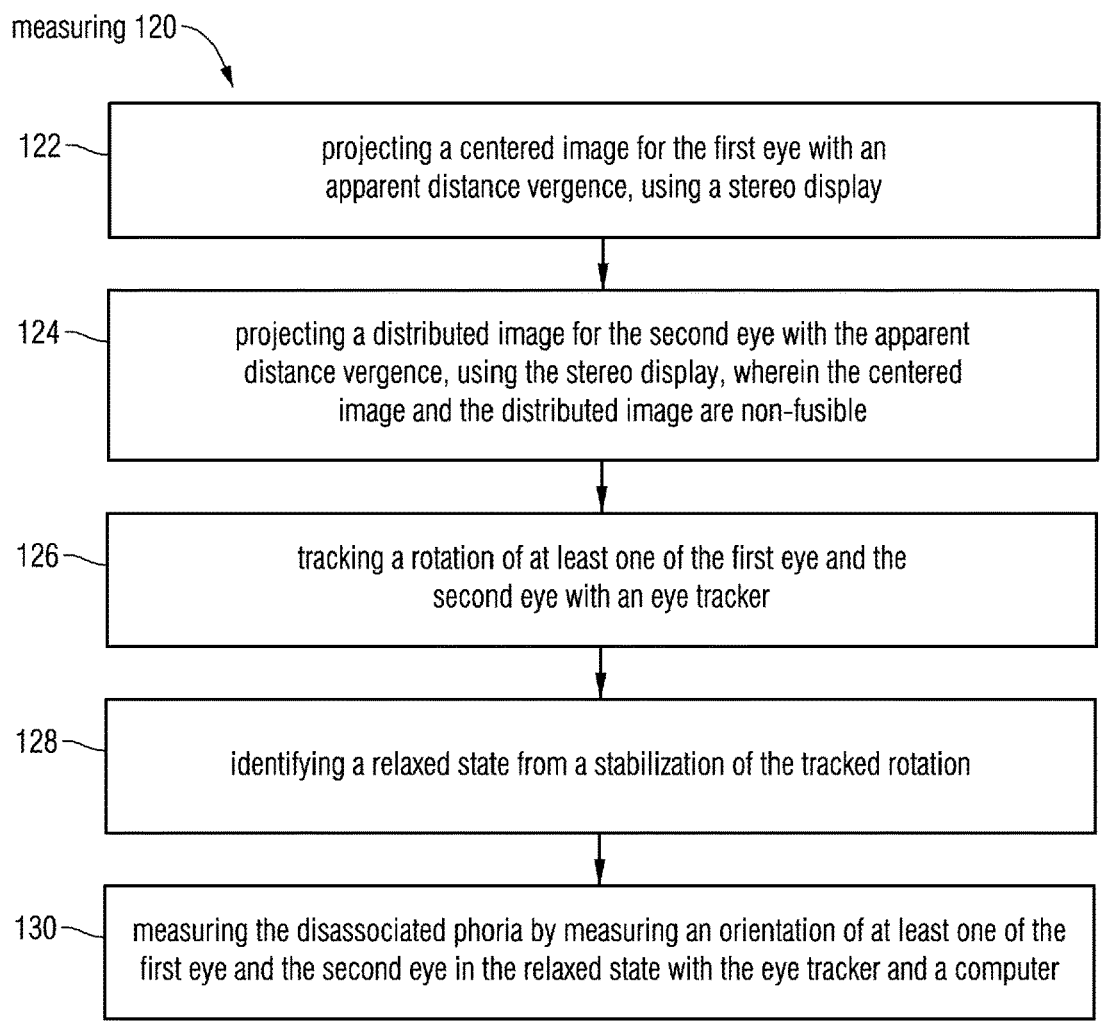
FIG. 12 illustrates exemplary details of the measuring step.

FIG. 12 describes implementations of these steps in more detail, and FIGS. 13A-D illustrate these steps in a particular embodiment. In these embodiments, the measuring 120 can include the followings.

Projecting 122 a centered image for the first eye with an apparent distance vergence, using a stereo display;
    projecting 124 a distributed image for the second eye with an apparent distance vergence, using the stereo display, wherein the centered image and the distributed image are non-fusible;
    tracking 126 a rotation of at least one of the first eye and the second eye using an eye tracker;
    identifying 128 a relaxed state from a stabilization of the tracked rotation; and measuring 130 the disassociated phoria by measuring an orientation of at least one of the first
eye and the second eye in the relaxed state using the eye tracker and a computer.

Figure 13A:
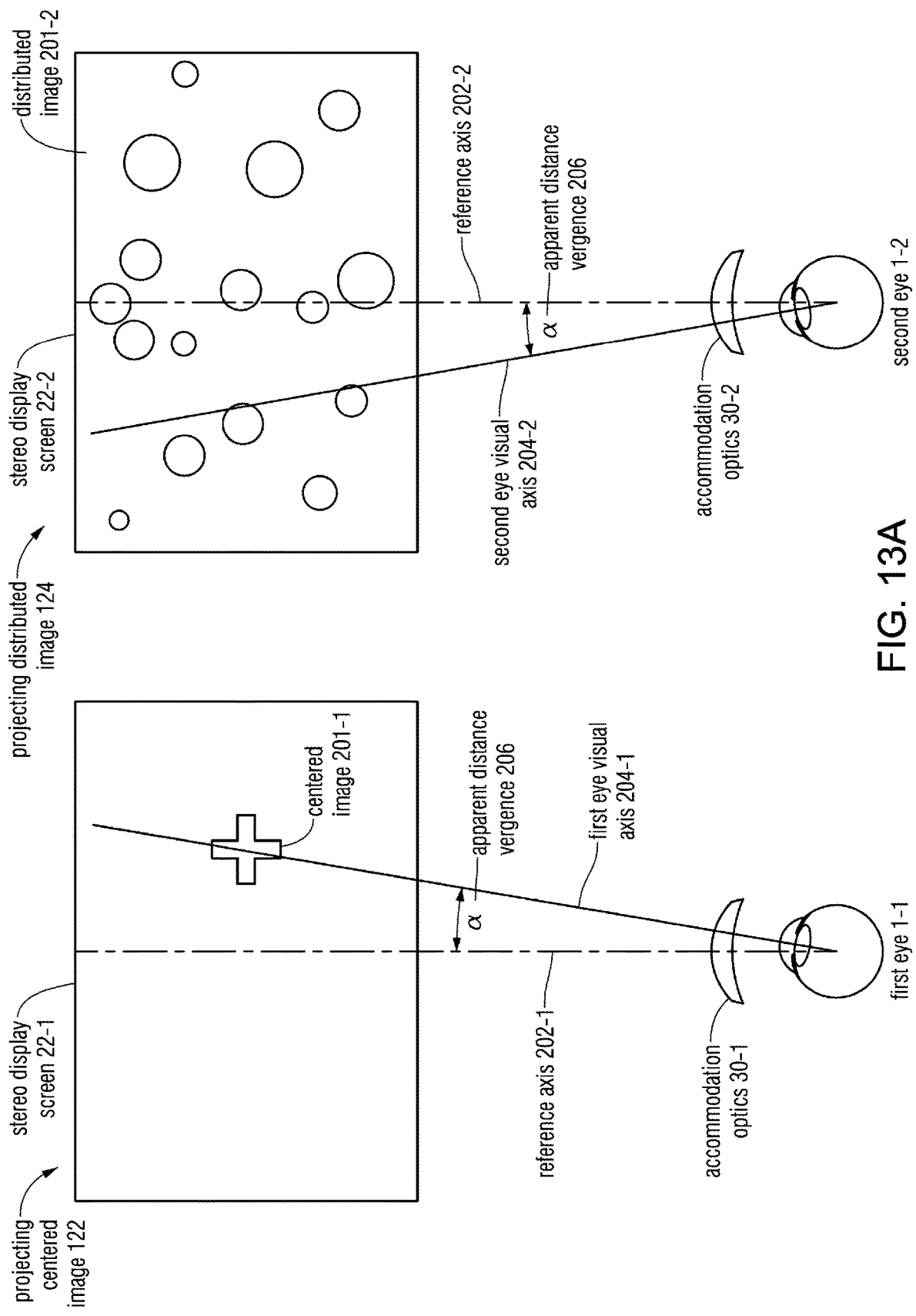
FIGS. 13A-D illustrate steps of carrying out the measuring step.

FIG. 13A, left panel illustrates that the projecting of a centered image step 122 can include projecting a centered image 201-1, a cross in this case, on the stereo display screen 22-1 of the stereo display 20 of the system 10. The projecting 122 can be done with an apparent distance vergence 206. A reference axis 202-1 is introduced for reference as a central normal that connects a center of the first eye 1-1 with a center of the stereo display screen 22-1. With this, the apparent distance vergence 206 can be characterized by an apparent distance vergence angle $\alpha=\alpha(L)$, the angle that a first eye visual axis 204-1 makes with the reference axis 202-1 when looking at an object that is placed halfway between the two eyes 1-1 and 1-2 at the apparent distance L. More generally, the apparent distance vergence 206 will be represented by and referred to as the line directed from a center of the first eye 1-1 with the angle $\alpha(L)$ relative to the reference axis 202-1, even if the first eye visual axis 204-1 is not pointing along this line.

The centered image 201-1 is centered in the sense that it is moved off the center of the stereo display screen 22-1 only by the apparent distance vergence angle $\alpha(L)$ to simulate the apparent distance vergence 206. For brevity's sake, sometimes this angle will be only referred to as the vergence angle $\alpha$. The definition of the first eye visual axis 204-1 can incorporate a lens or any other relevant portion of the accommodation optics 30-1, through which the first eye 1-1 is observing the centered image 201-1.

Figure 4C:
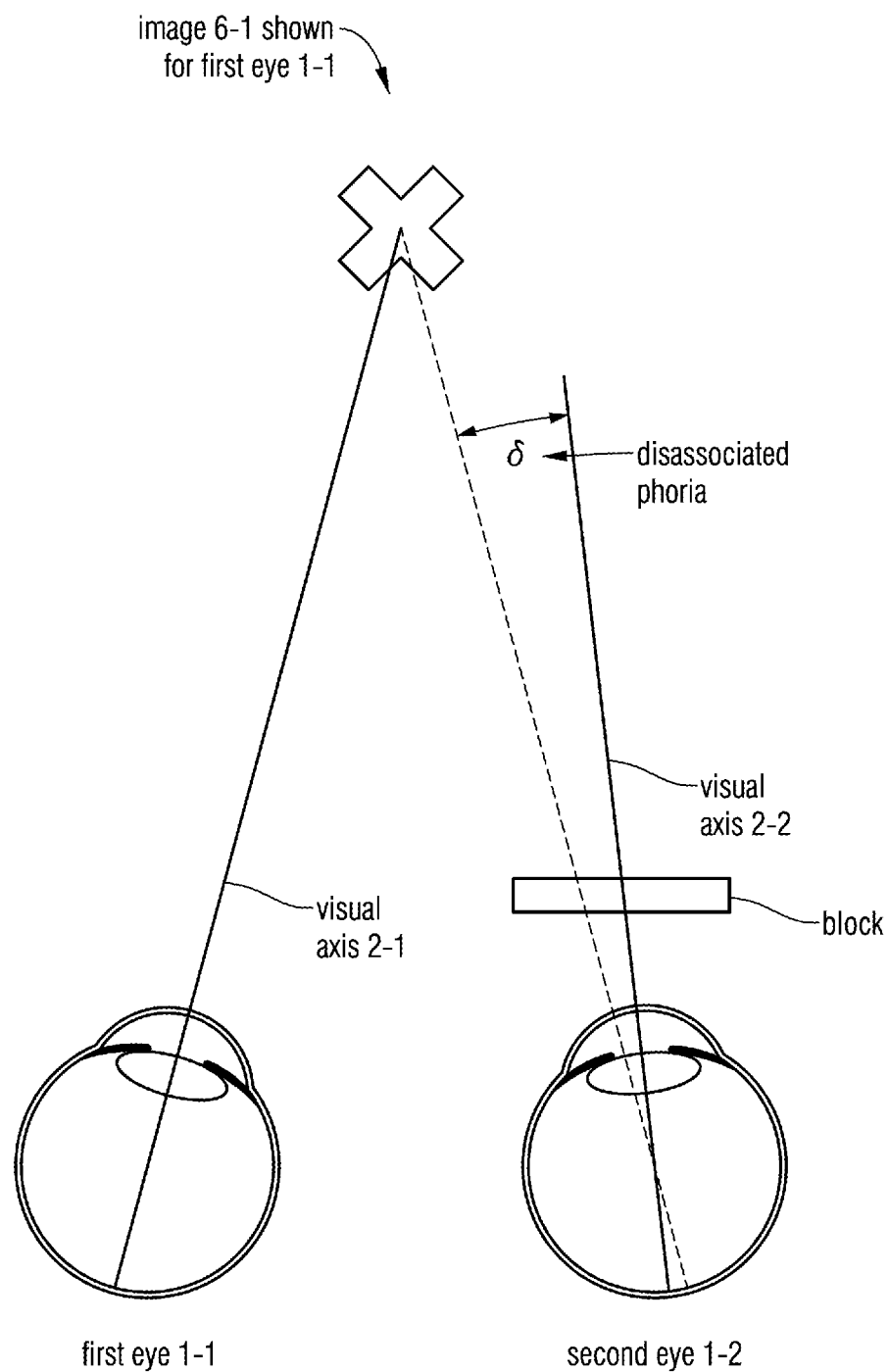

FIG. 13A, right panel illustrates the projecting of a distributed image step 124 for the second eye 1-2, in this case, a set of irregularly placed balls or spheres of random size and position, without an apparent center. The centered image 201-1 is an example of a dominant image, and the distributed image 201-2 is an example of a non-dominant image. The centered, dominant image 201-1 and the distributed, non-dominant image 201-2 are examples of non-fusible images. Alternatively, the stereo display screen 22-2 can be simply darkened as another embodiment of the non-fusible distributed image 201-2, instead of the irregularly placed balls, in analogy to the block in FIG. 4C.

Figure 13B:
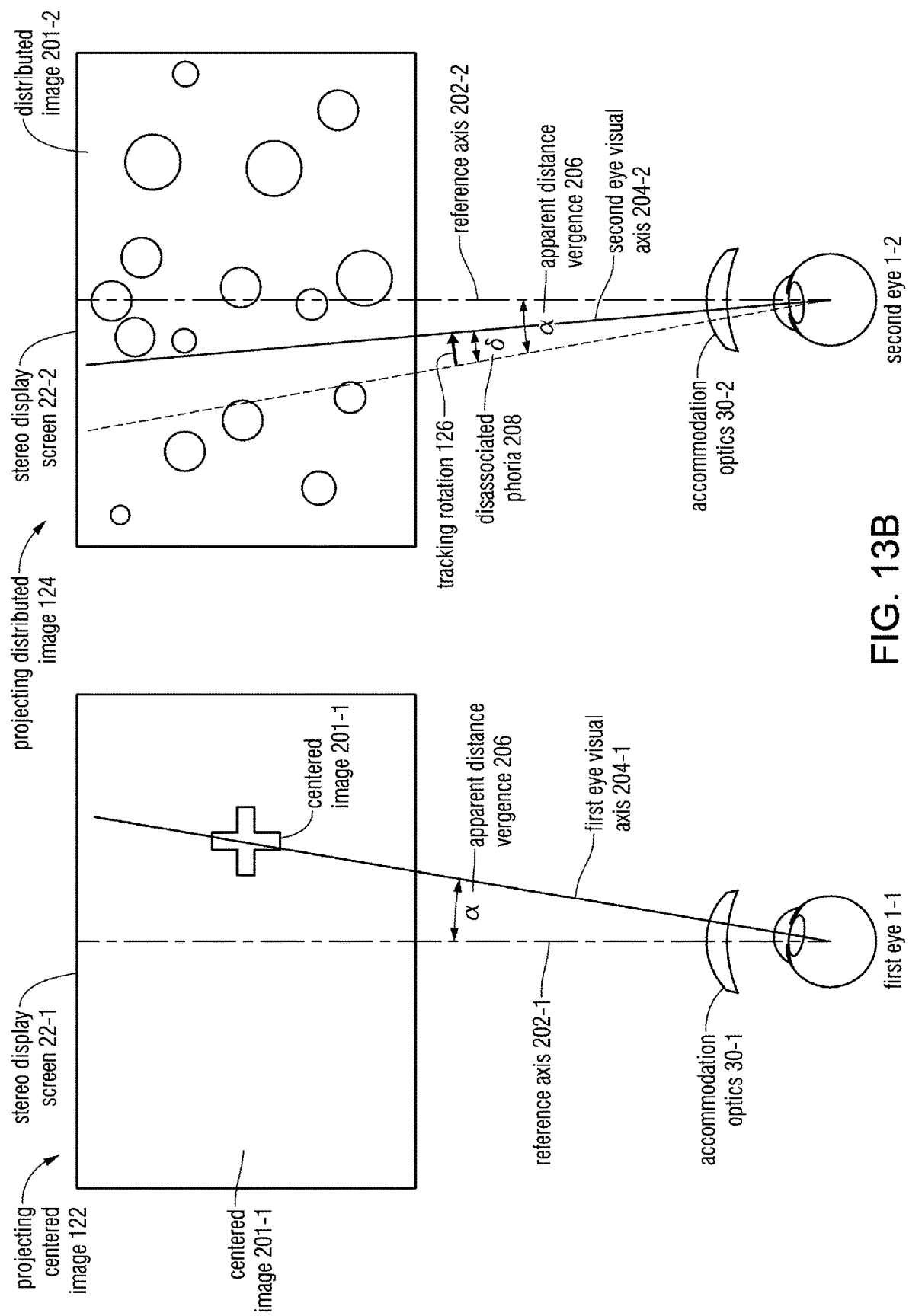

FIG. 13B illustrates that, as described earlier, the second eye 1-2 will initially also turn inward by approximately the same apparent distance vergence angle $\alpha$ as the first eye 1-1, but, after the brain fails to fuse the non-fusible central image 201-1 and distributed image 201-2, the second eye 1-2 wanders away. The eye tracker 40 can execute the tracking step 126 of the second eye 1-2 until the optometrist, or an automated program, determines that the wandering second eye 1-2 reached a relaxed state from a stabilization of the tracked rotation in the identifying step 128. This stabilization can be defined in various ways: from the eye coming to a stop, or an amplitude of the eye's jitter becoming less than a threshold, or a directional rotation of the eye evolving into a directionless wandering.

In the measuring step 130, once the relaxed state has been identified in step 128, the eye tracker 40 can measure the orientation of the relaxed second eye 1-2 by determining the angle S the second eye visual axis 204-2 with the apparent vergence 206. In this measuring step 130, 6 the angular deviation of the relaxed second eye 1-2 from the apparent distance vergence 206 will be referred to as the disassociated phoria 208, with its disassociated phoria angle $\delta$. This definition is in close analogy with that of FIGS. 4B-C. As mentioned before, small differences exist among various practitioner's definitions of the disassociated phoria.

In some related embodiments, the tracking step 126 may involve tracking a rotation of the first eye 1-1, the second eye 1-2, or both. In these embodiments, the disassociated phoria 208 can be defined from measuring 130 a first eye phoria angle $\delta$-1, a second eye phoria angle $\delta$-2, and determining the disassociated phoria S as some type of a mean of $\delta$-1 and $\delta$-2.

FIGS. 13A-B illustrated that the steps 122-130 of the overall measuring step 120 can be performed as a near vision distance, e.g. L being in the range of 40 cm-100 cm.

Figure 13C:
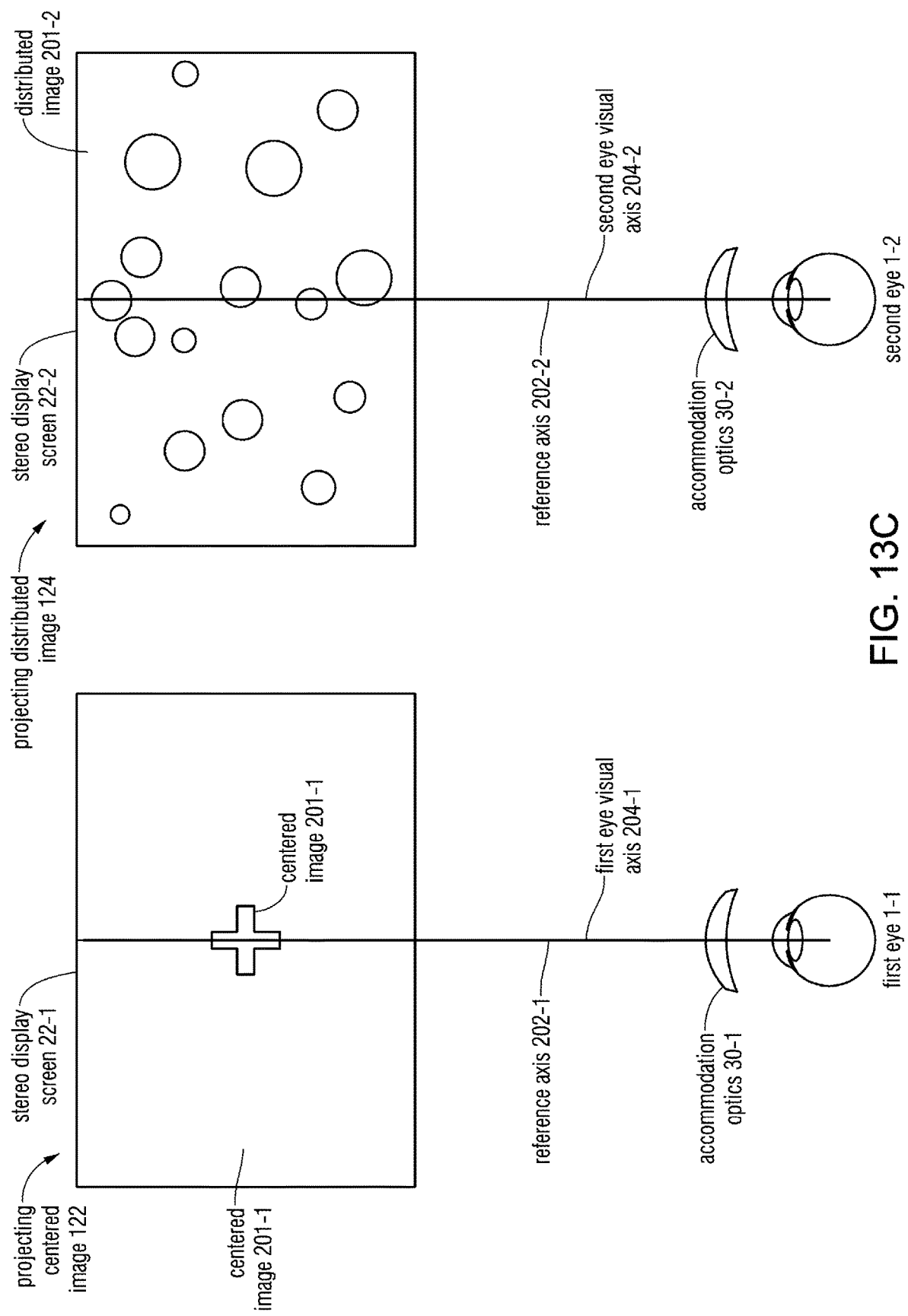
Figure 13D:
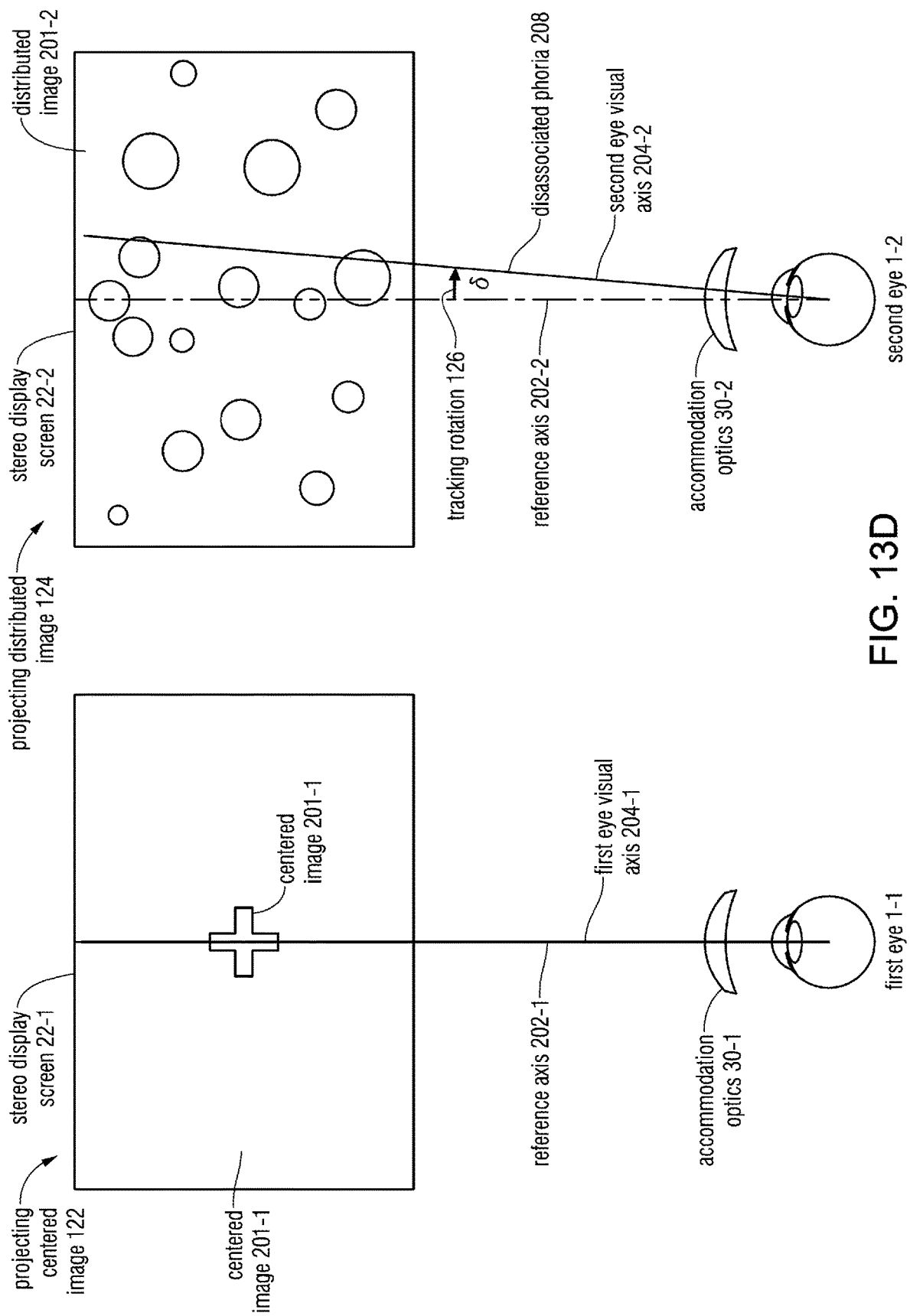

FIGS. 13C-D illustrate that the same steps 122-130 can be also performed as part of a distance vision test, when the apparent distance is L large, and the apparent distance vergence angle is $\alpha=0$. In related embodiments, L can be in the m-Om range. Expressed in diopters, the method 100 can be performed at near vision distances corresponding to 1-3D, at distance vision distances corresponding to 0-0.5 D.

To summarize, the result of the measuring step 120, the first stage of the method 100, is the disassociated phoria 208, with its disassociated phoria angle $\delta$. The second stage of the method 100, the determining step 140, carries out additional tests of the prismatic misalignment that build on the just determined disassociated phoria 208. Therefore, the overall method 100 is a combination of the first and second stages and thus the method 100 integrates two distinct tests of prismatic misalignments, and thus integrates knowledge and data about two different types of the binocular alignment. Doing so promises a qualitatively more complete treatment and a qualitatively better improvement of the visual acuity.

Figure 14:
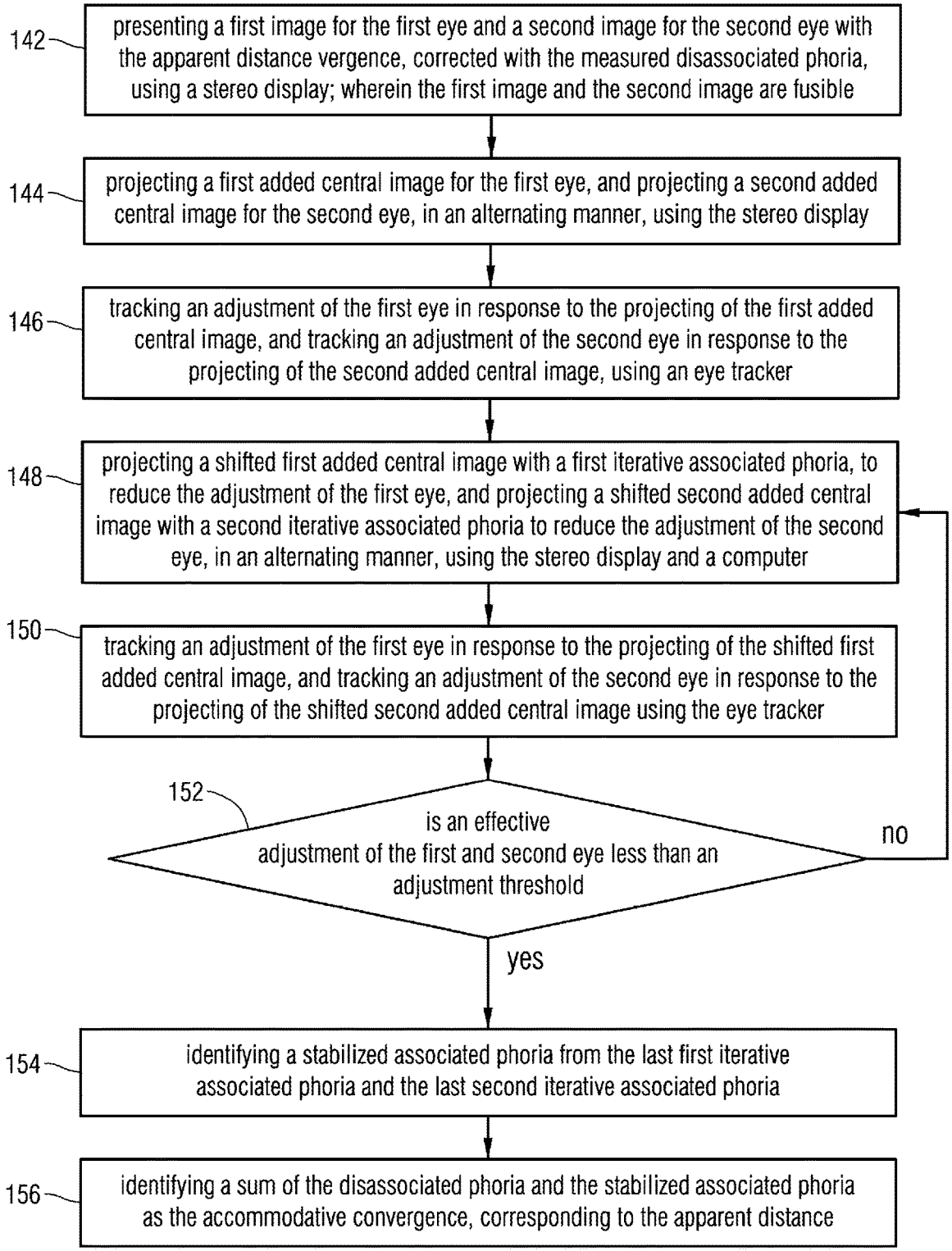
FIG. 14 illustrates exemplary details of the determining step.

FIG. 14 illustrates that the determining step 140 can include a presenting step 142 of a first image for the first eye and a second image for the second eye, with the apparent distance vergence, corrected with the measured disassociated phoria, using the stereo display; wherein the first image and the second image are fusible.

Figure 15A:
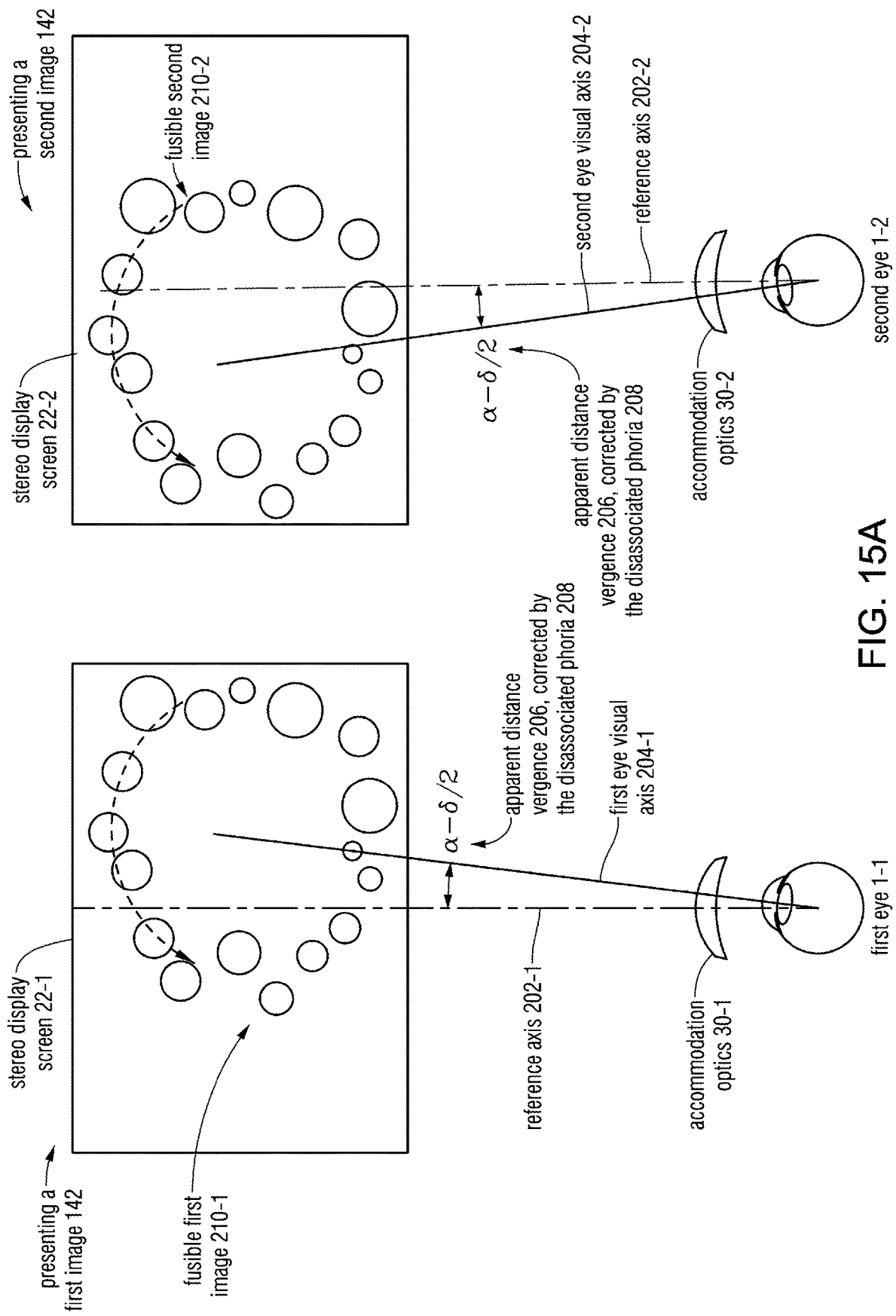
FIGS. 15A-C illustrate steps of carrying out the determining step.

FIG. 15A illustrates that in some implementations of the presenting step 142, a fusible first image 210-1 can be presented on the stereo display screen 22-1 for the first eye 1-1, and a fusible second image 210-2 can be presented on the stereo display screen 22-2 for the second eye 1-2. These fusible images 210-1 and 210-2 can be peripheral. For example, the peripheral images 210-1 and 210-2 can be two, essentially identical circular bands, or rings, of balls or planets, as shown. Centers of the fusible images 210-1 and 210-2 can be shifted towards each other according to the apparent distance vergence 206, the vergence angle $\alpha$ being corrected by the disassociated phoria $\delta$ (208), as measured in the measuring step 120. The measured disassociated phoria S can be symmetrically distributed as $\delta/2-\delta/2$ between the two eyes, as shown. In these typical cases, the centers of the fusible images 210-1 and 210-2 can be shifted towards each other according to $\alpha-\delta/2$, the vergence angle $\alpha$, corrected by the disassociated phoria $\delta$, relative to the reference axes 202-1 and 202-2. In response, the first eye visual axis 204-1 and the second eye visual axis 204-2 typically align with the apparent distance vergence 206, corrected by the disassociated phoria 208, as shown by these visual axes 204 pointing towards the centers of the fusible images 210.

In some cases, when the binocular misalignment of the two eyes is asymmetric, the optometrist may have reasons to attribute the measured disassociated phoria $\delta$ unevenly between the two eyes. It is also noted that the earlier convention is continued to make the description more comprehensible: the description will refer to a pair of "limitation N-1 and limitation N-2" simply as "limitations N", where doing so does not lead to confusion.

The shift of the fusible images 210 can be impacted by the accommodation optics 30. The settings of the accommodation optics 30 can depend on L, the accommodative distance, or a spectacle power preferred by the patient, possibly further corrected by a cylinder or aberration.

In some embodiments, the fusible first image 210-1 and the fusible second image 210-2 can be dynamic. In FIG. 15A, the directed dashed arcs indicate that the rings of planets can be rotating around their center. Experiments have shown that making the peripheral fusible images 210 rotate captures peripheral prismatic effects more reliably and reproducibly. In the presenting step 142 the radius, spatial distribution, coloring, dynamics, and speed of rotation of these fusible images 210 could all be adjusted to provide the alignment information with the optimal weight.

In some embodiments, the first image 210-1 and the second image 210-2 can be static. In some embodiments, the first image 210-1 and the second image 210-2 can be central. These embodiments may present their own medical advantages.

Figure 15B:
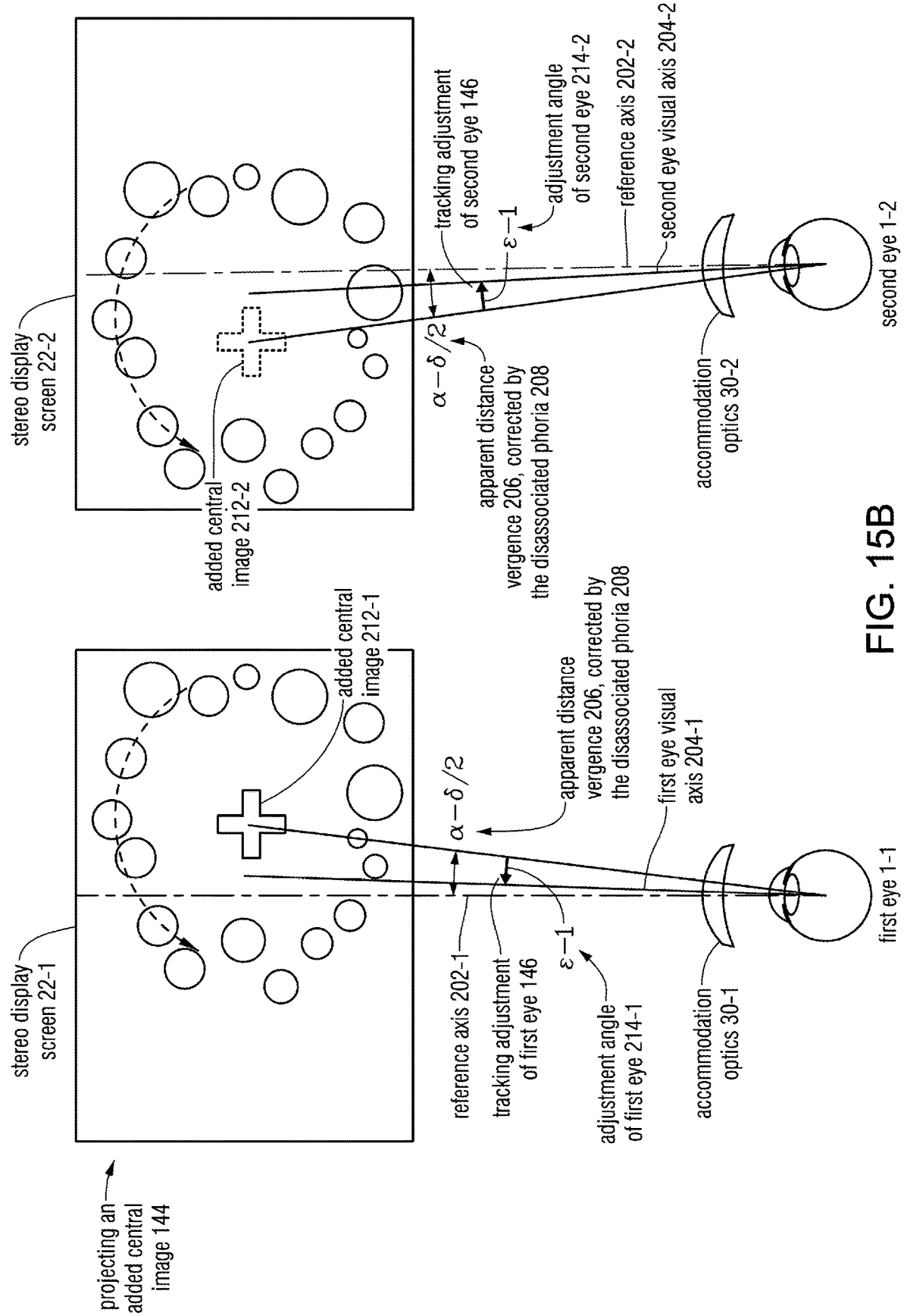

FIG. 14 describes and FIG. 15B illustrates that the presenting step 142 can be followed by a projecting step 144. The projecting step 144 can include a projecting of a first added central image 212-1 for the first eye 1-1, and a projecting a second added central image 212-2 for the second eye 1-2. These central images 212 can be projected at the center of the fusible images 210. In the embodiment of fusible images 210 being circulating planets, the added central images 212 can be projected at the center of their circulation, e.g., as a cross, as shown.

The projecting 144 of these two added central images 212-1 and 212-2 can be performed in an alternating manner, using the stereo display 20. To express the alternating manner of the projecting 144, only one of the added central images, the cross 212-1 is shown with a solid line, and the other added central image, 212-2 is shown with a dashed line in FIG. 15B. The period of the alternating can be selected according to several different criteria, and can be less than 1 second, in a range of 1-100 second, in some cases in a range of 5-10 seconds.

Had $\delta$, the angle of the disassociated phoria 208, measured in step 120, completely captured the binocular alignments of the eyes 1, then the eyes 1 would not have needed to adjust to the projecting step 144 of the added central images 212 with the vergence angle $\alpha$, corrected by the disassociated phoria angle $\delta/2$. This would have manifested itself in that the eye visual axes 204 would have had remained aligned with the vergence angle $\alpha$, corrected by the disassociated phoria angle $\delta/2$ after the projecting step 144.

However, Applicant's studies revealed that patients moved and adjusted their eyes 1 in response to the projecting 144 of the added central images 212 with the corrected vergence angle $\alpha$-$\delta/2$. This led Applicant to the recognition that additional measurements were necessary to determine the remaining, residual prismatic misalignment of the eyes. These additional measurements are described in steps 146-154, as follows.

Tracking 146 an adjustment of the first eye in response to the projecting of the first added central image, and tracking an adjustment of the second eye in response to the projecting of the second added central image, using an eye tracker.

projecting 148 a shifted first added central image with a first iterative associated phoria, to reduce the adjustment of the first eye, and projecting a shifted second added central image with a second iterative associated phoria, to reduce the adjustment of the second eye, in an alternating manner, using the stereo display and a computer;

tracking 150 an adjustment of the first eye in response to the projecting of the shifted first added central image, and tracking an adjustment of the second eye in response to the projecting of the shifted second added central image using the eye tracker;

determining 152 whether an effective adjustment of the first and second eye is less than an adjustment threshold, and returning to the projecting the shifted first added central image step if the effective adjustment of the first and second eye is greater than the adjustment threshold;

identifying 154 a stabilized associated phoria from the last first iterative associated phoria and the last second iterative associated phoria, if the effective adjustment of the first and second eye is less than the adjustment threshold; and identifying 156 a sum of the disassociated phoria and the stabilized associated phoria as a correction to the accommodative convergence, corresponding to the apparent distance. These steps are described in some detail next.

FIG. 14 describes and FIG. 15B illustrates that in order to determine residual prismatic misalignments, the projecting step 144 can be followed by the tracking 146 of an adjustment of the first eye 1-1 in response to the projecting of the first added central image 212-1, and tracking an adjustment of the second eye 1-2 in response to the projecting of the second added central image 212-2, using an eye tracker 40. FIG. 15B illustrates that the first eye 1-1 adjusts to the projecting 144 by rotating the first eye visual axis 204-1 with an adjustment angle of the first eye 214-1, denoted by $\epsilon$-1, and the second eye 1-2 adjusts by rotating the second eye visual axis 204-2 with an adjustment angle of the second eye 214-2, denoted by $\epsilon$-2. From now on, for brevity, the angles will be referenced to the apparent distance vergence corrected by the disassociated phoria, having the angle $\alpha$-$\delta/2$, instead of the reference axis 202. The fact that the adjustment angles $\epsilon$-1 and $\epsilon$-2 were found non-zero, necessitated the subsequent steps of the determining step 140.

Figure 15C:
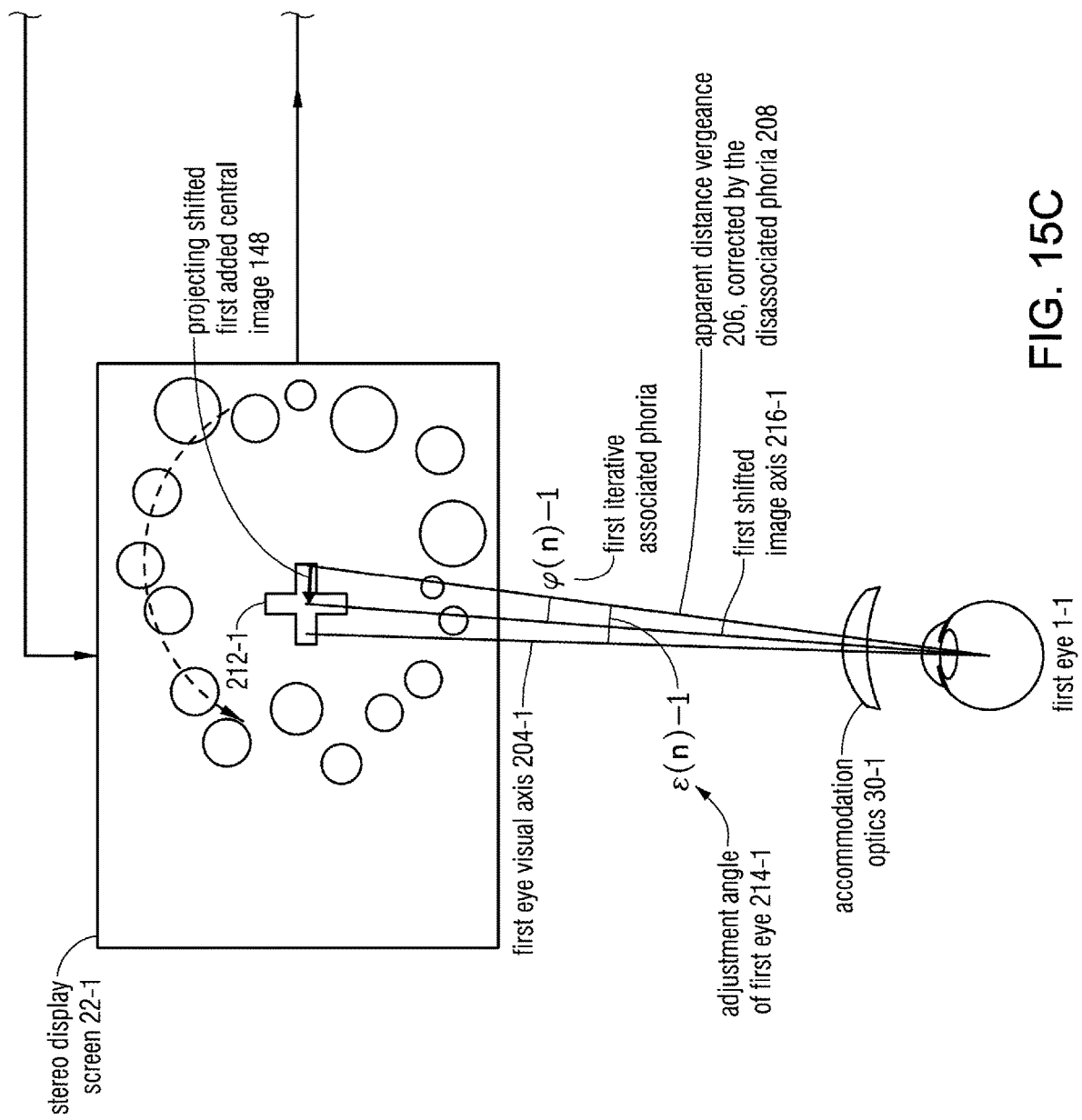
Figure 15C:
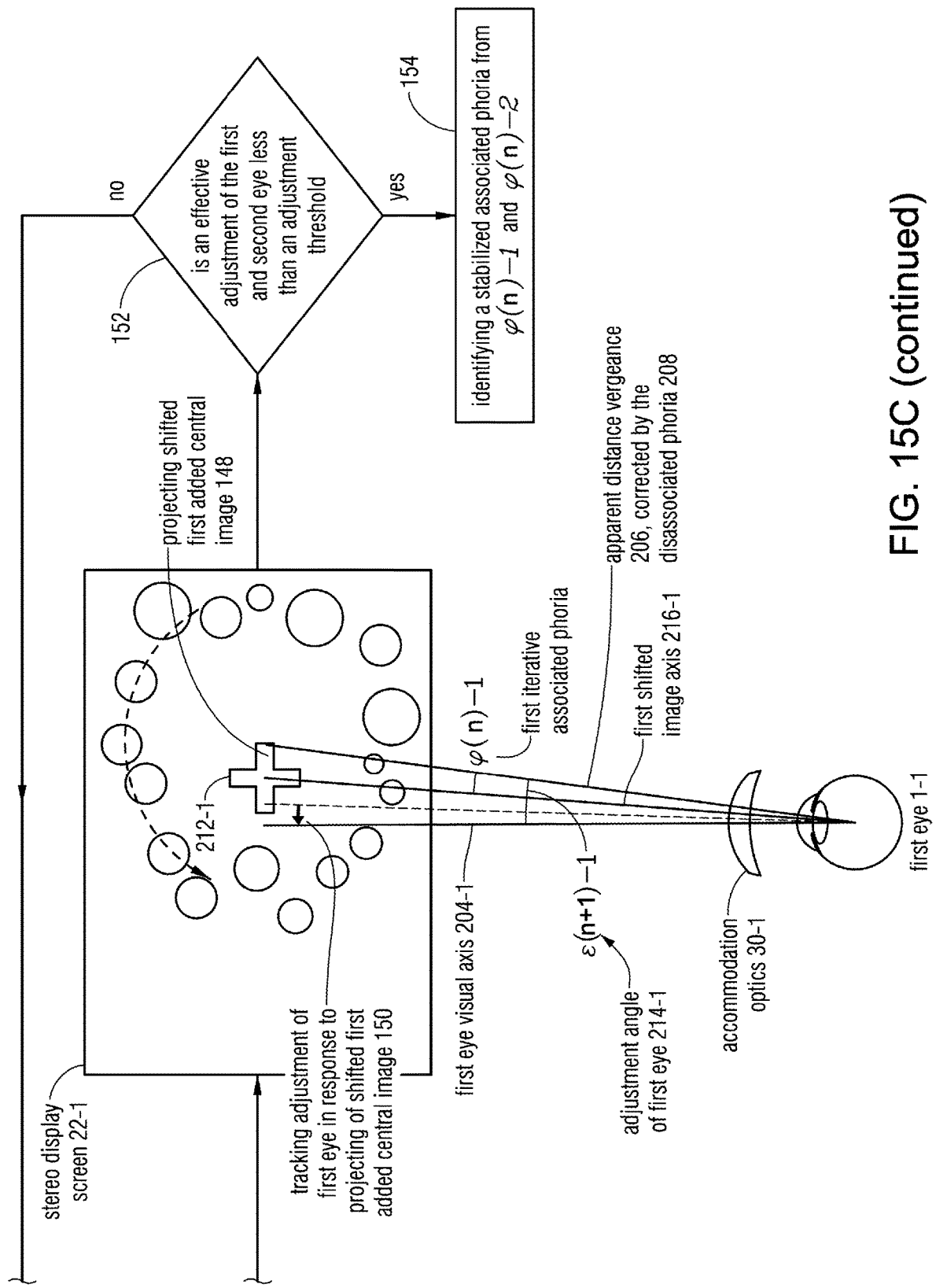

FIG. 15C shows that the determining the accommodative convergence step 140 next includes projecting 148 a shifted first added central image 212-1 with a first iterative associated phoria $\varphi(n)$-1, to reduce the adjustment of the first eye 1-1, and projecting a shifted second added central image 212-2 with a second iterative associated phoria $\varphi(n)$-2, to reduce the adjustment of the second eye 1-2. Here the adjustment of the eye can be measured by a change of the adjustment angle $\epsilon(n)$-1, as elaborated below.

For clarity and brevity, in this FIG. 15C only the first eye 1-1 is illustrated explicitly. The shifted added central images 212 are connected to the eyes 1 and characterized by shifted image axes 216. FIG. 15C shows the first shifted image axis 216-1, connecting the shifted first added central image 212-1 to the first eye 1-1.

Figure 3:
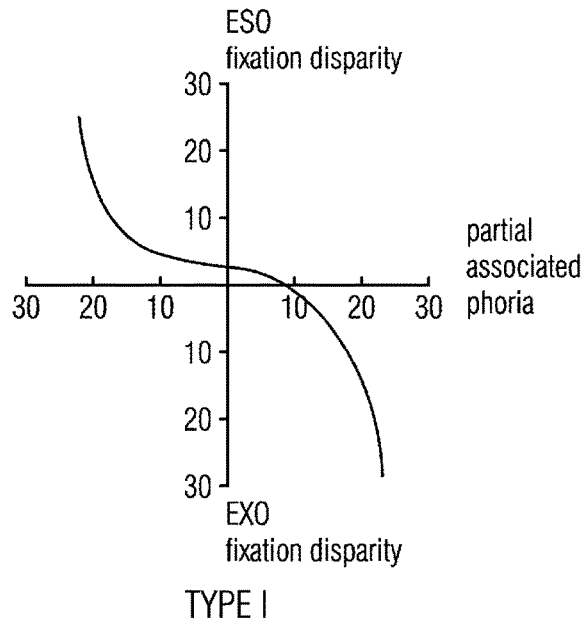
FIG. 3 illustrates four types of relationships between fixation disparity and partial associate phoria.
Figure 3:
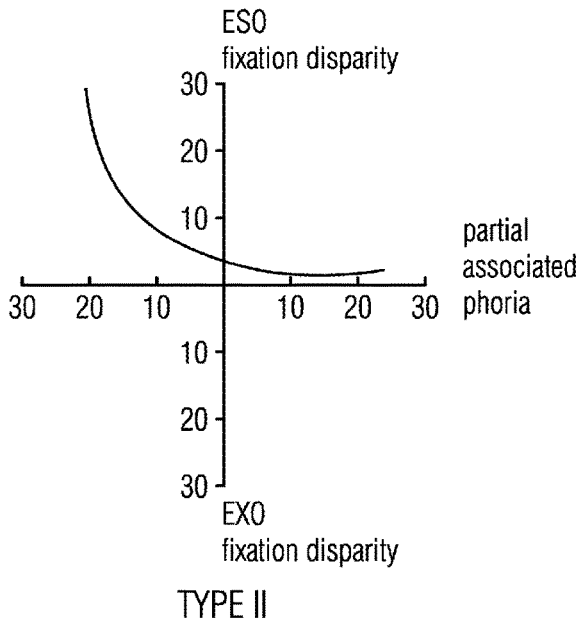
Figure 3:
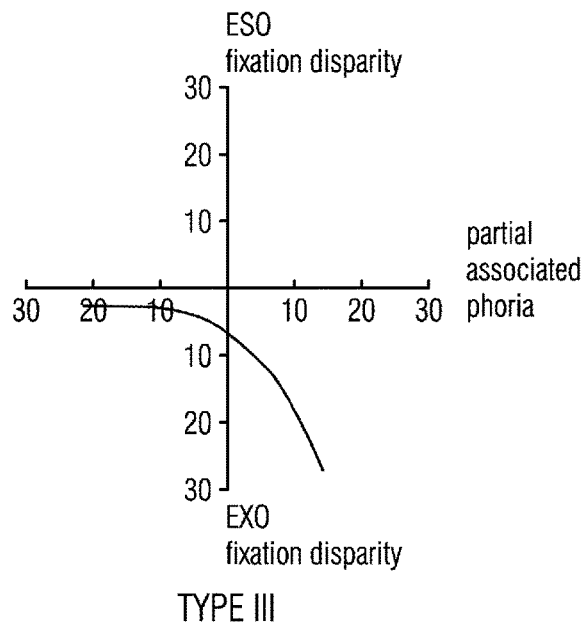
Figure 3:
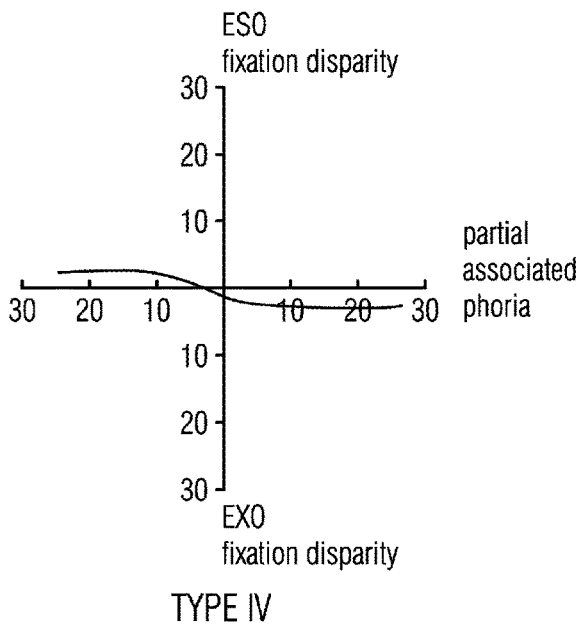

It was described in relation to FIGS. 2-3 that the fixation disparity $\gamma$ and the associated phoria $\gamma^*$, necessary to compensate it, are not simply equal and opposite to each other. In analogy to this recognition, the associated phoria $\varphi(n)$-1 is not simply equal and opposite to the adjustment angle of the first eye, $\epsilon(n)$-1. Therefore, embodiments of the method 100 determine these quantities iteratively, in steps 1, 2, . . . n. The step index is shown in the above definitions as $\varphi(n)$-1 and ε(n)-1: the first first iterative associated phoria is denoted with φ(1)-1, the first second iterative associated phoria by φ(1)-2, and so on. Naturally, the "-1" and "-2" indices continue to label the angles of the first eye 1-1 and the second eye 1-2, respectively, while the "(1)", "(2)", ... "(n)" indices label the first, second, and n-th steps of the iterative process.

As in the projecting step 144, the projecting 148 of these shifted added central images 212-1 and 212-2 can be performed in an alternating manner, using the stereo display 20 and the computer 50.

FIG. 15C further illustrates that the projecting step 148 can be followed by the tracking 150 of an adjustment of the first eye 1-1 in response to the projecting of the shifted first added central image 212-1, and tracking an adjustment of the second eye 1-2 in response to the projecting of the shifted second added central image 212-2, using the eye tracker 40. Specifying the presentation to the first eye 1-1 only, the tracking step 150 includes the tracking of the adjustment angle ε(n+)-1 of the first eye 1-1 in response to the projecting 148 of the shifted first added central image 212-1 with the first iterative associated phoria φ(n)-1.

This tracking step 150 is analogous to the tracking step 146. It is distinguished by the iterative step index having grown from (n) to (n+1). In simplified terms, embodiments of the method involve shifting the added central image 212 with the iterative associated phoria φ(n), tracking the responsive adjustment angle ε(n+1) of the eye 1, determining the adjustment of the eye 1 from the change of the adjustment angle ε(n+1)-ε(n), and then repeating the shifting of the added central image 212 with a new iterative associated phoria ε(n+1), selected in magnitude and sign to reduce the change of the adjustment angle ε(n+1)-ε(n).

In some embodiments, the magnitude of φ(n+1)-φ(n) can be chosen to be equal to ε(n+1)-ε(n): |φ(n+1)-φ(n)|=|ε(n+1)-ε(n)|. In some cases, these embodiments may exhibit a slow convergence. Therefore, in some embodiments, |φ(n+1)-φ(n)| can be chosen to be equal to λ|ε(n+1)-ε(n)|: |φ(n+1)-φ(n)|=λ|ε(n+1)-ε(n)|, where λ<1. These embodiments often exhibit good convergence. Other, non-linear, polynomial, non-analytic or analytic relationships can also be employed in various embodiments.

After performing these steps 148 and 150 iteratively, the determining step 152 can be performed to determine whether an effective adjustment of the first and second eye is less than an adjustment threshold. Using the above framework, the determining step 152 may evaluate whether the change of the adjustment angle |ε(n+1)-ε(n)|, is less than a threshold. The effective adjustment can be defined in various ways. It can involve the change of the adjustment angle of only one of the eyes: |ε(n+1)-ε(n)| for the eye 1-1; or the sum of the changes of the adjustment angles for both eyes 1-1 and 1-2, or some weighted average, or a non-linear relation.

If the change of the adjustment angle |ε(n+1)-ε(n)| is greater than a threshold, then the method can return to the projecting step 148 of the shifted first added central image 212, as shown in FIG. 15C.

On the other hand, if in step (n), the adjustment of the eye, as characterized by, e.g., the change of the adjustment angle |ε(n)-ε(n-1)|, is found to be less than the threshold, then the iteration can stop and the method can continue with the identifying 154 of a stabilized associated phoria φ from the last first iterative associated phoria φ(n)-1, and the last second iterative associated phoria φ(n)-2. Again, different formulas can be adopted to define the stabilized associated phoria φ this step 154, for example, φ=(φ(n)-1)+(φ(n)-2).

In the preceding embodiments, the disassociated phoria δ and the stabilized associated phoria φ were typically defined for the two eyes together. Thus, the per-eye values are half of the here-defined angles, in symmetrical cases.

The identifying step 154 can be followed by the identifying 156 of a sum of the disassociated phoria d and the stabilized associated phoria φ, (δ+φ), as a correction to the accommodative convergence AC, with the accommodative convergence angle α, that corresponds to the apparent distance. With this, the full, or fully corrected, accommodative convergence, determined by the method 100, can be expressed via the tangent of the corresponding full, or fully corrected, accommodative convergence angle: [α-(δ+φ)/2], in terms of prism diopters Δ. As mentioned earlier, a typical definition of the accommodative convergence is AC=100 tan [α-(δ-φ)/2], in prism diopters Δ. This form shows one of the ways the result of embodiments of the method 100 is a distinct step forward compared to previous methods, where only the disassociated phoria δ was used to correct a, translating into AC=100 tan [α-δ/2]. Another difference compared to previous methods is the particular system 10 and method 100, by which δ was determined.

With the fully corrected AC having been determined by the method 100, the binocular alignment can be again characterized by the AC/A ratio, the ratio of the accommodative convergence AC to the accommodative response A, to characterize the binocular alignment. This AC/A ratio can be determined for a single distance, or can be formed from AC and A values for multiple distances. For brevity, from here on, the fully corrected accommodative convergence AC will be simply referred to as accommodative convergence AC.

In some embodiments, the method 100 can include determining a distance vision accommodative convergence $AC(L_d)$ as an accommodative convergence resulting from performing the method 100 at a distance vision apparent distance $L_d$; and determining a near vision accommodative convergence $AC(L_n)$ as an accommodative convergence resulting from performing the method at a near vision apparent distance $L_n$.

With this preparation, in some embodiments, the binocular alignment of the first eye and the second eye can be characterized by first determining a distance vision accommodative response $A(L_d)$ and a near vision accommodative response $A(L_n)$, in diopters; and then by constructing a ratio of the distance vision accommodative convergence $AC(L_d)$ minus the near vision accommodative convergence $AC(L_d)$, divided by the distance vision accommodative response $A(L_d)$ minus the near vision accommodative response $A(L_n)$, to characterize the binocular alignment of the first eye and the second eye:

$$\text{binocular alignment} = [AC(L_d) - AC(L_n)] / [A(L_d) - A(L_n)] \quad (1)$$

In some embodiments, the measuring 120 at the apparent distance and the determining 140 at the apparent distance can be performed using the accommodation optics 30.

When the drawbacks of existing methods were described earlier, the subjectivity of the patient's feedback has been identified as one source of scatter in the data, and reason for limited reproducibility. In this context, it is mentioned that embodiments of the method 100 can be performed without soliciting a substantive response from the patient to determine one of the key quantities or angles. (Of course, non-substantive responses about, e.g., comfort, can very well be part of the method 100.) This is one of the keys why the method 100 delivers measurements with high reproducibility.

Figure 16:
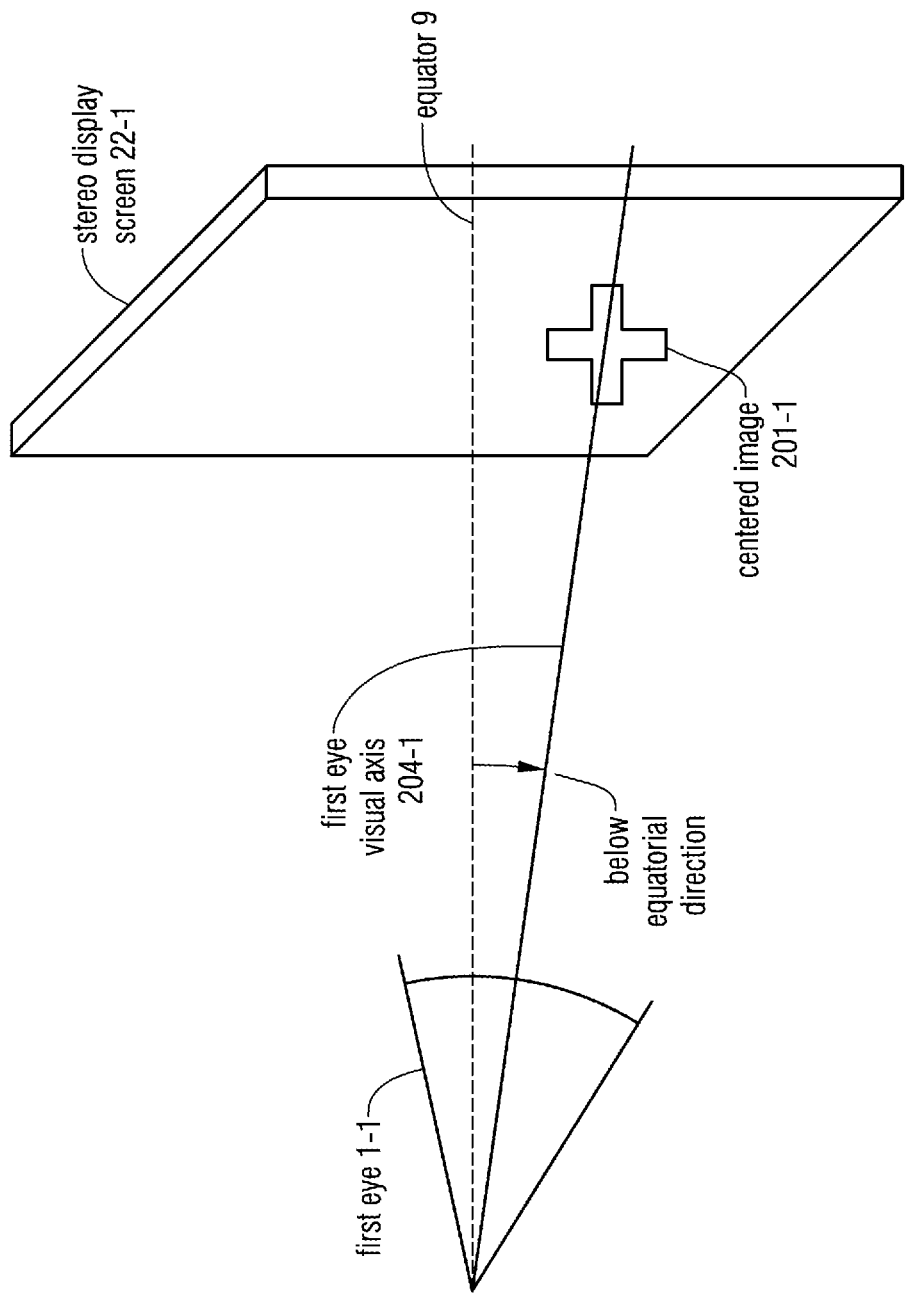
FIG. 16 illustrates a below-the-equator embodiment of the method for determining a binocular misalignment.

FIG. 16 illustrates that in some embodiments, when the method 100 is performed at apparent distances corresponding to near vision, the disassociated phoria and the accommodative convergence corresponding to the near vision can be determined at viewing angles below an equatorial direction 9 by displaying the centered images 201 below the equatorial direction 9.

Applicant's extensive experimentation demonstrated that when prismatic eye glasses were manufactured based on the accommodative convergence determined by the method 100, the patients wearing these glasses reported particularly promising reduction of digital-device related visual discomforts, pains and migraines.

It is quite likely that this substantial improvement has been achieved, among others, because the method 100 developed and integrated solutions regarding the points (1)-(5) identified earlier as follows.

(1) The method 100 does not use the patient's subjective responses as key inputs.
(2) The method 100 uses both peripheral images, e.g. the images 124 and 210, and central images, e.g. the images 201 and 212.
(3) The method 100 uses a two-stage method with the measuring step 120 and the determining step 140, gathering and utilizing information about both central vision and peripheral vision.
(4) The method 100 uses moving test images, e.g. the images 210.
(5) The method 100 developed a particular definition of the accommodative convergence and the protocol for its determination, e.g. in steps 142-156, and proved with extensive testing that eye glasses prescribed using this definition reduce eye-strain related discomfort particularly efficiently.

For all these reasons, the above described system 10 and method 100 offer promising new ways to reduce eye-strain related discomfort, pain and migraines.

FIGS. 17-25 illustrate an additional embodiment of a system for determining binocular alignment 310 that shows analogies to the embodiments of the system for determining binocular alignment 10 in FIGS. 8A-B. Accordingly, analogous parts are labeled with the same labels, with 300 as the base. As an example, the system for determining binocular alignment 310 can be thought of as an embodiment of the system for determining binocular alignment 10, and thus the various elements and techniques described in relation to system 10 can be applied, adapted and combined with those of the system 310, and vice versa. For brevity, the system for determining binocular alignment 310 will be sometimes simply referred to as the system 310.

Figure 17:
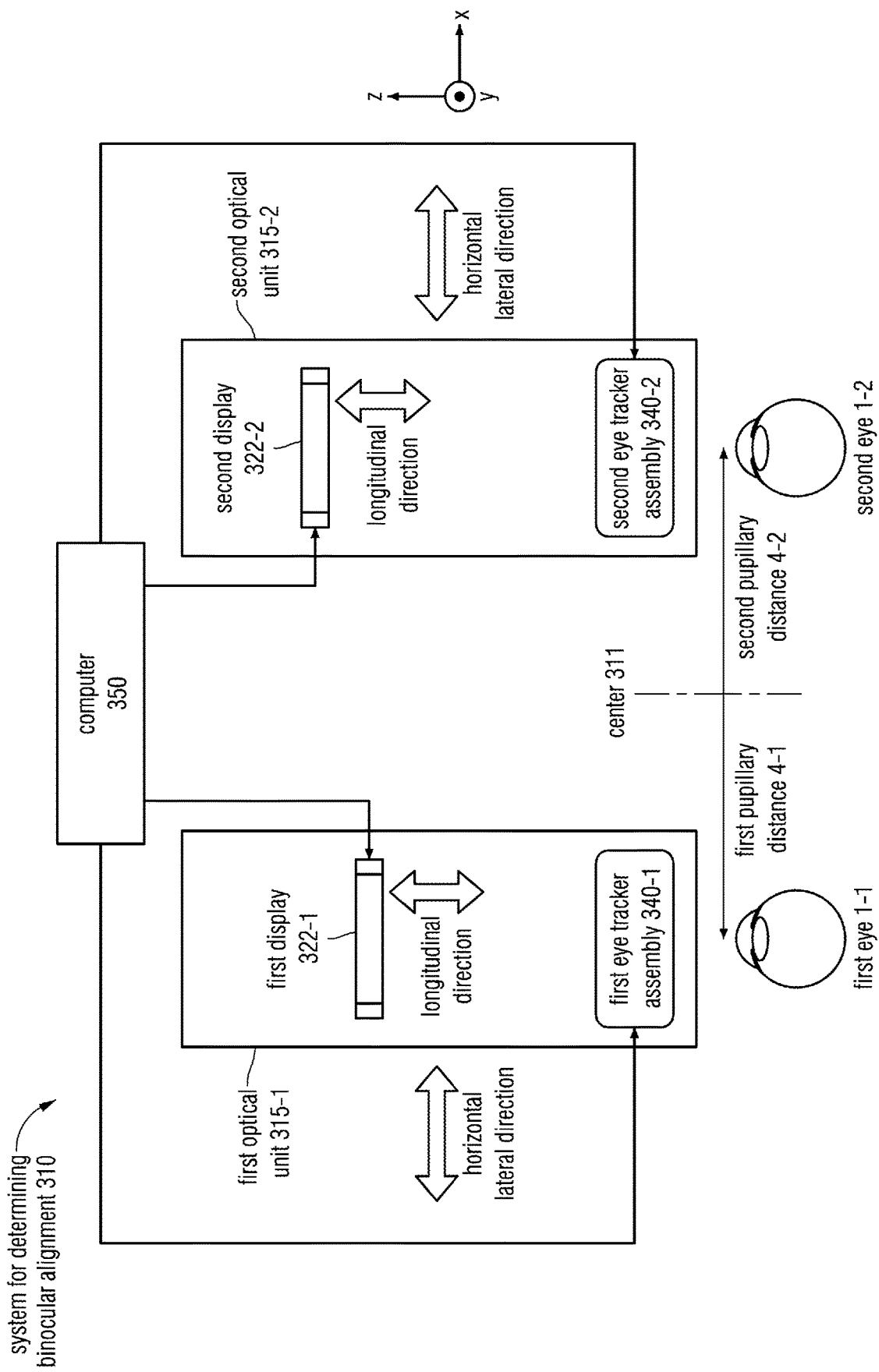
FIG. 17 illustrates a system for determining binocular alignment.

FIG. 17 illustrates a system to determine a binocular alignment 310 that comprises a first optical unit 315-1 that includes a first display 322-1, to display images for the first eye 1-1, actuatable along a longitudinal direction according to a simulated distance and an optical power of the first eye 1-1, and a first eye tracker assembly 340-1, to track a gaze direction of the first eye 1-1, adjustable in a horizontal lateral direction to accommodate a first pupillary distance 4-1 of the first eye; and a second optical unit 315-2, including a second display 322-2, to display images for the second eye 1-2, actuatable along the longitudinal direction according to a simulated distance and an optical power of the second eye 1-2, and a second eye tracker assembly 340-2, to track a gaze direction of the second eye 1-2, adjustable in the horizontal lateral direction to accommodate a pupillary distance 4-2 of the second eye 1-2; and a computer 350, coupled to the first optical unit 315-1 and the second optical unit 315-2, to determine a binocular alignment based on the gaze directions of the first eye 1-1 and the second eye 1-2. FIG. 17 also shows an xyz coordinate system on the side for an alternative way to characterize directions. Using this xyz coordinate system, the "horizontal lateral direction" is aligned with the x axis, a "vertical lateral direction" is aligned with the y axis, and the "longitudinal direction" is aligned with the z axis. This alignment can be strict, or in some embodiments it can be within a tolerance range, such as plus minus 10 degrees.

Different patients have different prescriptions, such as a few diopters of myopia or hyperopia. Some previously described embodiments of the system for determining binocular alignment 10 use phoropter wheels 32-1 and 32-2 with lenses of differing diopters to simulate these prescriptions, while displaying images for the patients with fixed stereo display screens 22-1 and 22-2—see, e.g., FIGS. 8A-B. These embodiments measure the binocular alignment at two different nominal distances. These distances are yet again simulated by rotating the phoropter wheels 32-1 and 32-2 and engaging lenses with diopters representing the simulated distances in addition to the patient's prescription.

Embodiments of the system for determining binocular alignment 310 do not involve phoropter wheels 32-1 and 32-2: they perform both of the above functions by having made the displays 322-1 and 322-2 actuatable along the longitudinal direction according to the simulated distance and the optical power of the eyes 1-1 and 1-2. The elimination of the phoropter wheels 32-1 and 32-2 makes the physical size of the system for determining binocular alignment 310 notably smaller than that of the system for determining binocular alignment 10 which uses phoropter wheels 32-1 and 32-2. This is an advantage in an optometrist's crowded office where physical space is at a premium. Further, using phoropter wheels 32-1 and 32-2 enables the system for determining binocular alignment 10 to simulate the patient's prescription only in discrete steps, such as in 1 diopter steps. As a further advantage, the system for determining binocular alignment 310 can actuate the first and second displays 322-1 and 322-2 essentially continuously along the longitudinal direction, and thus can simulate the patient's prescriptions continuously with high accuracy, possibly within 0.1 diopter or better.

Another challenge of the systems 10 that use the phoropter wheel 32-1 design is that when the phoropter wheel 32-1 is rotated to engage a new lens to simulate a new distance or new prescription, since the first eye tracker assembly 340-1 is seeing the eye 1-1 through the lenses of the phoropter wheel 32-1, the magnification changes with the rotation of the phoropter wheel 32-1. This change in the magnification necessitates the recalibration of the image analysis performed by the computer 350. This recalibration can lead to time lag and potentially coding challenges. In contrast, embodiments of the system for determining binocular alignment 310 that use actuatable first and second displays 322-1 and 322-2 avoid this need for recalibration, making the operation of the system 310 much easier.

In some embodiments, the first display 322-1 and the second display 322-2 can travel over a longitudinal range in the 50-200 mm range, in some embodiments, in the 75-125 mm range. The closest longitudinal distance of the first and second displays 322-1 and 322-2 to the first and second eye tracker assemblies 340-1 and 340-2 can be in the 5-40 mm range, in others, in the 10-30 mm range. As such, in some embodiments, the system for determining binocular alignment 310 can simulate prescription optical powers in a range of −20 D to +20 D, or less, in others in a range of −1 OD to +10 D, or less, in yet other embodiments in an asymmetric range, such as −10 to +20 D, or less.

In embodiments, the closer the first and second displays 322-1 and 322-2 are positioned to the eyes 1-1 and 1-2, the larger field of view is perceived by the patient. This field of view can extend at least from −30 degrees to +30 degrees, in others at least from −35 degrees to +35 degrees to even larger values. Accordingly, some embodiments of the system for determining binocular alignment 310 can be also used for visual field tests that have multiple utilities, such as identifying local blind spots, or scotomas, as well as issues with peripheral vision. These symptoms can be indicative of various ailments, such as glaucoma or brain disorders.

There are multiple benefits of making at least parts of the first and second optical units 315-1 and 315-2 adjustable in a lateral direction, and multiple embodiments to achieve this adjustability. As mentioned above, accommodating the different pupillary distances of different patients can be achieved with making the first and second eye tracker assemblies 340-1 and 340-2 adjustable in the horizontal lateral, "x" direction. Further, in systems where the first and second optical units 315-1 and 315-2 are fixed, when a patient is prompted to look at a simulated near object, the eyes are looking through the frontal lenses of the system(see e.g. first lens assembly 360-1 in FIG. 18) through a nasally offset off-center region. While these frontal lenses provide the designed refractive power, their off-center regions also introduce an unintended prism into the refraction of the light that perturbs the proper determination of the binocular alignment of the patient. Embodiments of the system for determining binocular alignment 310 minimize or even eliminate this problem again by making the first and second eye tracker assemblies 340-1 and 340-2, together with their corresponding frontal lenses, horizontally laterally actuatable. In theses systems 310, when a nearer object is simulated by displaying images for the first and second eyes 1- and 1-2 shifted closer to the center of the system 310, the first and second eye tracker assemblies 340-1 and 340-2, together with their frontal lenses, can be horizontally laterally actuated so that the patient is still looking at the nearer objects through a center of the frontal lens of the system to determine a binocular alignment 310, thereby avoiding the unintended prismatic effect.

The above motivations to introduce horizontal lateral adjustability can be achieved not only by making the first and second eye tracker assemblies 340-1 and 340-2 adjustable, or actuatable, along the horizontal lateral direction. To begin with, the first and second eye tracker assemblies 340-1 and 340-2 can be adjustable together with their corresponding frontal lenses, as just mentioned. Further, in some embodiments of the system for determining binocular alignment 310, the first display 322-1 can be also structurally adjustable, or actuatable, together with the first eye tracker assembly 340-1; and the second display 322-2 can be also structurally adjustable, or actuatable, together with the second eye tracker assembly 340-2. When accounting for the adjustability of the frontal lenses as well, in these embodiments, the entire first optical unit 315-1 and the second optical unit 315-2 can be horizontally adjustable, or actuatable, as shown in FIG. 17.

Yet another adjustability can be useful as well. Remarkably, there is a notable spread within the population regarding the vertical positions of the left and right eyes: the two eyes are often misaligned vertically by a few millimeters. Such patients can experience problems with aligning their eyes with the first and second optical units 315-1 and 315-2. Embodiments of the system to determine a binocular alignment 310 can manage this problem by having the first eye tracker assembly 340-1, with its frontal lenses, to be adjustable in a vertical lateral direction; and the second eye tracker assembly 340-2, with its frontal lenses, to be adjustable in the vertical lateral direction. With the language of the previously defined coordinate system, this translates to the adjustability along the y axis.

Figure 18A:
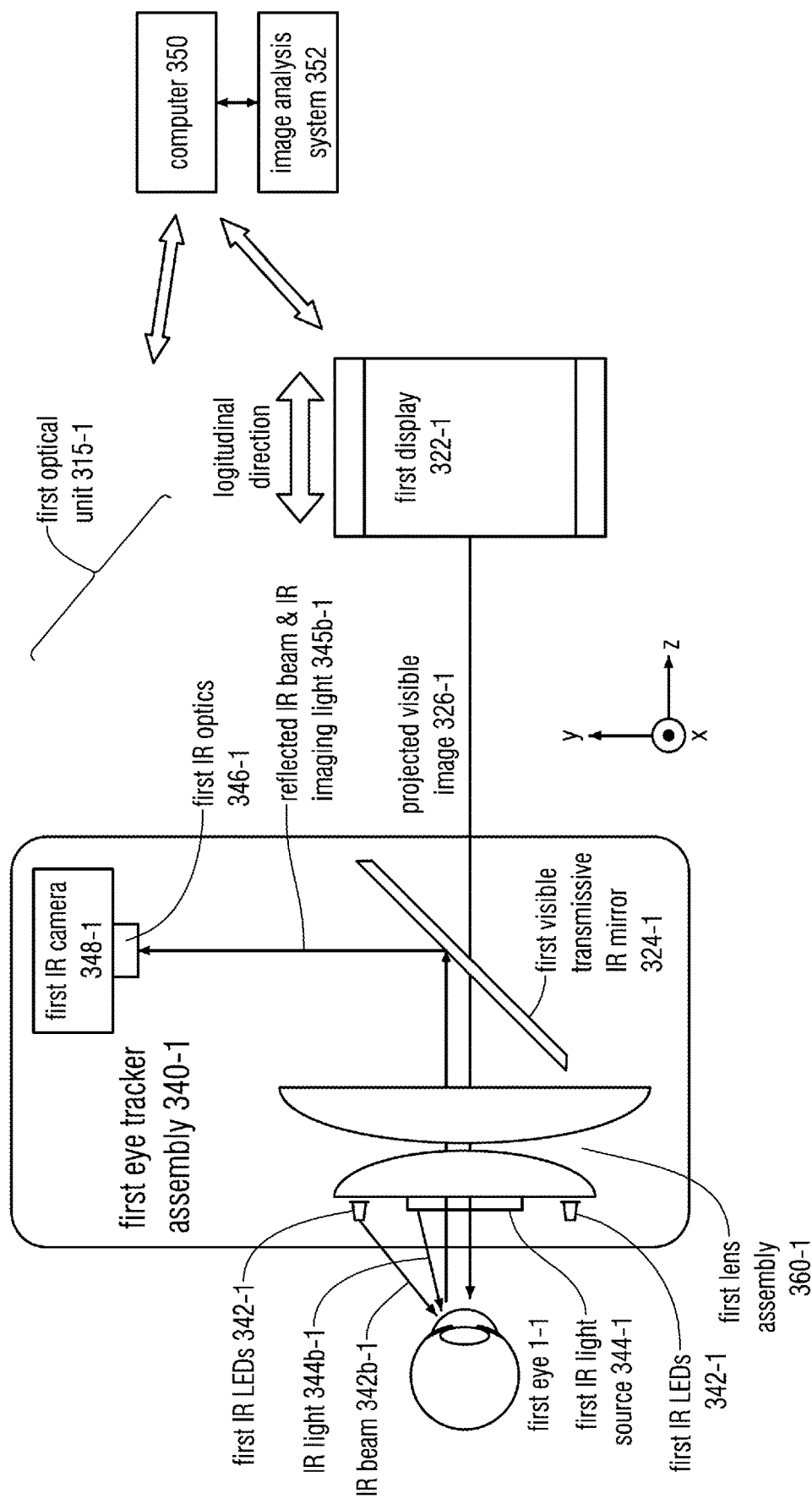
FIGS. 18A-B illustrate embodiments of a first optical unit.

FIG. 18A illustrates that in some embodiments of the system for determining binocular alignment 310, within the first optical unit 315-1, the first eye tracker assembly 340-1 can include one or more first infrared light emitting diodes (IR LEDs) 342-1, to project an infrared (IR) eye-tracking beam 342$b$-1 on the first eye 1-1. Further, the first eye tracker assembly 340-1 can also include a first infrared (IR) light source 344-1, to illuminate the first eye 1-1 with an infrared (IR) imaging light 344$b$-1. Finally, the first eye tracker assembly 340-1 can include a first infrared (IR) camera 348-1, to detect the IR eye-tracking beam 342$b$-1 after reflection from the first eye 1-1, and the IR imaging light 344$b$-after reflection from the first eye 1-1, collectively labeled reflected IR beam and IR light 345$b$-1, through a first infrared (IR) optics 346-1. Naturally, in the system for determining binocular alignment 310, within the second optical unit 315-2, the second eye tracker assembly 340-2 can include one or more second infrared (IR) light emitting diodes 342-2, to project an infrared (1R) eye-tracking beam 342$b$-2 on the second eye 1-2, a second infrared (IR) light source 344-2, to illuminate the second eye 1-2 with an infrared imaging light 344$b$-2, and a second infrared (IR) camera 348-2, to detect the IR eye-tracking beam 342$b$-2 after reflection from the eye 1-2, and the IR imaging light 344$b$-2, after reflection from the second eye 1-2, collectively labeled reflected IR beam and IR light 345$b$-2, through a second 1R optics 346-2. Since the second eye tracker assembly 340-2 is analogous to the first eye tracker assembly 340-1, there is no need to show it expressly. For orientation, the xyz coordinate system of FIG. 17 is also shown, from a perspective rotated relative to that of FIG. 17.

In embodiments, the number of the first and second IR LEDs 342-1 and 342-2 can be in the range of 1-10, in some embodiments in the range of 2-4. In embodiments, the first infrared light source 344-1 can include a set of individual infrared light emitting diodes, spatially distributed in order to illuminate the first eye 1-1 with a dispersed infrared imaging light 344$b$-1; and the second infrared light source 344-2 can include a set of individual infrared light emitting diodes, spatially distributed in order to illuminate the second eye 1-2 with a dispersed infrared imaging light 344$b$-2. The individual infrared diodes of the first and second infrared light source 344-1 and 344-2 can be positioned in many different patterns, such as a circle, an arc, a rectangle, and a rectangular array, among others. Their number can be in the range of 1-50, in some embodiments in the range of 5-20. The infrared imaging lights 344$b$-1 and 344$b$-2 can be dispersed, or homogenized in different ways, including by a diffuser, or by a scattering mirror, or by a scattering surface.

Figure 18B:
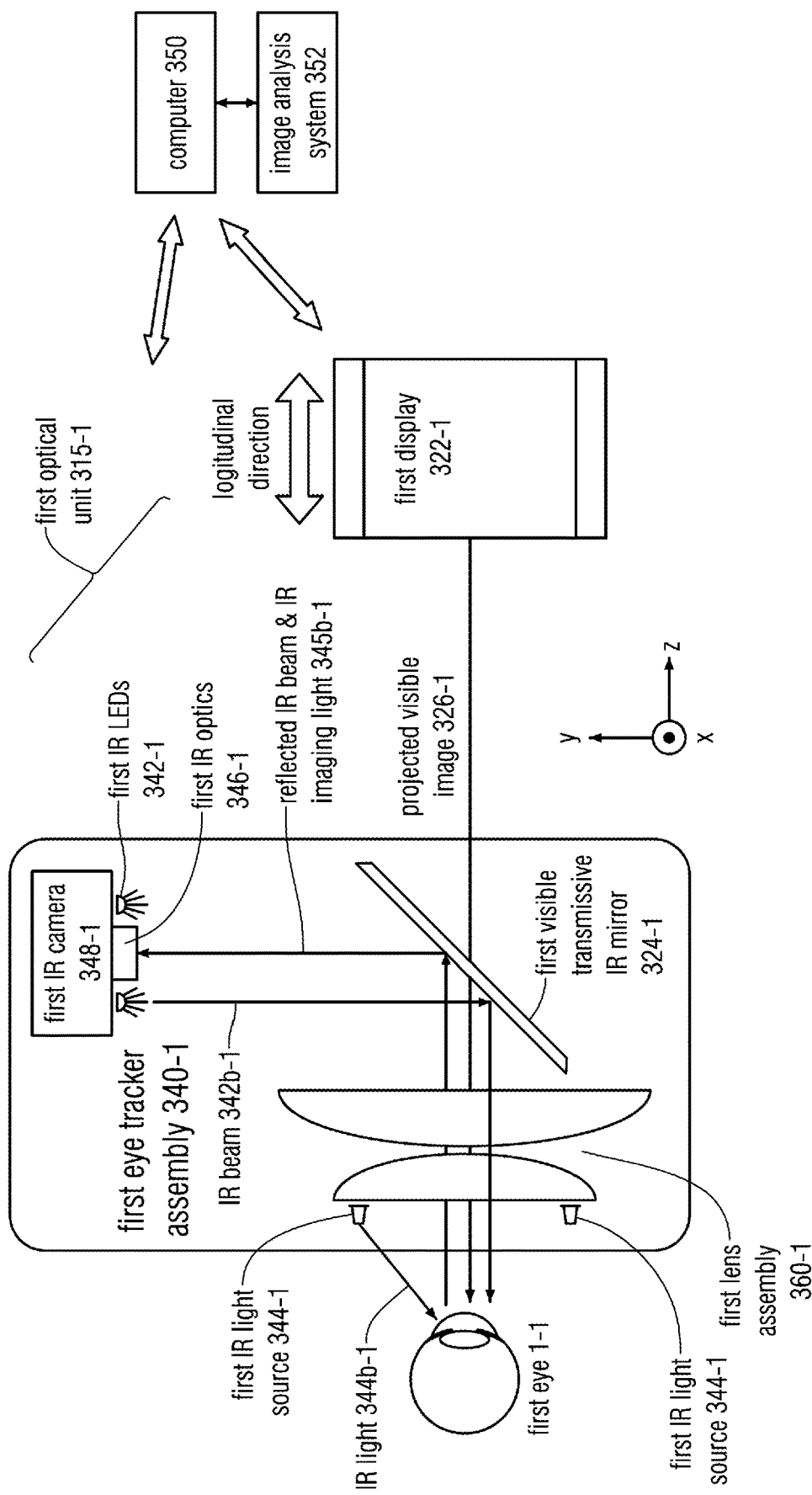

FIGS. 18A-B illustrate that the one or more first infrared (IR) light emitting diodes 342-1 can be positioned at different positions in the first eye-tracker assembly 340-1. In FIG. 18A, the first infrared (IR) light emitting diodes 342-1 are positioned at a frontal area of the first eye tracker assembly 340-1, close to the first eye 1-1. In these designs, the IR eye tracking beam 342$b$-1 may make a larger angle with the main optical axis of the first optical unit 315-1, possibly complicating the centering of the reflected IR light. In FIG. 18B, the one or more first infrared (IR) light emitting diodes 342-1 are positioned much higher upstream along the optical path, in the proximity of the first infrared (IR) camera 348-1, often close to its central first IR optics 346-1. In these designs, the FR eye tracking beam 342b-1 can be well aligned with the main optical axis of the first optical unit 315-1.

In some embodiments of the system for determining binocular alignment 310, the computer 350 can include, or be connected to, an image analysis system 352, to determine an orientation of the first eye 1-1 and the second eye 1-2, using the reflected IR eye tracking beams 342b-1 and 342b-2, and using the IR image formed by the infrared imaging lights 344b-1 and 344b-2, the reflected beams together labeled 345b-1 and 345b-2. The image analysis system 352 can be configured to use the detected reflected infrared eye tracking beams 342b-1 and 342b-2 to determine Purkinje reflections from the first eye 1-1 and the second eye 1-2; and to use the IR image formed by the infrared imaging lights 344b-1 and 344b-2 to determine pupillary attributes of the first eye 1-1 and the second eye 1-2. The Purkinje reflections can be any one of the so-called P1. P2, etc. Purkinje reflections, labeled according to which optical surface of the eye they reflect from. One of the often-used Purkinje reflection is P1, the reflection from the frontal surface of the cornea. The IR beam 342b-1 is often directed by the first IR LEDs 342-1 to reflect from the apex of the cornea to yield a central P1 Purkinje reflection. The determination of the gaze direction can also involve determining one of the pupillary attributes, such as the location of the pupil center, or how much ellipticity the image of the pupil has. When the eye optical axis is aligned with a main optical axis of the first eye tracker assembly 340-1, then the pupil of the eye 1-1 will appear as a circle for typical eyes. When the gaze direction of the eye 1-1 turns away from this main optical axis by a rotation angle, the same pupil will appear as an ellipse. Analyzing the ellipticity of this ellipse, as e.g. given by the ratio of its minor axis to its major axis, and determining the directions of these axes delivers important information about the gaze direction's rotation angle. Yet other pupillary attributes can involve imaging the iris and recording the location of a specific feature of the iris. Determining the pupilary attributes can involve edge recognition software to identify the precise edges of the pupils.

The operation of these first and second optical units 315-1 and 315-2 and the image analysis system 352 has been designed by recalling that for many patients, their pupils are not of the same size, they are not completely circular, or completely aligned. For example, for patients whose eyes are not fully aligned, when one of the two eyes is aligned with the optical axis of the corresponding first and second eye tracker assembly 340-1 or 340-2, the other eye is not aligned with its corresponding eye tracker optical axis. Finally, the Purkinje reflection may also not come precisely from the apex.

In order to determine the gaze directions of the first and second eyes, 1-1 and 1-2 in spite of all these possible deviations from the ideal situation, the image analysis system 352 is often operated by first instructing the patient to look straight ahead, and then registering and recording the location of the Purkinje reflection P1 and the pupil center of the patient by the first and second IR cameras 348-1 and 348-2. (As at other loci in this document, since the second eye tracker assembly 340-2 is analogous to the first eye tracker assembly 340-1, for brevity it is not illustrated in a separate, repetitive figure.) In addition, the ellipticity and other pupillary attributes of the eye can be also recorded. Connecting the location of the Purkinje reflection Pt with the pupil center can be used to define the direction of gaze, or direction of the optical axis of the eye. All these recordings are used to serve as a reference direction for subsequent measurements. This reference-setting step can be then followed by projecting visible images 326-1 and 326-2 by the first and second displays 322-1 and 322-2 for the patient, accompanied by re-measuring the Purkinje reflection(s), pupil center and other pupillary attributes like ellipticity in reaction to these images, followed by comparing the Purkinje reflection(s), pupil centers, and the pupillary attributes of the first eye 1-1 and the second eye 1-2 to the previously determined reference Purkinje reflections, pupil centers, and pupillary attributes of the first eye 1-2 and the second eye 1-2. Comparing these measured valued to the reference values is then used to determine the gaze directions and their changes, as described next.

In embodiments, the image analysis system 352 can use the location of the centers of the pupil in the xy plane, as determined from the IR image, formed from the reflected IR lights 344b-1 and 344b-2, and the locations of the Purkinje reflections P1 from the apex of the cornea, as determined from the reflected IR beams 342b-1 and 342b-2. If the pupil centers overlap, or coincide, with the corneal apexes in the xy plane, then the eye is looking straight forward, as in the reference IR images. When the pupil centers and the corneal apexes arc offset in the xy plane, then from the direction and magnitude of the offsets the image analysis system 352 can determine the rotational angle of the gaze direction of each eye relative to the reference direction.

As mentioned earlier, for a fraction of patients, even when they look straight forward, the pupil center and the corneal apex may not coincide even in the reference images. But even in these cases, the image analysis system 352 can take the locations of the pupil center and corneal apex in an image of a rotated eye, then subtract the reference locations of these, and from the so-constructed differences, determine the rotational angle of the gaze direction of the eyes 1-1 and 1-2 by which the eyes responded to the projected visible images 326-1 and 326-2. Other embodiments can determine the gaze directions by other methods, such as other pupillary attributes and/or other Purkinje reflections. Yet other embodiments can use multiple pupillary attributes without Purkinje reflections. Yet others can do the opposite: use multiple Purkinje reflections without pupillary attributes.

Since the eyes perform quick saccadic motions many times a second, the gaze directions rapidly vary in time. Therefore, the above-mentioned Purkinje reflections and pupil centers, and possibly other pupillary attributes, are representative of a specific gaze direction if they are measured close to each other in time. And in reverse: if they are measured with a substantial time difference, bigger than 0.1 second, or 1 second, or more, then the gaze direction computed by the image analysis system 352 may be less and less accurate. To increase the accuracy of this computation, in some embodiments the one or more first infrared light emitting diodes 342-1 project the infrared eye-tracking beam (IR beam) 342b-1 in an alternating manner with the first infrared light source 344-1 illuminating with the infrared imaging light 344b-1; and the one or more second infrared light emitting diodes 342-2 project the infrared eye-tracking beam 342b-2 in an alternating manner with the second infrared light source 344-2 illuminating with the infrared imaging light 344b-2. The frequency of the alternation can be in the 1-1,000 Hz range, in some embodiments in the 10-150 Hz range, in some embodiments in the 60-120 Hz range. With these alternations, the first and second IR cameras 348-1 and 348-2 can determine the Purkinje reflections and pupil centers, and possibly other pupillary attributes, within 1-1,000 milliseconds of each other, in other embodiments within 6-100 milliseconds, in yet others 8-16 milliseconds. Determining the Purkinje reflections and pupil centers, and possibly other pupillary attributes, so close to each other advantageously increases the accuracy of the computation of the gaze direction by the image analysis system 352. As mentioned before, in some embodiments of the system for determining binocular alignment 310, only multiple pupillary attributes are determined, in other embodiments of system 310 only multiple Purkinje reflections. Determining either of these with the above repetition rates also increases the accuracy of the determination of the gaze directions.

In some embodiments of the system for determining binocular alignment 310, the first eye tracker assembly 340-1 also includes a first visible-transmissive infrared mirror 324-1, positioned to transmit images from the first display 322-1 along the longitudinal direction to the first eye 1-1; and to redirect the reflected infrared eye-tracking beam 342b-1 and the infrared imaging light 344-1, together labeled 345b-1, from the first eye 1-1 to the first infrared camera 348-1 in a lateral direction; and the second eye tracker assembly 340-2 includes a second visible-transmissive infrared mirror 324-2, positioned to transmit images from the second display 322-2 along the longitudinal direction for the second eye 1-2: and to redirect the reflected infrared eye-tracking beam and the infrared imaging light, together 345b-2, from the second eye 1-2 to the second infrared camera 348-2 in the lateral direction. In some embodiments, the first infrared camera 348-1 is positioned relative to the first visible-transmissive infrared mirror 324-1 in one of a vertical lateral and a horizontal lateral direction; and the second infrared camera 348-2 is positioned relative to the second visible-transmissive infrared mirror 324-2 in one of the vertical lateral and the horizontal lateral direction. The horizontal lateral direction corresponds to the x axis, and the vertical lateral direction corresponds to the y axis of the xyz coordinate system of FIGS. 17-18.

There are various eye-tracking display systems available, e.g. in virtual reality goggles, in which the IR eye tracking beam and the projected visible image do not share a common optical path and they do not utilize visible transparent IR mirrors. In these designs, the eye trackers' IR camera is directly pointed at the eye. However, the geometry of the design dictates that these IR cameras are pointed at the eye from a high angle. As such, the eye tracking IR beam often suffers occlusions from longer eyelashes that confounds their image analysis systems and can lead to tracking impasses. Such occlusion problems by the eyelashes are avoided in the present system for determining binocular alignment 310 by making the reflected IR beams and IR imaging lights 345b-1 and 345b-2 share the main optical path, leaving the eye in a normal/z/longitudinal direction, and then redirected by the first and second visible transparent IR mirrors 324-1 and 324-2.

As already referenced earlier, when measuring binocular alignment, the first display 322-1 is actuatable to a first longitudinal position according to the simulated distance, wherein the first longitudinal position is dynamically corrected according to the optical power of the first eye 1-1; and the second display 322-2 is actuatable to a second longitudinal position according to the simulated distance, wherein the second longitudinal position is dynamically corrected according to the optical power of the second eye 1-2. The first and second displays 322-1 and 322-2 are actuatable continuously along the longitudinal/z direction, which allows for a more precise correction of the simulated distance according to the optical power, or prescription, of the eyes 1-1 and 1-2 of the patient. It is notable also that many virtual reality displays achieve economic advantages by using a single display, and display the images for the left and right eyes on corresponding halves of this single display. Such systems, however, do not have the freedom to move the two halves of the display to different z coordinates, even though for most people the prescription in their two eyes are different and thus would call for differing z coordinates. Embodiments of the system for determining binocular alignment 310, in contrast, are well-suited to handle such different prescriptions as the two displays 322-1 and 322-2 are independently actuatable.

Further, when simulating images at different distances to determine the binocular misalignment at these distances, the horizontal lateral position of the images can be moved accordingly on the first and second displays 322-1 and 322-2 by the computer 350.

FIGS. 18A-B also illustrate that the first optical unit 315-1 can include a first lens assembly 360-1 to receive and guide the infrared eye-tracking beam and the infrared imaging light, both reflected from the first eye and together labeled 345b-1, towards the first infrared camera 348-1, and to reduce at least one of a chromatic aberration, an optical aberration, an optical astigmatism, and a wavefront distortion; and the second optical unit 315-2 can include a second lens assembly 360-2 to receive and guide the infrared eye-tracking beam and the infrared imaging light, both reflected from the first eye and together labeled 345b-2, towards the first infrared camera 348-2, and to reduce at least one of a chromatic aberration, an optical aberration, an optical astigmatism, and a wavefront distortion. (The elements of the second optical unit 315-2 are not shown explicitly for brevity—they are analogous to those of the first optical unit 315-1.)

In some embodiments of the system to determine a binocular alignment 310, the first infrared camera 348-1 and the first lens assembly 360-1 are adjustable together; and the second infrared camera 348-2 and the second lens assembly 360-2 are adjustable together. In embodiments where these two elements are not adjustable together, the infrared cameras 348-1 and 348-2 need to be much larger, so as to be able to retain the high resolution and low distortion of the images even if the first and second lens assemblies 360-1 and 360-2 have been adjusted to an off-center, misaligned position. And in reverse, in the embodiments where the first and lens assemblies 360-1 and 360-2 are adjustable together with the first and second infrared cameras 348-1 and 348-2, the first and second infrared cameras 348-1 and 348-2 can be made much smaller since the collinearity with the first and lens assemblies 360-1 and 360-2 is maintained in spite of the adjustments. The smaller size of the first and second infrared cameras 348-1 and 348-2 advantageously reduces the size of the entire system to determine a binocular alignment 310.

Figure 19:
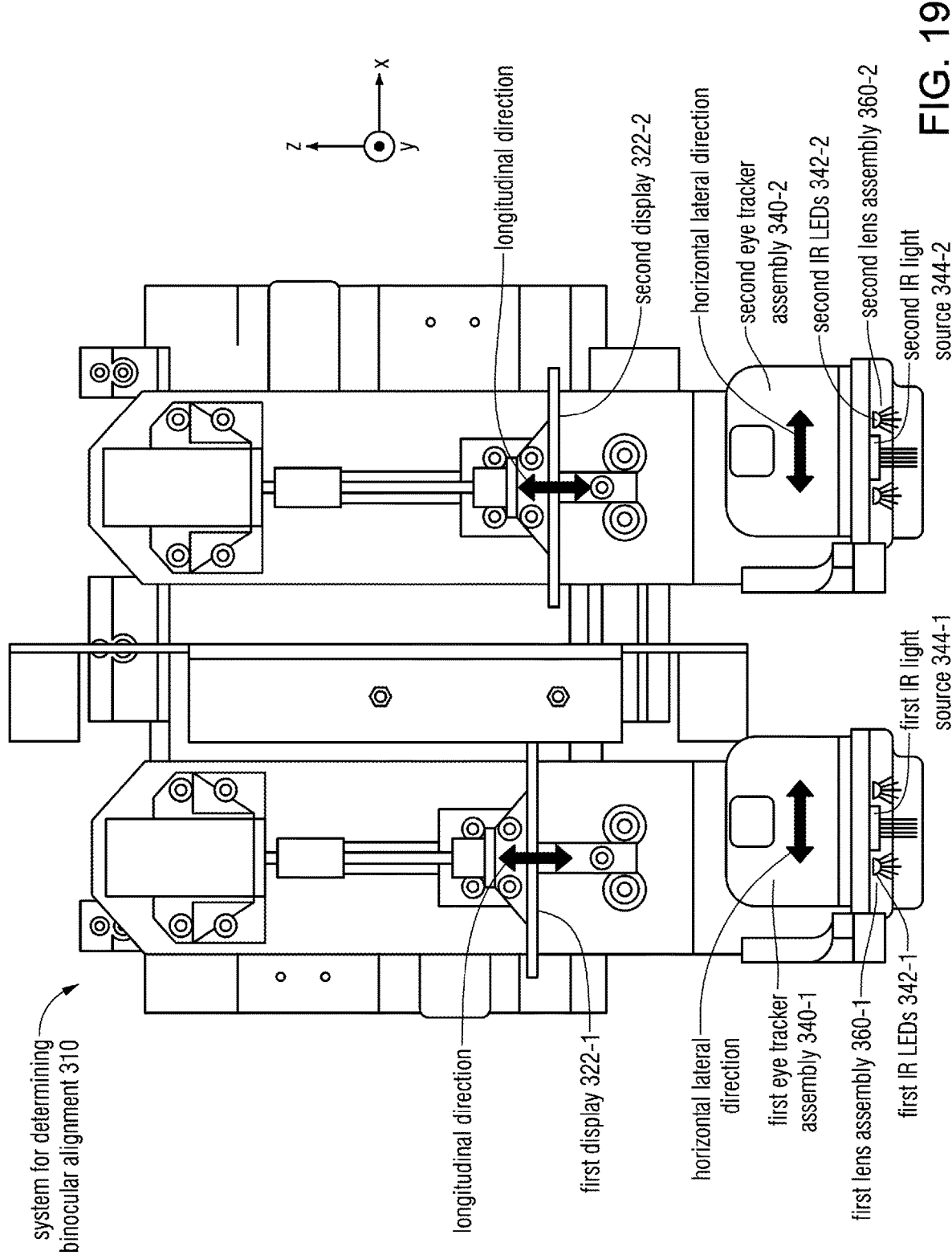
FIG. 19 illustrates a view of the system for determining binocular alignment.

FIG. 19 illustrates an embodiment of the system for determining binocular alignment 310. It shows the same elements as FIG. 17-18, from the top, y direction, or vertical lateral direction looking down, similarly to FIG. 17. In particular, the directions of the longitudinal/z directional actuation, and the horizontal lateral/x direction are well-demonstrated.

Figure 20:
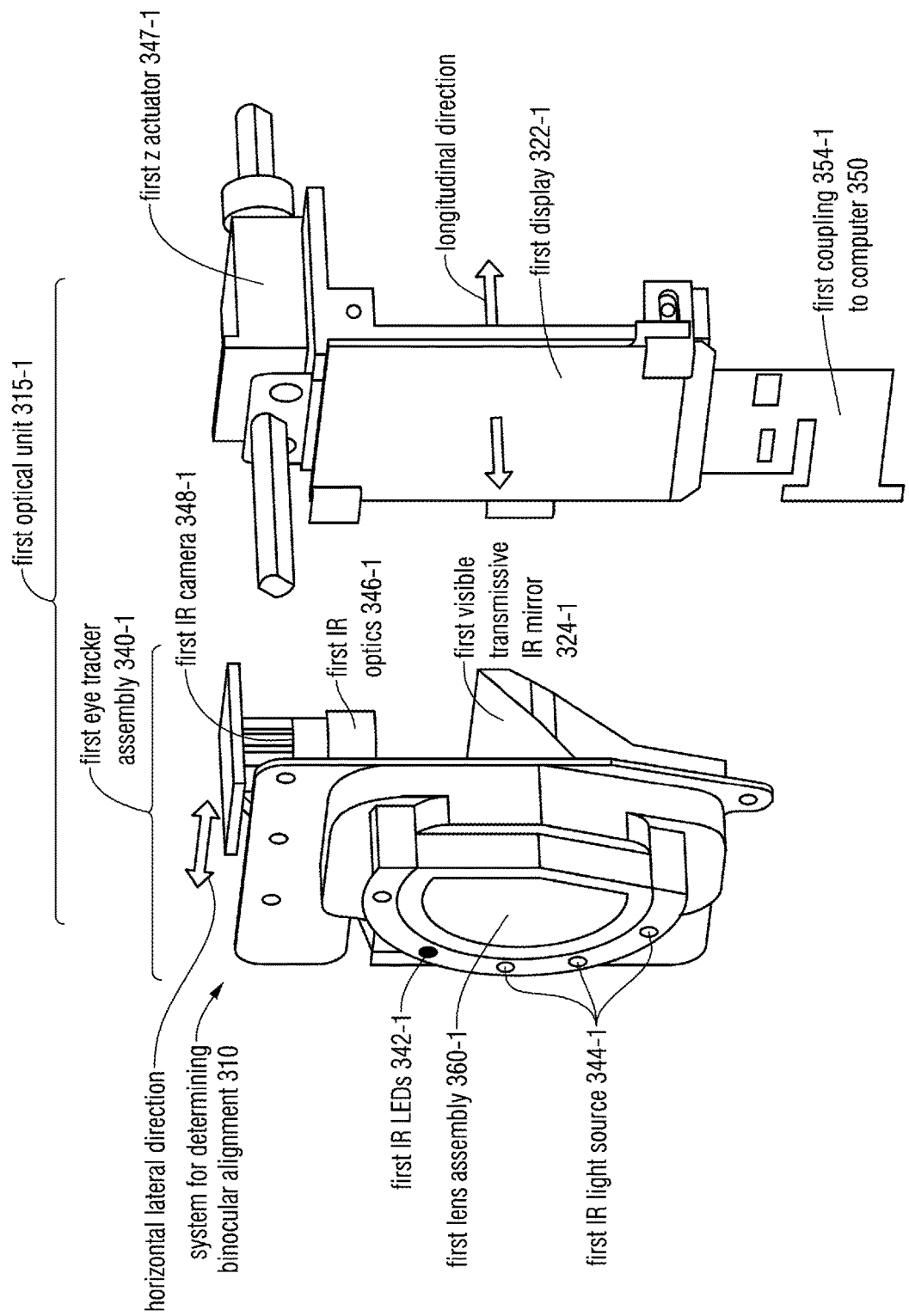
FIG. 20 illustrates a perspective view of the first optical unit.

FIG. 20 illustrates an embodiment of the first optical unit 315-1 of the system for determining binocular alignment 310 from a perspective view. Besides the previously described elements, the further element of a first z actuator 347-1 is visible, configured to actuate the first display 322-1 along the longitudinal/z direction. Further, a first coupling 354-1 to the computer 350 is also visible, coupling the first display 322-1 to the computer 350 with a set of flexible or deformable communication lines. The first display 322-1 can be configured to display images for the first eye 1-1 modified according to at least one of an optical power, a cylinder, and a prism of the first eye 1-1; and the second display 322-2 can be configured to display images for the second eye 1-2 modified according to at least one of an optical power, a cylinder, and a prism of the second eye 1-2.

In some embodiments, the first display 322-1 and the second display 322-2 may include a liquid crystal display, a light emitting diode (LFD) display, an organic LED display, a quantum dot LED display, a microlens array, a digital mirror device, and a scanning projector micro-electrical-mechanical system.

Figure 21:
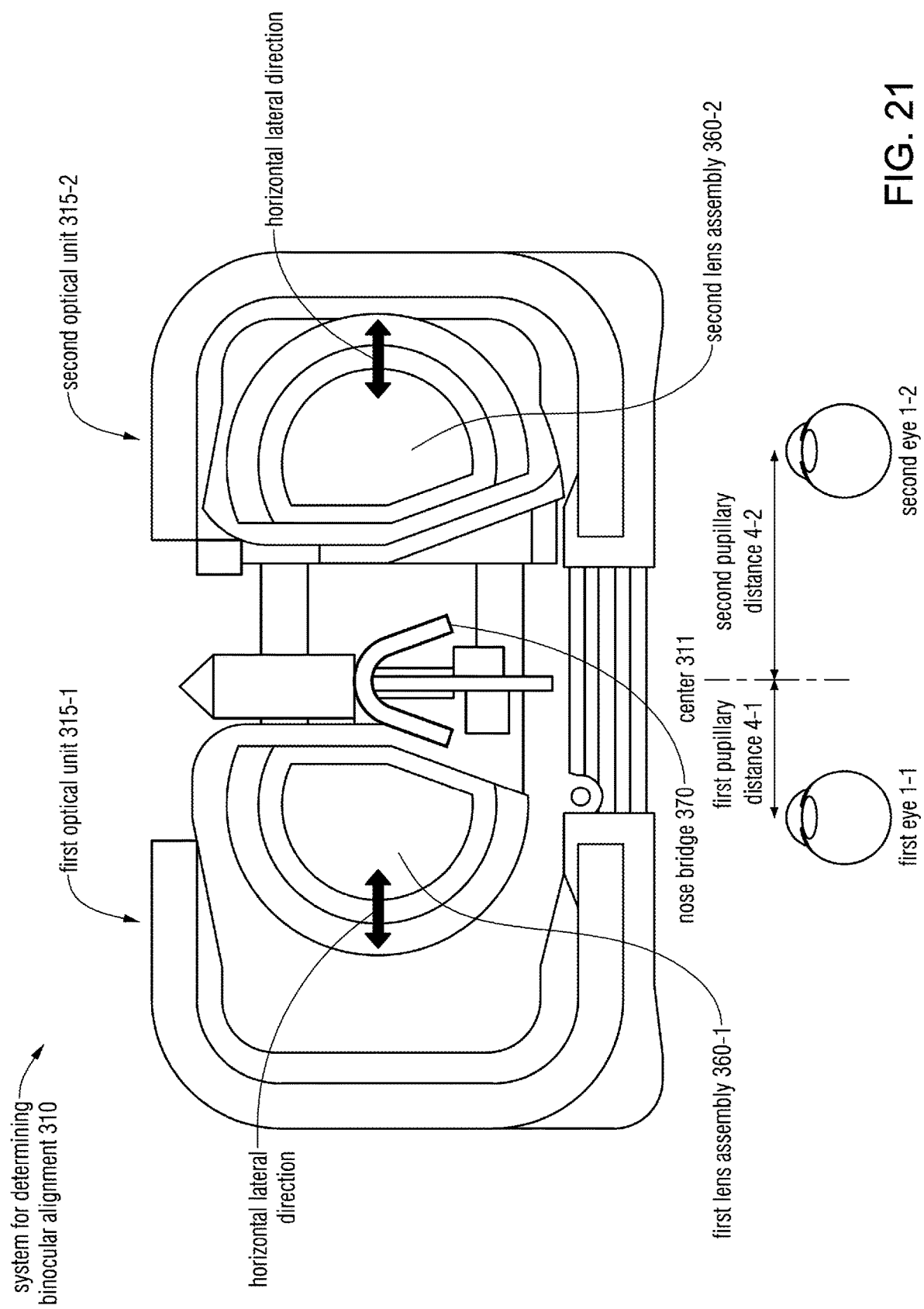
FIG. 21 illustrates a frontal view of the system for determining binocular alignment.

FIG. 21 illustrates a frontal, z directional view of the system for determining binocular alignment 310. This is what is visible for the patient. The first and second lens assemblies 360-1 and 360-2 are shown. Beyond that, some embodiments include a nose bridge 370, located centrally between the first optical unit 315-1 and the second optical unit 315-2, configured to receive and immobilize a patient's nose.

Such embodiments provide progress relative to related diagnostic systems. Quite a few related diagnostic systems intend to immobilize the patient's head and eyes with a variant of a chin rest, where the patient rests her/his chin. However, the chin still acts as an axis of rotation for the patient's head, and therefore the eyes can still rotate around the rested chin with the chin-eye distance as a radius, causing rotational misalignment with the diagnostic apparatus. This remaining rotational misalignment can be minimized or eliminated by immobilizing the patient's head and eyes at the nose instead of at the chin. The nose bridge 370, with its "downward V" shape achieves this function: it immobilizes the patient's head at the top of the nose, very close to the eyes, instead of at the chin. For this reason, the eyes are much more solidly immobilized relative to the system for determining binocular alignment 310 in such embodiments.

Another advantage is demonstrated by FIGS. 17-21. Denoting the center of the system for determining binocular alignment 310 as center 311, for a fraction of patients the pupil center of their first eye 1-1 and that of their second eye 1-2 are not at an equal distance from the center of symmetry of their heads. These differences can be 1-2 mm, enough to cause notable errors if the measurements are analyzed assuming a symmetric positioning of the eyes 1-1 and 1-2. Therefore, in embodiments of the system for determining binocular alignment 310, it is advantageous to make not only the overall pupillary distance ("PD") adjustable to accommodate patient-to-patient variations, but also to make the first/left eye mono-pupilary distance 4-1, defined relative to the center 311, adjustable independently from the second/right eye mono-pupilary distance 4-2, again defined relative to the center 311. In embodiments this is realized by making the first eye optical unit 315-1 adjustable in the horizontal lateral/x direction relative to the nose bridge 370 to accommodate the mono-pupillary distance 4-1 of the first eye 1-1, as indicated with a block arrow; and making the second optical unit 315-2 adjustable in the horizontal lateral/x direction relative to the nose bridge 370 to accommodate the mono-pupillary distance 4-2 of the second eye 1-2. In some cases, it may be possible to achieve this same goal by making only the first and second eye tracker assemblies 340-1 and 340-2 adjustable in the horizontal lateral direction relative to the nose bridge 370.

Figure 22:
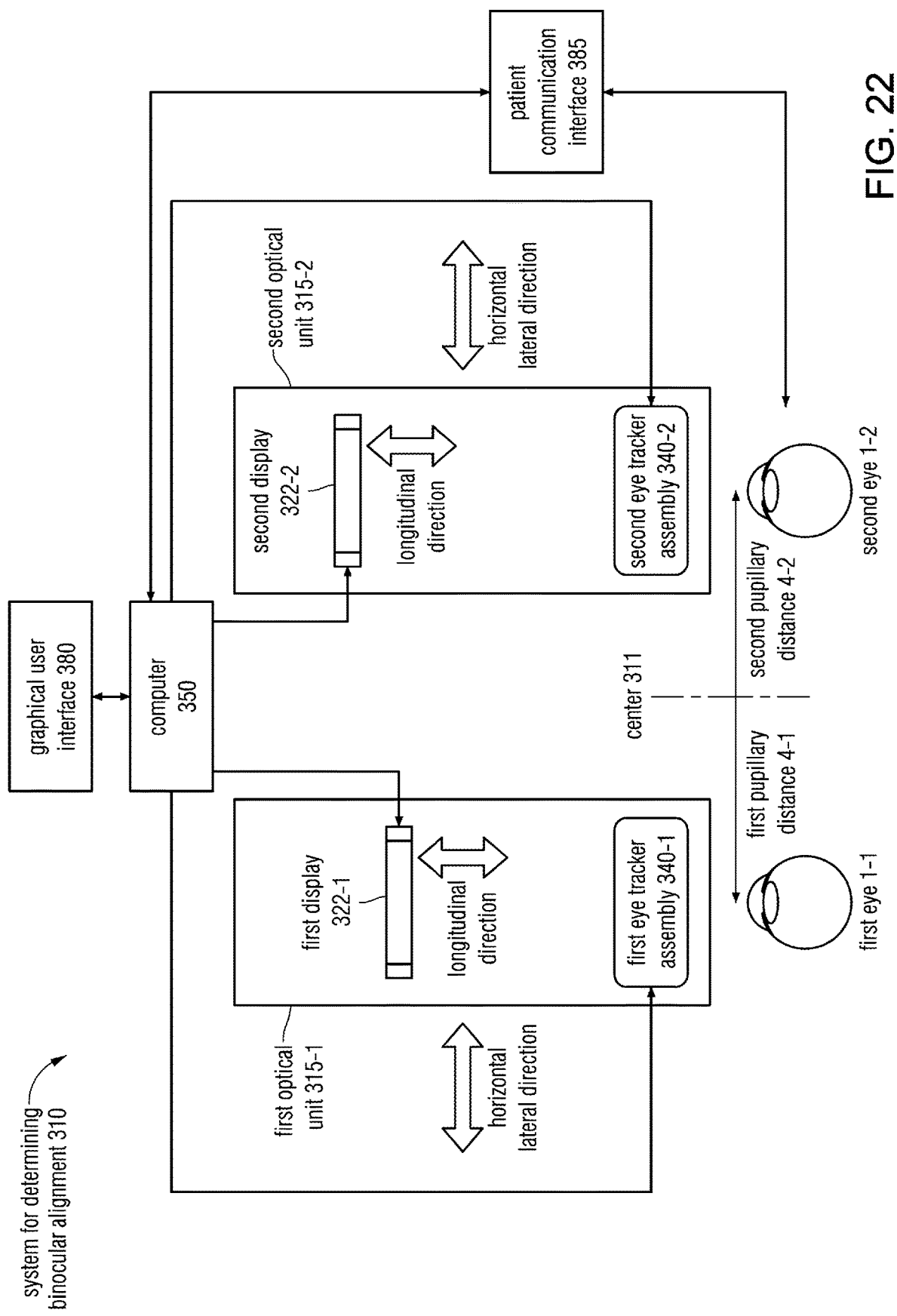
FIG. 22 illustrates an embodiment of the system for determining binocular alignment with a graphical user interface and a patient communication interface.

FIG. 22 illustrates further features of embodiments of the system for determining binocular alignment 310. Some embodiments can include a graphical user interface 380, configured for a medical operator to interact with the computer 350 to manage the determination of the binocular alignment. This graphical user interface 380 can show to the medical operator, such as an optometrist or technician, the infrared images captured by the first and second IR cameras 348-1 and 348-2, the movement of the eyes 1-1 and 1-2, the available diagnostic steps to choose from, and parameters of the diagnostic procedure to set, among others.

Yet-other embodiments of the system for determining binocular alignment 310 can include a patient communication interface 385, such as a loudspeaker, to instruct a patient to follow steps of the determination of the binocular alignment. These instructions can come from a remote operator, or they can be pre-recorded, and synchronized with the computer 350 projecting specific visible images 326-1 and 326-2. Other embodiments of the patient communication interface 385 can include a patient feedback portal, to receive a feedback from the patient. Examples include a push-button, a track wheel, a touchpad, a microphone, and an audio-interactive device. With any of these patient feedback portals, the patient can select a feedback in response to a step of the diagnostic process. In an example, the computer 350 may start adjusting the longitudinal/z direction of the fist display 322-1, and the loudspeaker of the patient communication interface 385 can convey the pre-recorded instruction to the patient: "indicate when the image is clear by pushing the button". When the patient pushes the button of the patient communication interface 385, the computer 350 can record the longitudinal/z position of the first display 322-1 that is informative regarding the patient's prescription, or optical power of the eye 1-1. Or, the computer can move projected visible images 326-1 and 326-2 in a horizontal lateral/x direction on the first and second displays 322-1 and 322-2, and ask the patient to indicate through a push-button when the two images 326-1 and 326-2 are fused, or when the fusion of the two images is broken. The horizontal lateral/x positions of the two images 326-1 and 326-2 are informative regarding the binocular alignment of the patient's eyes 1-1 and 1-2.

Figure 23:
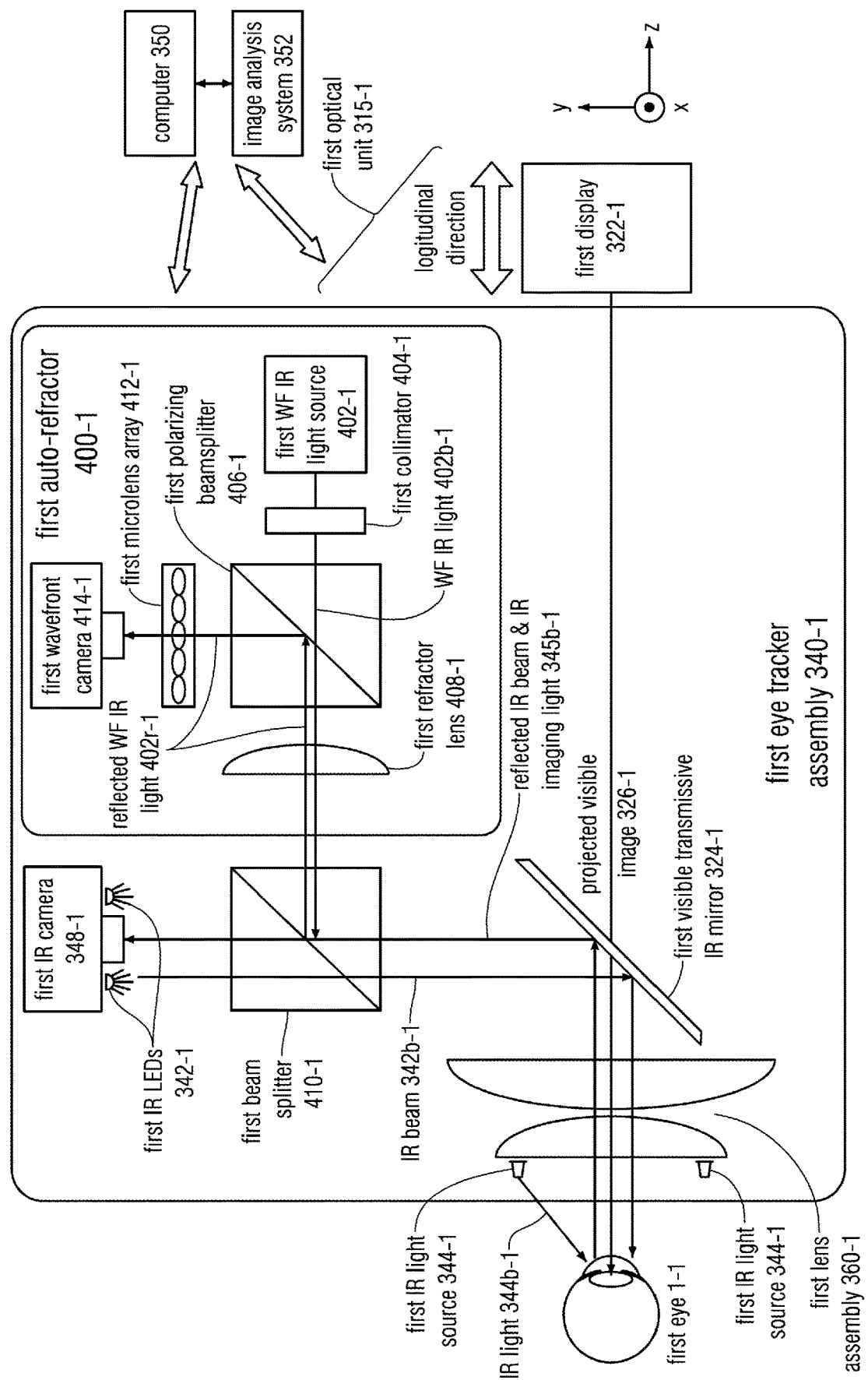
FIG. 23 illustrates an embodiment with an auto-refractor.

FIG. 23 illustrates that in some embodiments, the first eye-tracker assembly 340-1 can include a first auto-refractor 400-1, to determine refractive information about the first eye 1-1: and the second eye-tracker assembly 340-2 can include a second auto-refractor 400-2, to determine refractive information about the second eye 1-2. As before, the second auto-refractor 400-2 can be analogous to the first auto-refractor 400-1 and thus does not need to be shown expressly. The refractive information can be simply the refractive power of the investigated eye, needed to perform the method 100. For example, the prescription of the patient may have changed unbeknownst to her/him since the last examination by the optometrist. Or the optometrist may want to track the degree of accommodation in response to moving the first display 322-1 in the longitudinal/z direction. Or the optometrist may want to check a higher order astigmatism or aberration.

In embodiments, the first auto-refractor 400-1 can include a first wavefront (WF) infrared (IR) light source 402-1, to project a WF IR light 402b-1 into the first eye 1-1. This first WF IR light source 402-1 can have many different embodiments, including a LED, a LED array, a superluminescent LED called SLED, and an expanded beam laser, among others. The WF IR light 402b-1 can be guided through a first collimator 404-1, and a first polarizing beam splitter 406-1, whose transmitting polarization plane is aligned with the polarization plane of the first WF IR light source 402-1. The first WF IR light 402b-1 can be coupled into the optical pathway of the first eye tracker assembly 340-1 through a first beam splitter 410-1, optionally through an optional first refractor lens 408-1. From here, the WF IR light 402b-1 can be guided to the first eye 1-1 via the main optical pathway of the first eye tracker assembly 340-1 that includes the first visible transparent IR mirror 324-1 and the first lens assembly 360-1, as shown in FIG. 23. The (typically pencil-beamlike) WF IR light 402b-1 then reflects from the retina of the first eye 1-1 into a wider spatial angle as a reflected WF IR light 402r-1. As the reflected WF IR light 402r-1 propagates through the lens and cornea of the first eye 1-1, its expanding wavefront gets modified by refraction through the lens and the cornea, and thus acquires information about the refractive properties of the lens and cornea of the first eye 1-1. The reflected WF IR light 402r-1 propagates back through the main optical pathway of the first eye tracker assembly 340-1, gets split out of it by the first beam splitter 410-1, and is eventually guided by the first polarizing beam splitter 406-1 towards a first microlens array 412-1. This first microlens array 412-1 is configured to receive and split the reflected WF IR light 402r-1 from the first eye 1-1 into beamlets. The beamlets are then captured by a first wavefront camera 414-1 to be analyzed to determine the refractive information they carry about the first eye 1-1.

The above described embodiment of the autorefractor 400-1 broadly follows the design of the Shack-Hartmann wavefront analyzers. Other embodiments can use other wavefront analyzing designs, such as Talbot-Moire interferometry, slit lamps technology, Tscherning aberrometry, lensometer technology, and the alike. Lensometer devices can, in fact, capture optical characteristics of the eye beyond the sphere/refractive power. These characteristics include the cylinder power and axis information, among others.

Systems for determining binocular alignment 310 that have an autorefractor 400-1 offer another useful diagnostic modality. A class of binocular alignment problems is called "accommodation lag". This refers to the phenomenon when a patient is presented by an object at a presentation distance d1, but the patient's eyes focus at a different distance d2 that does not equal d1. Often d2 is larger than d1: d2>d1. Systems 310 with an autorefractor 400-1 can recognize and diagnose such an accommodation lag.

On a higher, conceptual level, a primary goal of the systems for determining binocular alignment 310 is to diagnose and characterize the cooperation and crosslinking of two systems that control human vision: the focusing system that focuses the crystalline lens at the objects at their actual distance by engaging the ciliary muscles; and the vergence system that rotates both eyes to look at the objects at their actual distance by engaging the six extraocular muscles. Embodiments of the systems for determining binocular alignment 310 in FIGS. 17-23 deliver high quality diagnostic information on these crosslinked systems by several design choices, including: they simulate the objects by the first and second displays 322-1 and 322-2 that are actuatable in the longitudinal/z direction; they use first and second optical units 315-1 and 315-2 that are actuatable in the horizontal lateral direction, and, optionally, they include the first and second autorefractors 400-1 and 400-2. These design choices make these systems for determining binocular alignment 310 capable of diagnosing and characterizing the cooperation and crosslinking of the focusing system and the vergence system in an integrated, "closed loop" manner. Thus, embodiments of the system to determine a binocular alignment of 310 are configured to determine a vergence response and an accommodative response in an integrated manner by the first display 322-1 and the first eye tracker assembly 340-1, and the second display 322-2 and the second eye tracker assembly 340-2 being configured to determine the vergence response; and the first display 322-1 and the first auto-refractor 400-1, and the second display 322-2 and the second auto-refractor 400-2 being configured to determine the accommodative response.

For completeness, finally reference is made to the method of determining binocular alignment 100, previously described in relation to FIGS. 11-16. The computer 350 can be configured to carry out steps of this method 100. As such, in some embodiments, the computer 350 can be configured to determine a Fixation Disparity of a patient as an amount of angular misalignment between a central target and a peripheral fusion lock of moving targets around an image with a blank center, as part of the determining of the binocular alignment.

In some embodiments, the computer 350 can be also configured to determine a Gross Phoria as an average amount of angular misalignment between the first eye 1-1 and the second eye 1-2 when the first display 322-1 and the second display 322-2 display dissimilar images with one of the eyes fixated on a target at a time, as part of the determining of the binocular alignment.

Figure 24:
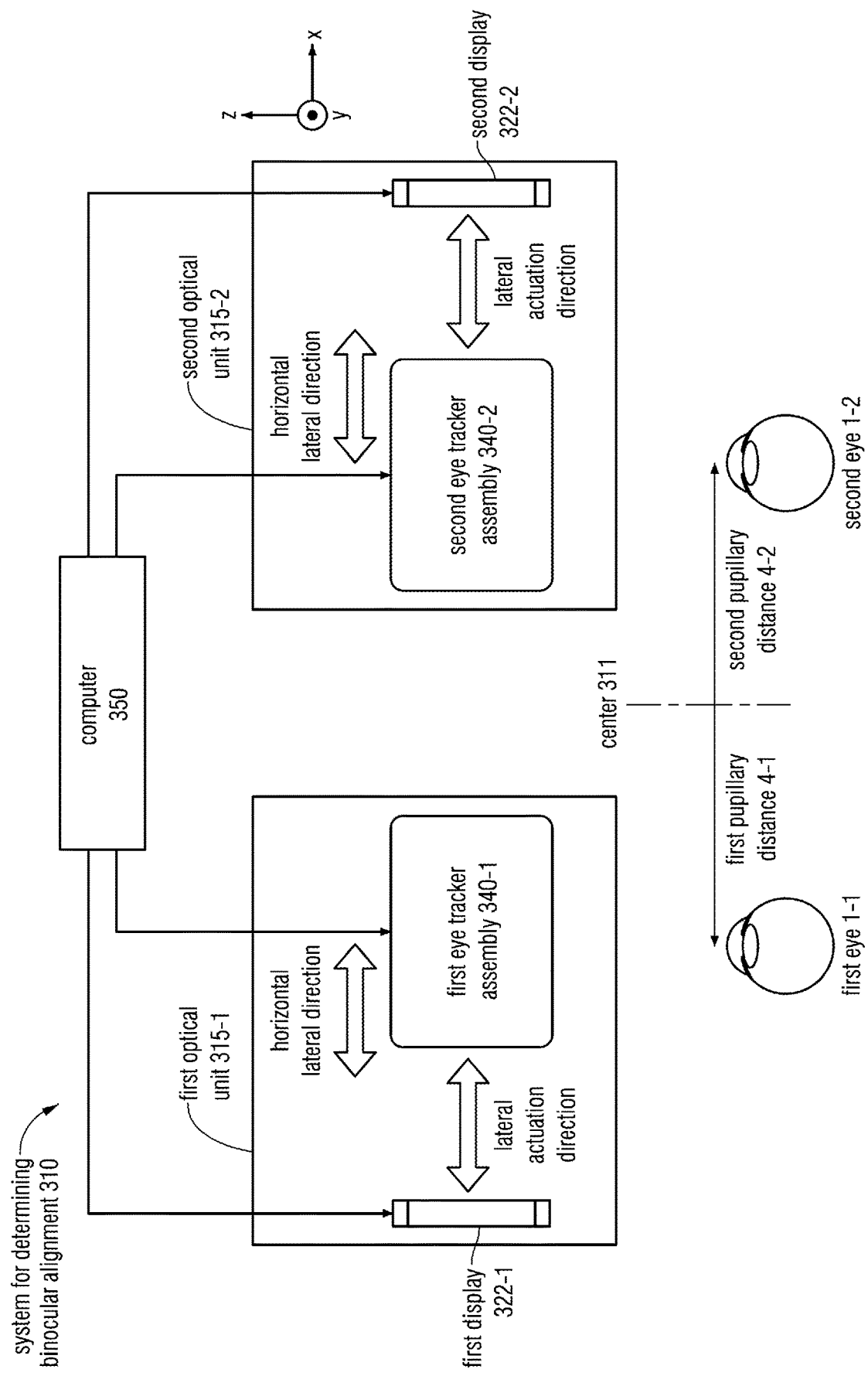
FIG. 24 illustrates an embodiment of a system for determining binocular alignment.
Figure 25:
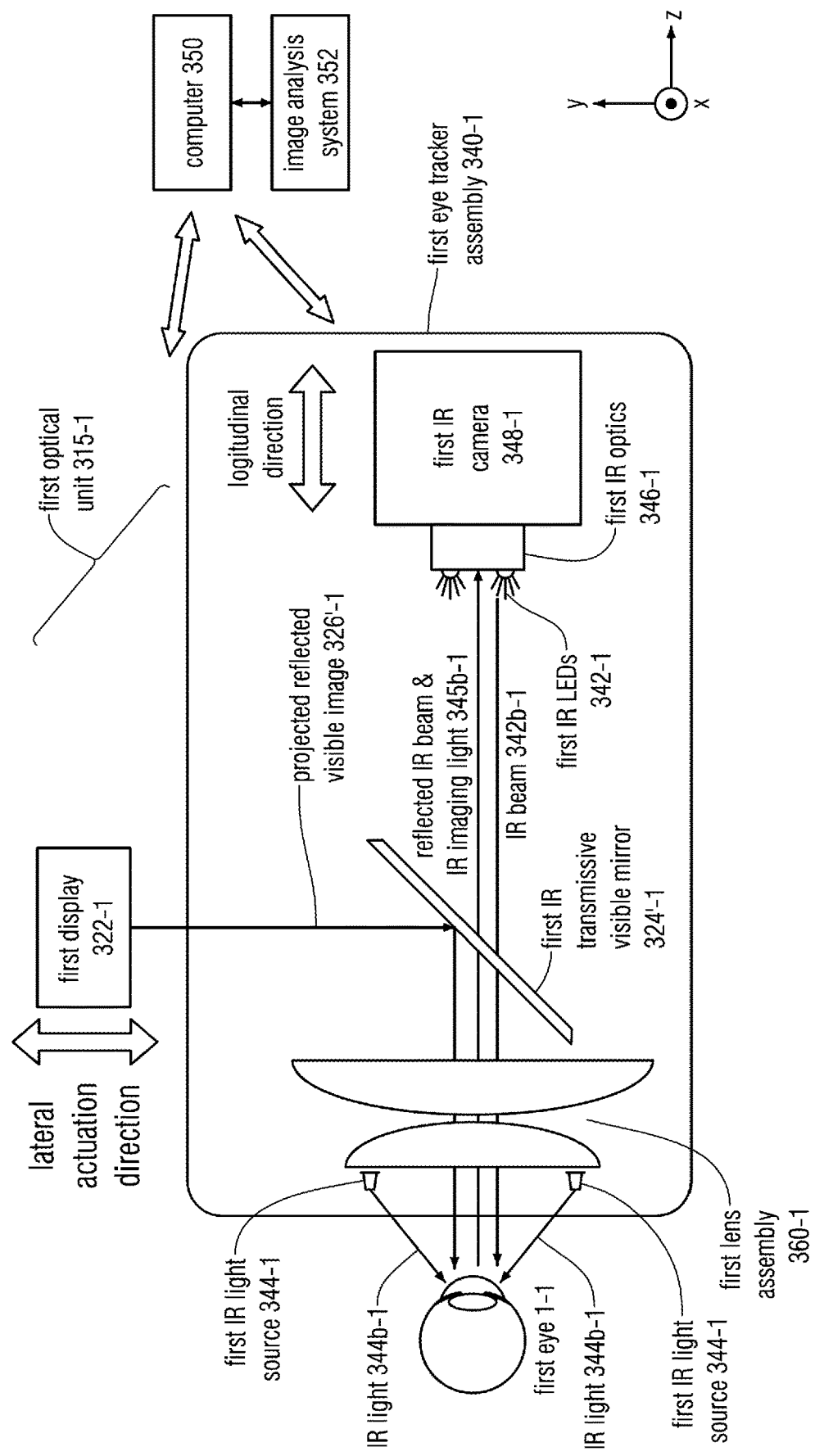
FIG. 25 illustrates an embodiment of a first optical unit.

FIGS. 24-25 illustrate a related embodiment of the system to determine a binocular alignment 310 that comprises a first optical unit 315-1, including a first display 322-1, to display images for a first eye 1-1, actuatable along a lateral actuation direction according to a simulated distance and an optical power of the first eye 1-1, and a first eye tracker assembly 340-1, to track a gaze direction of the first eye 1-1, adjustable in a horizontal lateral direction to accommodate a pupillary distance of the first eye 1-1; and a second optical unit 315-2, including a second display 322-2, to display images for a second eye 1-2, actuatable along the lateral actuation direction according to a simulated distance and an optical power of the second eye 1-2, and a second eye tracker assembly 340-2, to track a gaze direction of the second eye 1-2, adjustable in the horizontal lateral direction to accommodate a pupillary distance of the second eye 1-2; and a computer 350, coupled to the first optical unit 315-1 and the second optical unit 315-2, to determine the binocular alignment based on the gaze directions of the first eye 1-1 and the second eye 1-2. A notable difference from the embodiments of FIGS. 17-23 is that the positioning of the fist and second displays 322-1 and 322-2 is moved from a longitudinal arrangement to a lateral arrangement in the embodiment of FIGS. 24-25. This difference changes the form factor and dimension of the overall system 310, which can be advantageous in a crowded optometrist's office. The lateral actuation direction can be a horizontal lateral ("x") direction or a vertical lateral ("y") direction. In FIG. 24, the lateral actuation direction is horizontal, in FIG. 25, it is vertical.

FIG. 25 illustrates this latter vertical embodiment in more detail, concentrating on the first eye 1-1. The elements of the system to determine a binocular alignment 310 that are related to the second eye 1-2 are analogous and are not shown for clarity. In this system to determine a binocular alignment 310, the first eye tracker assembly 340-1 can include one or more first infrared light emitting diodes 342-1, to project an infrared eye-tracking beam 342b-1 on the first eye 1-1; a first infrared light source 344-1—possibly including several individual LEDs, to illuminate the first eye 1-1 with an infrared imaging light 344b-1; a first infrared camera 348-1, positioned along a longitudinal direction to detect the infrared eye-tracking beam and the infrared imaging light, both reflected from the first eye and collectively labeled 345b-1; and a first infrared-transmissive visible mirror 324'-1, to transmit the reflected infrared eye-tracking beam and the infrared imaging light 345b-1 from the first eye 1-1 to the first infrared camera 348-1 along the longitudinal direction; and to redirect images from the lateral actuation direction of the first display 322-1 to the longitudinal direction towards the first eye 1-1. The second eye tracker assembly 340-2 can include (not shown for clarity) one or more second infrared light emitting diodes 342-2, to project an infrared eye-tracking beam 342b-2 on the second eye 1-2: a second infrared light source 344-2, to illuminate the second eye 1-2 with an infrared imaging light 344b-2: a second infrared camera 348-2, positioned along the longitudinal direction to detect the infrared eye-tracking beam and the infrared imaging light, both reflected from the second eye, collectively labeled 345b-2; and a second infrared-transmissive visible mirror 324'-2, to transmit the reflected infrared eye-tracking beam and the infrared imaging light 345b-1 from the second eye 1-2 to the second infrared camera 348-2 along the longitudinal direction; and to redirect images from the lateral actuation direction of the second display 322-2 to the longitudinal direction towards the second eye 1-2. Typically, the beams to and from the eyes 1-1 and 1-2 are propagating through a first and second lens assemblies 360-1 and 360-2. The many variants and modifications of the embodiments of FIGS. 17-23 can have analogous implementations in the embodiment of FIGS. 24-25. For example, the horizontal adjustability can be implemented only for the first and second eye tracker assemblies 340-1 and 340-2, or for these assemblies together with the first and second displays 322-1 and 322-2, with or without the first and second lens assemblies 360-1 and 360-2, just like it was described for the embodiments of FIGS. 17-23.

While this document contains many specifics, these should not be construed as limitations on the scope of an invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The invention claimed is:

1. A system to determine a binocular alignment, comprising:
   a first optical unit, including
      a first display, to display images for a first eye, actuatable along a longitudinal direction according to a simulated distance and an optical power of the first eye, and
      a first eye tracker assembly, to track a gaze direction of the first eye, adjustable in a horizontal lateral direction to accommodate a pupillary distance of the first eye, the first eye tracker assembly including
         one or more first infrared light emitting diodes, to project an infrared eye-tracking beam on the first eye,
         a first infrared light source, to illuminate the first eye with an infrared imaging light, and
         a first infrared camera, to detect the infrared eye-tracking beam and the infrared imaging light, both reflected from the first eye; and
   a second optical unit, including
      a second display, to display images for a second eye, actuatable along the longitudinal direction according to a simulated distance and an optical power of the second eye, and
      a second eye tracker assembly, to track a gaze direction of the second eye, adjustable in the horizontal lateral direction to accommodate a pupillary distance of the second eye, the second eye tracker assembly including
         one or more second infrared light emitting diodes, to project an infrared eye-tracking beam on the second eye,
         a second infrared light source, to illuminate the second eye with an infrared imaging light, and
         a second infrared camera, to detect the infrared eye-tracking beam and the infrared imaging light, both reflected from the second eye; and
   a computer, coupled to the first optical unit and the second optical unit, to determine the binocular alignment based on the gaze directions of the first eye and the second eye.

2. The system to determine a binocular alignment of claim 1, wherein:
   the first display is structurally adjustable together with the first eye tracker assembly; and
   the second display is structurally adjustable together with the second eye tracker assembly.

3. The system to determine a binocular alignment of claim 1, wherein:
   the first eye tracker assembly is adjustable in a vertical lateral direction; and
   the second eye tracker assembly is adjustable in the vertical lateral direction.

4. The system to determine a binocular alignment of claim 1, wherein:
   the first infrared light source includes a set of infrared light emitting diodes, spatially distributed to illuminate the first eye with a widely dispersed infrared imaging light; and
   the second infrared light source includes a set of infrared light emitting diodes, spatially distributed to illuminate the second eye with a widely dispersed infrared imaging light.

5. The system to determine a binocular alignment of claim 1, wherein:
   the one or more first infrared light emitting diodes are positioned at one of a frontal area of the first eye tracker assembly and in the proximity of the first infrared camera; and
   the one or more second infrared light emitting diodes are positioned at one of a frontal area of the second eye tracker assembly and in the proximity of the second infrared camera.

6. The system to determine a binocular alignment of claim 1, the computer comprising:
   an image analysis system, to determine an orientation of the first eye and the second eye, using
      the detected reflected infrared eye tracking beams, and
      the detected reflected infrared imaging lights.

7. The system to determine a binocular alignment of claim 6, wherein:
the image analysis system is configured
to use the detected reflected infrared eye tracking beams to determine Purkinje reflections from the first eye and the second eye; and
to use the detected reflected infrared imaging lights to determine pupillary attributes of the first eye and the second eye;
to determine the gaze directions of the first eye and the second eye by comparing the Purkinje reflections and pupillary attributes of the first eye and the second eye to reference Purkinje reflections and pupillary attributes of the first eye and the second eye.

8. The system to determine a binocular alignment of claim 1, wherein:
the one or more first infrared light emitting diodes is projecting the infrared eye-tracking beam in an alternating manner with the first infrared light source illuminating with the infrared imaging light; and
the one or more second infrared light emitting diodes is projecting the infrared eye-tracking beam in an alternating manner with the second infrared light source illuminating with the infrared imaging light.

9. The system to determine a binocular alignment of claim 1, wherein:
the first eye tracker assembly includes a first visible-transmissive infrared mirror, positioned
to transmit images from the first display along the longitudinal direction to the first eye; and
to redirect the reflected infrared eye-tracking beam and the infrared imaging light from the first eye to the first infrared camera in a lateral direction; and
the second eye tracker assembly includes a second visible-transmissive infrared mirror, positioned
to transmit images from the second display along the longitudinal direction to the second eye; and
to redirect the reflected infrared eye-tracking beam and the infrared imaging light from the second eye to the second infrared camera in the lateral direction.

10. The claim of 9, wherein:
the first infrared camera is positioned relative to the first visible-transmissive infrared mirror in one of a vertical lateral and a horizontal lateral direction; and
the second infrared camera is positioned relative to the second visible-transmissive infrared mirror in one of the vertical lateral and the horizontal lateral direction.

11. The system to determine a binocular alignment of claim 1, wherein:
the first optical unit includes a first lens assembly,
to receive and guide the infrared eye-tracking beam and the infrared imaging light, both reflected from the first eye, towards the first infrared camera, and
to reduce at least one of a chromatic aberration, an optical aberration, an optical astigmatism, and a wavefront distortion; and
the second optical unit includes a second lens assembly
to receive and guide the infrared eye-tracking beam and the infrared imaging light, both reflected from the second eye, towards the first infrared camera, and
to reduce at least one of a chromatic aberration, an optical aberration, an optical astigmatism, and a wavefront distortion.

12. The system to determine a binocular alignment of claim of 11, wherein:
the first infrared camera and the first lens assembly are adjustable together; and
the second infrared camera and the second lens assembly are adjustable together.

13. The system to determine a binocular alignment of claim 1, wherein:
the first eye-tracker assembly includes a first auto-refractor, to determine refractive information about the first eye; and
the second eye-tracker assembly includes a second auto-refractor, to determine refractive information about the second eye.

14. The system to determine a binocular alignment of claim 13, wherein:
the first auto-refractor includes
a first infrared light source, to project a wavefront IR light into the first eye,
a first microlens array, to receive and split a reflected wavefront IR light from the first eye into beamlets, and
a first wavefront camera to analyze the beamlets to determine the refractive information about the first eye; and
the second auto-refractor includes
a second infrared light source, to project a wavefront IR light into the second eye,
a second microlens array, to receive and split a reflected wavefront IR light from the second eye into beamlets, and
a second wavefront camera to analyze the beamlets to determine the refractive information about the second eye.

15. The system to determine a binocular alignment of claim 13, wherein:
the first auto-refractor utilizes at least one of Talbot-Moire interferometry, slit lamp technology, Tscherning aberrometry, and lensometer technology.

16. The system to determine a binocular alignment of claim 13, wherein:
the system to determine a binocular alignment is configured to determine a vergence response and an accommodative response in an integrated manner by
the first display and the first eye tracker assembly, and the second display and the second eye tracker assembly being configured to determine the vergence response, and
the first display and the first auto-refractor, and the second display and the second auto-refractor being configured to determine the accommodative response.

17. The system to determine a binocular alignment of claim 1, wherein:
a first display is actuatable to a first longitudinal position according to the simulated distance, wherein
the first longitudinal position is dynamically corrected according to the optical power of the first eye; and
a second display is actuatable to a second longitudinal position according to the simulated distance, wherein
the second longitudinal position is dynamically corrected according to the optical power of the second eye.

18. The system to determine a binocular alignment of claim 1, comprising:
a nose bridge, located centrally between the first optical unit and the second optical unit, configured to receive and immobilize a patient's nose.

19. The system to determine a binocular alignment of claim 18, wherein:

the first eye tracker assembly is adjustable in the horizontal lateral direction relative to the nose bridge to accommodate the pupillary distance of the first eye; and the second eye tracker assembly is adjustable in the horizontal lateral direction relative to the nose bridge to accommodate the pupillary distance of the second eye.

20. The system to determine a binocular alignment of claim 1, the first display and the second display comprising:
at least one of a liquid crystal display, a light emitting diode (LED) display, an organic LED display, a quantum dot LED display, a microlens array, a digital mirror device, and a scanning projector micro-electrical-mechanical system.

21. The system to determine a binocular alignment of claim 1, wherein:
the first display is configured to display images for the first eye modified according to at least one of an optical power, a cylinder, and a prism of the first eye; and
the second display is configured to display images for the second eye modified according to at least one of an optical power, a cylinder, and a prism of the second eye.

22. The system to determine a binocular alignment of claim 1, comprising:
a graphical user interface, configured for a medical operator to interact with the computer to manage the determination of the binocular alignment.

23. The system to determine a binocular alignment of claim 1, comprising:
a patient communication interface, including at least one of
a loudspeaker, configured to instruct a patient to follow steps of the determination of the binocular alignment; and
a patient feedback portal, configured to receive a feedback from the patient, selected from the group consisting of a push-button, a track wheel, a touchpad, a microphone, and an audio-interactive device.

24. The system to determine a binocular alignment of claim 1, wherein:
the computer is configured to determine a Fixation Disparity of a patient as an amount of angular misalignment between a central target and a peripheral fusion lock of moving targets around an image with a blank center, as part of the determining of the binocular alignment.

25. The system to determine a binocular alignment of claim 1, wherein:
the computer is configured to determine a Gross Phoria as an average amount of angular misalignment between the first eye and the second eye when the first display and the second display display dissimilar images with one of the eyes fixated on a target at a time, as part of the determining of the binocular alignment.

26. A system to determine a binocular alignment, comprising:
a first optical unit, including
a first display, to display images for a first eye, actuatable along a lateral actuation direction according to a simulated distance and an optical power of the first eye, and
a first eye tracker assembly, to track a gaze direction of the first eye, adjustable in a horizontal lateral direction to accommodate a pupillary distance of the first eye, the first eye tracker assembly includes
one or more first infrared light emitting diodes, to project an infrared eye-tracking beam on the first eye;
a first infrared light source, to illuminate the first eye with an infrared imaging light;
a first infrared camera, positioned along a longitudinal direction to detect the infrared eye-tracking beam and the infrared imaging light, both reflected from the first eye; and
a first infrared-transmissive visible mirror,
to transmit the reflected infrared eye-tracking beam and the infrared imaging light from the first eye to the first infrared camera along the longitudinal direction; and
to redirect images from the lateral actuation direction of the first display to the longitudinal direction towards the first eye; and
a second optical unit, including
a second display, to display images for a second eye, actuatable along the lateral actuation direction according to a simulated distance and an optical power of the second eye, and
a second eye tracker assembly, to track a gaze direction of the second eye, adjustable in the horizontal lateral direction to accommodate a pupillary distance of the second eye, the second eye tracker assembly includes
one or more second infrared light emitting diodes, to project an infrared eye-tracking beam on the second eye;
a second infrared light source, to illuminate the second eye with an infrared imaging light;
a second infrared camera, positioned along the longitudinal direction to detect the infrared eye-tracking beam and the infrared imaging light, both reflected from the second eye; and
a second infrared-transmissive visible mirror,
to transmit the reflected infrared eye-tracking beam and the infrared imaging light from the second eye to the second infrared camera along the longitudinal direction; and
to redirect images from the lateral actuation direction of the second display to the longitudinal direction towards the second eye; and
a computer, coupled to the first optical unit and the second optical unit, to determine the binocular alignment based on the gaze directions of the first eye and the second eye.

* * * * *